US009599584B2

(12) United States Patent
Yazami et al.

(10) Patent No.: US 9,599,584 B2
(45) Date of Patent: Mar. 21, 2017

(54) IMBEDDED CHIP FOR BATTERY APPLICATIONS

(71) Applicants: Rachid Yazami, Singapore (SG); Cher Ming Tan, Singapore (SG)

(72) Inventors: Rachid Yazami, Singapore (SG); Cher Ming Tan, Singapore (SG)

(73) Assignees: CALIFORNIA INSTITUTE OF TECHNOLOGY, Pasadena, CA (US); CENTRE NATIONAL DE LA RECHERCHE SCIENTIFIQUE (C.N.R.S.), Paris (FR); NANYANG TECHNOLOGICAL UNIVERSITY, Singapore (SG)

( * ) Notice: Subject to any disclaimer, the term of this patent is extended or adjusted under 35 U.S.C. 154(b) by 920 days.

(21) Appl. No.: 13/871,454

(22) Filed: Apr. 26, 2013

(65) Prior Publication Data
US 2013/0322488 A1  Dec. 5, 2013

Related U.S. Application Data

(60) Provisional application No. 61/639,712, filed on Apr. 27, 2012.

(51) Int. Cl.
*G01K 1/18* (2006.01)
*G01N 27/27* (2006.01)
(Continued)

(52) U.S. Cl.
CPC .............. *G01N 27/27* (2013.01); *B60L 1/003* (2013.01); *B60L 1/02* (2013.01); *B60L 3/0046* (2013.01);
(Continued)

(58) Field of Classification Search
CPC .... G01N 27/27; H01M 10/48; H01M 10/486; B60L 1/003; B60L 11/005; B60L 11/1872;
(Continued)

(56) References Cited

U.S. PATENT DOCUMENTS 4,295,097 A   10/1981   Thompson et al.
4,438,086 A   3/1984   Aramaki et al.
(Continued)

FOREIGN PATENT DOCUMENTS

CN   1525592      9/2004
CN   1604373 A    4/2005
(Continued)

OTHER PUBLICATIONS

Extended European Search Report, dated Nov. 25, 2015, corresponding to European Patent Application No. 13825023.8; 9 pages.
(Continued)

*Primary Examiner* — Lisa Caputo
*Assistant Examiner* — Janice M Soto
(74) *Attorney, Agent, or Firm* — Lathrop & Gage LLP

(57) ABSTRACT

Provided are methods, systems and devices for thermodynamically evaluating electrochemical systems and components thereof, including electrochemical cells such as batteries. The present systems and methods are capable of monitoring selected electrochemical cell conditions, such as temperature, open circuit voltage and/or composition, and carrying out measurements of a number of cell parameters, including open circuit voltage, time and temperature, with accuracies large enough to allow for precise determination of thermodynamic state functions and materials properties relating to the composition, phase, states of charge, health and safety and electrochemical properties of electrodes and electrolytes in an electrochemical cell. Thermodynamic
(Continued)

measurement systems of the present invention are highly versatile and provide information for predicting a wide range of performance attributes for virtually any electrochemical system having an electrode pair.

29 Claims, 41 Drawing Sheets

(51) Int. Cl.
| | |
|---|---|
| G01R 31/36 | (2006.01) |
| B60L 11/18 | (2006.01) |
| H01M 10/48 | (2006.01) |
| B60L 1/00 | (2006.01) |
| B60L 1/02 | (2006.01) |
| B60L 3/00 | (2006.01) |
| B60L 3/12 | (2006.01) |
| B60L 11/00 | (2006.01) |
| H01M 10/42 | (2006.01) |
| H01M 10/44 | (2006.01) |

(52) U.S. Cl.
CPC .............. *B60L 3/0053* (2013.01); *B60L 3/12* (2013.01); *B60L 11/005* (2013.01); *B60L 11/189* (2013.01); *B60L 11/1857* (2013.01); *B60L 11/1861* (2013.01); *B60L 11/1872* (2013.01); *B60L 11/1874* (2013.01); *B60L 11/1875* (2013.01); *B60L 11/1894* (2013.01); *G01R 31/3606* (2013.01); *H01M 10/48* (2013.01); *H01M 10/486* (2013.01); *B60L 11/1892* (2013.01); *B60L 2240/12* (2013.01); *B60L 2240/545* (2013.01); *B60L 2240/547* (2013.01); *B60L 2240/549* (2013.01); *B60L 2240/80* (2013.01); *B60L 2260/22* (2013.01); *G01R 31/362* (2013.01); *H01M 10/448* (2013.01); *H01M 2010/4271* (2013.01); *Y02T 10/705* (2013.01); *Y02T 10/7022* (2013.01); *Y02T 10/7044* (2013.01); *Y02T 90/34* (2013.01)

(58) Field of Classification Search
CPC .... B60L 3/0053; B60L 11/189; B60L 3/0046; B60L 11/1894; B60L 11/1874; B60L 11/1857; B60L 11/1875; B60L 1/02; B60L 3/12; B60L 11/1861; G01R 31/3606; Y02T 90/34
See application file for complete search history.

(56) References Cited

U.S. PATENT DOCUMENTS

| | | | |
|---|---|---|---|
| 4,725,784 A | 2/1988 | Peled et al. | |
| 5,477,125 A * | 12/1995 | Ettel | H02J 7/0086 320/156 |
| 6,016,047 A | 1/2000 | Notten et al. | |
| 6,068,921 A | 5/2000 | Yamana et al. | |
| 6,392,385 B1 | 5/2002 | Barker et al. | |
| 6,667,131 B1 | 12/2003 | Vitins et al. | |
| 6,794,876 B2 | 9/2004 | Kawaguchi et al. | |
| 6,832,171 B2 | 12/2004 | Barsoukov et al. | |
| 7,081,755 B2 | 7/2006 | Klang et al. | |
| 7,109,685 B2 | 9/2006 | Tate, Jr. et al. | |
| 7,132,832 B2 | 11/2006 | Vaillancourt et al. | |
| 7,227,336 B1 | 6/2007 | Van Schalkwijk et al. | |
| 7,525,284 B2 | 4/2009 | Iwane et al. | |
| 7,541,775 B2 | 6/2009 | Lee | |
| 7,563,542 B2 | 7/2009 | Yazami et al. | |
| 7,595,611 B2 | 9/2009 | Reynier et al. | |
| 8,103,485 B2 | 1/2012 | Plett | |
| 8,446,127 B2 | 5/2013 | Yazami et al. | |
| 9,065,292 B2 | 6/2015 | Yazami | |
| 2001/0001533 A1 | 5/2001 | Stuck Andersen et al. | |
| 2004/0046564 A1 | 3/2004 | Klang et al. | |
| 2004/0128089 A1 | 7/2004 | Barsoukov et al. | |
| 2004/0220758 A1 | 11/2004 | Barsoukov et al. | |
| 2005/0073315 A1 | 4/2005 | Murakami et al. | |
| 2006/0100833 A1 | 5/2006 | Plett | |
| 2006/0208704 A1 | 9/2006 | Iwane et al. | |
| 2007/0182418 A1 | 8/2007 | Reynier et al. | |
| 2007/0299620 A1 | 12/2007 | Yun et al. | |
| 2008/0280192 A1 * | 11/2008 | Drozdz | B60K 6/28 429/62 |
| 2009/0024339 A1 | 1/2009 | Shoji | |
| 2009/0172825 A1 | 7/2009 | Yi et al. | |
| 2010/0090650 A1 * | 4/2010 | Yazami | H01M 10/443 320/132 |
| 2011/0054816 A1 | 3/2011 | Prada et al. | |
| 2011/0074430 A1 | 3/2011 | Tsuruta et al. | |
| 2011/0121783 A1 | 5/2011 | Boyles et al. | |
| 2011/0121786 A1 | 5/2011 | Tsuruta et al. | |
| 2012/0043929 A1 | 2/2012 | Yazami | |
| 2013/0271089 A1 | 10/2013 | Yazami et al. | |

FOREIGN PATENT DOCUMENTS

| | | |
|---|---|---|
| CN | 1604383 A | 6/2005 |
| CN | 101098029 A | 1/2008 |
| EP | 0118292 A2 | 9/1984 |
| EP | 0867958 | 9/1998 |
| EP | 0 898 321 | 2/1999 |
| EP | 1460441 | 9/2004 |
| EP | 1524712 | 4/2005 |
| EP | 1643260 | 4/2006 |
| JP | 07-065833 | 3/1995 |
| JP | 09-113589 | 5/1997 |
| JP | 10-275617 | 10/1998 |
| JP | 10-302765 | 11/1998 |
| JP | 11-040189 | 2/1999 |
| JP | 2002521792 | 7/2002 |
| JP | 2003502792 | 1/2003 |
| JP | 2003523049 | 7/2003 |
| JP | 2005043339 A | 2/2005 |
| KR | 10-2008-0000160 | 1/2008 |
| KR | 10-2008-0000160 | 7/2009 |
| WO | WO99/56121 | 11/1999 |
| WO | WO00/05596 | 2/2000 |
| WO | WO 01/59443 | 8/2001 |
| WO | WO 2007/117263 | 10/2007 |
| WO | WO 2010/105062 | 9/2010 |
| WO | WO 2014/021957 | 2/2014 |

OTHER PUBLICATIONS

International Preliminary Report on Patentability mailed Nov. 6, 2014, for International Application No. PCT/US2013/038407.
Notice of Reasons for Rejection dispatched Aug. 19, 2014, corresponding the Japanese Patent Application No. P2012-255415.
International Search Report and Written Opinion mailed Feb. 26, 2014, for International Application No. PCT/US2013/038407.
Al Hallaj et al. (2000) "Characterization of Commercial Li-Ion Batteries Using Electrochemical-Calorimetric Measurements," *Journal of Power Sources.* 87(1-2):186-194.
Al Hallaj et al. (2000) "Entropy Changes Due to Structural Transformation in the Graphite Anode and Phase Change of the $LiCoO_2$ cathode," *Journal of the Electrochemical Society.* 147(7):2432-2436.
Amatucci et al. (1996) "$CoO_2$, the End Member of the $Li_x CoO_2$ solid solution," *Journal of the Electrochemical Society.* 143(3):1114-1123.
Amatucci et al. (1997) "Surface Treatments of $Li_{1+}Mn_2 2-xO_4$ for Improved elevated Temperature Performance," *Solid State Ionics.* 104(1-2):13-25.
Amatucci et al. (1999) "The Elevated Temperature Performance of the $LiMn_2O_4$/C System: Failure and Solutions," *Electrochimica Acta.* 45(1-2):255-271.

(56) References Cited

OTHER PUBLICATIONS

Andre et al. (Mar. 2013) "Comparative Study of a Structured Neural Network and an Extended Kalman Filter for State of Health Determination of Lithium-Ion Batteries in Hybrid Electricvehicles," *Engineering Applications of Artificial Intelligence.* 26:951-961.

Attidekou et al. (2007) "Thermodynamic Aspects of the Reaction of Lithium with $SnP_2O_7$ Based Positive Electrodes," *Journal of the Electrochemical Society.* 154(3):A217-A220.

Aurbach et al. (1999) "Capacity Fading of $Li_xMn_2O_4$ Spinel Electrodes Studied by XRD and Electroanalytical Techniques," Journal of Power Sources. 81:472-479.

Aydinol et al. (1997) "Study of Lithium Intercalation in Metal Oxides and Metal Dichalcogenides," *Physical Review B.* 56(3):1354-1365.

Baddour et al. (1991) "A Thermodynamic, Structural and Kinetic-Study of the Electrochemical Lithium Intercalation Into the Xerogel $V_2O_5 \cap 1.6\ H_2O$ in a Propylene Carbonate Solution," *Journal of Electroanalytical Chemistry.* 314(1-2):81-101.

Barbato et al. (2001) "Hollandite Cathodes for Lithium Ion Batteries. 2. Thermodynamic and Kinetics Studies of Lithium Insertion Into $BaMMn_7O_{16}$ (M=Mg, Mn, Fe, Ni)," *Electrochimica Acta.* 46(18):2767-2776.

Barker et al. (1995) "Kinetics and Thermodynamics of the Lithium Insertion Reaction in Spinel Phase $Li_xMn_2O_4$," *Journal of Power Sources.* 54(2):475-478.

Benco et al. (1999) First principles calculation of electrode material for lithium intercalation batteries: TiS2 and LiTi2S4 cubic spinel structures, *Journal of Solid State Chemistry.* 145(2):503-510.

Bernardi et al. (2011) "Analysis of Pulse and Relaxation Behavior in Lithium-Ion Batteries," *J. Power Sources.* 196:412-427.

Bhatia et al. (1997) "Effect of Sintering Temperature on the Characteristics of Carbons Based on Mesocarbon Microbeads," *J. Mater. Science.* 32:135-139.

Billaud et al. (1996) "Revisited Structures of Dense and Dilute Stage II Lithium-Graphite Intercalation Compounds," *Journal of Physics and Chemistry of Solids.* 57(6-8):775-781.

Botte et al. (2000) "Mathematical Modeling of Secondary Lithium Batteries," *Electrochimica Acta.* 45(15-16):2595-2609.

Carlier et al. (2003) "First-principles investigation of phase stability in the $O$-2-$LiCoO_2$ system," *Chemistry of Materials.* 15(13):2651-2660.

Ceder et al. (1998) "Thermodynamics of oxides with substitutional disorder: A microscopic model and evaluation of important energy contributions," *Journal of the American Ceramic Society.* 81(3):517-525.

Ceder et al. (1999) "Phase Diagrams of Lithium Transition Metal Oxides: Investigations From First Principles," *Electrochimica Acta.* 45(1-2):131-150.

Chen et al. (2002) "Staging Phase Transitions in $Li_xCoO_2$," *Journal of the Electrochemical Society.* 149(12):A1604-A1609.

Chen et al. (2003) "First Principle Investigation of Positive Electrode Material for Lithium Ion Batteries," *Rare Metal Materials and Engineering.* 32(9):693-698.

Coleman et al. (2007) "State-of-Charge Determination From EMF Voltage Estimation: Using Impedance, Terminal Voltage, and Current for Lead-Acid and Lithium-Ion Batteries," *IEEE Trans. Ind. Electron.* 54:2250-2257.

Dahn et al. (1983), "Entropy measurements on $LirTiS_2$", Can. J. Phys. vol. 61, pp. 1093-1098.

Deiss et al. (1997) "Average Voltage, Energy Density, and Specific Energy of Lithium-Ion Batteries—Calculation Based on First Principles," *Journal of the Electrochemical Society.* 144(11):3877-3881.

Doi et al. (2007) "Computer Simulation of a Porous Positive Electrode for Lithium Batteries," *Journal of Power Sources.* 174(2):779-783.

Eddahech et al. (2012) "Behavior and State-of-Health Monitoring of Li-Ion Batteries Using Impedance Spectroscopy and Recurrent Neural Networks," *Electrical Power and Energy Systems.* 42 :487-494.

Filhol et al. (2008) "Phase Diagrams for Systems With Low Free Energy Variation: A Coupled Theory/Experiments Method Applied to Li-Graphite," *Journal of Physical Chemistry C.* 112(10):3982-3988.

Franklin (Oct. 23, 1951) "Crystallite Growth in Graphitizing and Non-Graphitizing Carbons," *Proceedings of the Royal Society of London. Series A, Mathematical and Physical Sciences.* 209(1097):196-218.

Fujiwara et al. (2003) "Determination of standard free energy of formation for niobium silicides by EMF measurements," *Journal of the Electrochemical Society.* 150(8):J43-J48.

Funahashi et al. (2002) "Thermal simulation of large-scale lithium secondary batteries using a graphite-coke hybrid carbon negative electrode and $LiNi_{0.7}CO_{0.3}O_2$ positive electrode," *Journal of Power Sources.* 104(2):248-252.

Gabrisch et al. (2004) "Hexagonal to Cubic Spinel Transformation in Lithiated Cobalt Oxide—TEM Investigation," *Journal of the Electrochemical Society.* 151(6):A891-A897.

Gabrisch et al. (2008) "Transmission electron microscope studies of $LiNi_{1/3}Mn_{1/3}Co_{1/3}O2$ before and after long-term aging at 70 degrees C.," *Electrochemical and Solid-State Letters Volume.* 11(7): 119-24, 2008.

Garcia-Belmonte et al. (2006) "Correlation Between Volume Change and Cell Voltage Variation with Composition for Lithium Intercalated Amorphous Films," *Journal of Physical Chemistry B.* 110(10):4514-4518.

Gautier et al. (1997) "Effect of the $ZnNi_yMn_{2-y}O_4$ ($0 <=y <=1$) Spinel Composition on Electrochemical Lithium Insertion," *Journal of Solid State Electrochemistry.* 1(2):126133.

Gong et al. (2000) "Electrochemical Intercalation of Lithium Species Into Disordered Carbon Prepared by the Heat-Treatment of Poly (P-Phenylene) at 650 degrees C. for anode in lithium-ion battery," *Electrochimica Acta.* 45(11):1753-1762.

Graetz et al. (2002) "Electronic Structure of Chemically-Delithiated $LiCoO_2$ Studied by Electron Energy-Loss Spectrometry," *Journal of Physical Chemistry B.* 106(6):1286-1289.

Guzman et al. (1996) "Lithium Intercalation Studies in Hydrated Molybdenum Oxides," *Solid State Ionics.* 86-8 Part 1:407-413.

Gupta et al. (1972), "Thermodynamic and Physical Properties of Molten Sodium Polysulfides from Open-Circuit Voltage Measurements", J. Electrochem. Soc.: Pentane Electrosorption on Pt Electrodes, vol. 119, No. 8, pp. 1033-1037.

Hallstedt et al. (2007) "Thermodynamic assessment of the Al-Li system," *International Journal of Materials Research.* 98 (10): 961-969.

Hill (1992) "Microcalorimetric Studies on Lithium Thionyl Chloride Cells—Temperature Effects Between 25-degrees-C. and -40-degrees-C.," *Journal of Power Sources.* 39(1):83-94.

Hong et al. (1998) "Electrochemical-Calorimetric Studies of Lithium-Ion Cells," *Journal of the Electrochemical Society.* 145(5):1489-1501.

Hong et al. (2000) "Relationship Between Calorimetric and Structural Characteristics of Lithium-Ion Cells—I. Thermal analysis and Phase Diagram," *Journal of the Electrochemical Society.* 147(9):3183-3189.

Hu et al. (2010), "Effects of the $LiFePO_4$ content and the preparation method on the properties of $(LiFePO_4+AC)/Li_4Ti_5O_{12}$ hybrid battery-capacitors", J. Serb. Chem. Soc. 75 (9) 1259-1269.

Huang et al. (1999) "Correlating Capacity Loss of Stoichiometric and Nonstoichiometric Lithium Manganese Oxide Spinel Electrodes with Their Structural Integrity," *Journal of the Electrochemical Society.* 146(10):3649-3654.

Huang et al. (2006) "Thermal Study on Single Electrodes in Lithium-Ion Battery." *Journal of Power Sources.* 156(2):541-546.

Huggins (1999) "Lithium Alloy Negative Electrodes," *Journal of Power Sources.* 82:13-19.

Idemoto et al. (2000) "Thermodynamic Stability and Cathode performance of Limn2-xmgxo4 as Cathode Active Material for the Lithium Secondary Battery," *Electrochemistry* 68(6):469-473.

(56) References Cited

OTHER PUBLICATIONS

Idemoto et al. (2006) "Dependence of Properties, Crystal Structure and Electrode Characteristics on Li Content for Lix(Ni,Co)O2 as a Cathode Active Material for Li Secondary Batteries," 210th Meeting of the Electrochemical Society, Oct. 29-Nov. 3, 2006, Moon Palace Resort Hotel, Cancun Mexico, Abstract # 13.
Idemoto et al. (2006) "Dependence of Properties, Crystal Structure and Electrode Characteristics on Li Content for LixCo1/3Ni1/3Mn1/3O2+δ as a Cathode Active Material for Li Secondary Battery," *Electrochemistry* 74(9):752-757.
Idemoto et al. (Mar. 9, 2000) "Thermodynamic Stability and Cathode Performance of Li1+xMn2−xO4 as a Cathode Active Material for Lithium Secondary Battery," *J. Ceram. Soc. Jpn.* 108(9):848-853.
Idemoto et al. (2003), "Crystal structure and cathode performance dependence on oxygen content of $LiMn_{1.5}Ni_{0.5}O_4$ as a cathode material for secondary lithium batteries," Journal of Power Sources 119-121 (2003) 125-129.
International Search Report and Written Opinion, Corresponding to International Application No. PCT/2010/026991, Mailed May 12, 2010.
International Search Report and Written Opinion, Corresponding to International Application No. PCT/US06/30137, Mailed Jun. 10, 2008.
Joo et al. (2006) "Phase Behaviors of Solid Polymer Electrolytes/Salt System in Lithium Secondary Battery by Group-Contribution Method: The Pressure Effect," *Polymer*. 47(1): 211-217.
Joo et al. (2006) "Molecular Thermodynamics Approach for Phase Behaviors of Solid Polymer Electrolytes/Salt System in Lithium Secondary Battery on the Nonrandom Mixing Effect: Applicability of the Group-Contribution Method," Polymer. 47(20):7153-7159.
Kalikmanov (2002) "Role of Elasticity Forces in Thermodynamics of Intercalation Compounds: Self-Consistent Mean-Field Theory and Monte Carlo simulations," *Journal of Chemical Physics*. 116(7):3083-3089.
Kataoka, (2002) "Lithium Storage Mechanism of Disordered Mesophase Carbon Fibers Studied by $^7$Li-Nuclear Magnetic Resonance," *Electrochem. and Solid-State Lett.* 5:A10-A13.
Kiehne, M. D.: Eds. (2003) "Battery and Technology Handbook," $2^{nd}$ Ed. CRC Press.
Kim et al. (2001) "Thermodynamic and Kinetic Approaches to Lithium Intercalation Into a $Li_1$ -Delta $Mn_2O_4$ Electrode Using Monte Carlo Simulation," *Electrochimica Acta*. 46(7):987-997.
Kobayashi et al. (2004) "Structural Determination of $Li_{1-y}Ni_{0.5}Mn_{0.5}O2$ (y=0.5) Using a Combination of Rietveld Analysis and the Maximum Entropy Method," *Journal of Materials Chemistry*. 14(1):40-42.
Korovin (1998) "Electrochemical Intercalation into Cathodic Materials: Electrode Potentials," *Russian Journal of Electrochemistry*. 34:669-675.
Koudriachova et al. (2004) "First Principles Predictions for Intercalation Behavior," *Solid State Ionics*. 175(1-4):829-834.
Kuhn et al. (2007) "On the Synthesis of Ramsdellite $LiTiMO_4$ (M=Ti, V, Cr, Mn, Fe): An Experimental and Computational Study of the Spinel-Ramsdellite Transformation," *European Journal of Inorganic Chemistry*. (21):3375-3384.
Kudo et al. (1998) "Theoretical Dependence of the Free Energy and Chemical Potential Upon Composition in Intercalation Systems with Repulsive Interaction Between Guest Ions," *Electrochem. Acta*. 43(7):781-789.
Kumagai et al. (1997) "Electrochemical intercalation of Lithium into Hexagonal Tungsten Trioxide," Thermochimica Acta. 299(1-2):19-25.
Kumagai et al. (1997) "Thermodynamics and Kinetics of Electrochemical Intercalation of Lithium Into $Li_{0.50}WO_{3.25}$ with a Hexagonal Tungsten Bronze Structure," *Solid State Ionics*. 98(3-4):159-166.
Kumagai et al. (1999) "Thermodynamics and Kinetics of Lithium Intercalation Into $Nb_2O_5$ Electrodes for a 2 V Rechargeable Lithium Battery," Journal of the Electrochemical Society. 146(9):3203-3210.
Kumagai, et al. (1993) "Thermodynamic and Kinetic-Studies of Electrochemical Lithium Insertion Into Quaternary Li—Mn—V—O Spinel as Positive Materials for Rechargeable Lithium Batteries," *Journal of the Electrochemical Society*. 140(11):3194-3199.
Kumaresan et al. (2008) "Thermal Model for a Li-Ion Cell," *Journal of the Electrochemical Society*. 155:A164-A171.
Lee et al. (2003) "Identity and Thermodynamics of Lithium Intercalated in Graphite," *Journal of Power Sources*. 114(2):285-291.
Letellier et al. (2004) "The First in Situ $^7$Li NMR Study of the Reversible Lithium Insertion Mechanism in Disorganised Carbons," *J. Phys. and Chem. of Solids* 65:245-251.
Limthongkul et al. (2003) "Electrochemically-Driven Solid-State Amorphization in Lithium-Metal Anodes," *Journal of Power Sources*. 119:604-609.
Lin et al. (Oct. 4, 2012) "Estimation of Battery State of Health Using Probabilistic Neural Network," *IEEE Transactions on Industrial Informatics*. 9(2):679-685.
Linden, D.; Reddy, T.: Eds. (2002) "Handbook of Batteries," $3^{rd}$ Ed. Mcgraw Hill.
Lu et al. (2006) "Determination of the Reversible and Irreversible Heats of $LiNi_{0.8}Co_{0.2}O_2$/Mesocarbon Microbead Li-Ion Cell Reactions Using Isothermal Microcalorimetery," *Electrochimica Acta*. 51(7):1322-1329.
Lu et al. (2006) "In Situ Thermal Study of $Li_{1+x}[Ni_{1/3}Co_{1/3}Mn_{1/3}]_{(1-x)}O_2$ Using Isothermal Micro-Calorimetric Techniques," *Journal of the Electrochemical Society*. 153(11):A2147-A2151.
Lu et al. (2007) "Isothermal Calorimetry Investigation of $Li_{1+x}Mn_{2-y}Al_zO_{4\ spinel}$," *Electrochimica Acta*. 52(19):5837-5842.
Lu et al. (2007) "Thermal Properties of $Li_{4/3}Ti_{5/3}O_4/LiMn_2O_4$ Cell," *Journal of Power Sources*. 174:673-677.
Mabuchi et al. (1995) "Charge-Discharge Characteristics of the Mesocarbon Miocrobeads Heat-Treated at Different Temperatures," *J. Electrochem. Soc.* 142:1041-1046.
Maier (2007) "Size effects on Mass Transport and Storage in Lithium Batteries," *Journal of Power Sources*. 174:569-574.
McMenamin et al. (Dec. 8, 2008) "Using Electrochemical Thermodynamic Measurements to Detect Effects of Battery Aging," Lithium Mobile Power 2008, Las Vegas; Power Point Presentation.
Mering et al. (1960) *J. Chim. Phys. Fr.* 57:803.
Mori et al. (1995) "Lithium Doping/Undoping in Disordered Coke Carbons," *J. Power Sources* 56:205-208.
Ng et al. (2009) "An Enhanced Coulomb Counting Method for Estimating State-of-Charge and State-of-Health of Lead-Acid Batteries," *INTELEC 31st*, Incheon, Korea.
Ng et al. (2009) "Enhanced Coulomb Counting Method for Estimating State-of-Charge and State-of-Health of Lithium Ion Batteries," *Applied Energy*. 86:1506-1511.
Nikiel (1993) "Raman-Spectroscopic Characterization of Graphites—A Reevaluation of Spectra/Structure Correlation," *Carbon*. 31(8):1313-1317.
Oberlin (1984) "Carbonization and Graphitization," *Carbon*. 22(6):521-541.
Oberlin et al. (1975) "Graphitization Studies of Anthracites by High-Resolution Electron-Microscopy," *Carbon*. 13:367.
Ohshima et al. (2006) "Thermal Behavior of Small Lithium-Ion Secondary Battery During Rapid Charge and Discharge Cycles," *Electrical Engineering in Japan*. 157(3):17-25.
Ohzuku et al. (1994) "Solid-State Redox Reactions of $LiCoO_2$ (R$\bar{3}$m) for 4 volt secondary lithium cells," *Journal of the Electrochemical Society*. 141(11):2972-2977.
Okamoto et al. (2007) "Analysis of Heat Generation of Lithium Ion Rechargeable Batteries Used in Implantable Battery Systems for Driving Undulation Pump Ventricular Assist Device," *Artificial Organs*. 31(7):538-541.
Ol'shanskaya et al. (2002) "Thermodynamics of Lithium Intercalates in Carbonized Fabric," *Russian Journal of Applied Chemistry*. 75(5):740-744.
Paddon et al. (2007) "Kinetics and Thermodynamics of the Li/Li+ Couple in Tetrahydrofuran at Low Temperatures (195-295 K)," Journal of Physical Organic Chemistry. 20(9):677-684.
Papanek et al. (1996) "Lithium Insertion in Disordered Carbon-Hydrogen Alloys: Intercalation vs. Covalent Binding," *Chem. Mater.* 8:1519-1526.

(56) References Cited

OTHER PUBLICATIONS

Papanek et al. (2001) "Neutron Scattering Studies of Disordered Carbon Anode Materials," *J. Phys. Condens. Matter* 13:8287-8301.
Piller et al. (2001) "Methods for State-of-Charge Determination and Their Applications" *J. Power Sources.* 96:113-120.
Quintin et al. (2006) "Study of the Lithium Insertion-Deinsertion Mechanism in Nanocrystalline Gamma-$Fe_2O_3$ Electrodes by Means of Electrochemical Impedance Spectroscopy," *Electrochimica Acta.* 51(28): 6426-6434.
Rao et al. (1997) "Heat-Generation Rate and General Energy Balance for Insertion Battery Systems," *Journal of the Electrochemical Society.* 144(8):2697-2704.
Remmlinger et al. (2011) "State-of-Health Monitoring of Lithium-Ion Batteries in Electric Vehicles by On-Board Internal Resistance Estimation," *J. Power Sources.* 196:5357-5363.
Reynier et al. (2003) "The Entropy and Enthalpy of Lithium Intercalation into Graphite," *Journal of Power Sources.* 119:850-855.
Reynier et al. (2004) "Thermodynamics of Lithium Intercalation into Graphites and Disordered Carbons," *J. Electrochem. Soc.* 151(3):A422-A426.
Reynier et al. (2004) "Entropy of Li intercalation in LixCoO2," Physical Review B 70, 174304.
Reynier et al. (2007) "Evolution of lithiation thermodynamics with the graphitization of carbons," J. Power Sources 165:552-558.
Saito et al. (1997) "Thermal Studies of a Lithium-Ion Battery," *Journal of Power Sources.* 68(2):451-454.
Sandhu et al. (1999) "Thermodynamic Equations for a Model Lithium-Ion Cell," *Electrochimica Acta.* 45(6):969-976.
Schoonman (2003) "Nanoionics," *Solid State Ionics.* 157(1-4):319-326.
Selman et al. (2001) "Cooperative Research on Safety Fundamentals of Lithium Batteries," *Journal of Power Sources.* 97(8):726-732.
Shi et al. (2003) "First-Principles Studies of Cation-Doped Spine $LiMn_2O_4$ for Lithium Ion Batteries," *Physical Review B.* 67(11).
Shi et al. (2007) "Effect of Mg-Doping on the Structural and Electronic Properties of $LiCoO_2$: A First-Principles Investigation," *Journal of Power Sources.* 171:908-912.
Shin et al. (2004) "Factors Influencing the Capacity Fade of Spinel Lithium Manganese Oxides," *Journal of the Electrochemical Society.* 151(2):A204-A208.
Shiraishi et al. (2001) "EELS Analysis of Electrochemically Deintercalated $Li_{1-x}Mn_2_4$ and Substituted Spinets $LiMn_{1.6}Mn_{1.6}M_{0.4}O_4$ (M=Co, Cr, Ni)," *Journal of Power Sources.* 97(8):461-464.
Snihir et al. (2006) "Battery Open-circuit Voltage Estimation by a Method of Statistical Analysis," *J. Power Sources.* 159(2):1484-1487.
Stevens et al. (2001) "The Mechanisms of Lithium and Sodium Insertion in Carbon Materials," *J. Electrochem. Soc.* 148:A803-A811.
Takahashi et al. (2007) "Structure and Electron Density Analysis of Electrochemically and Chemically Delithiated $LiCoO_2$ Single Crystals," *Journal of Solid State Chemistry.* 180(1):313-321.
Takano et al. (2002) "Entropy Change in Lithium Ion Cells on Charge and Discharge," *Journal of Applied Electrochemistry.* 32(3):251-258.
Tarascon et al. "Li Metal-Free Rechargeable Batteries Based on $Li_1 + xMn_2O_4$ Cathodes (0< x< 1) and Carbon Anodes," *J. Electrochem. Soc.*138(10):2864-2868.
Thomas et al. (2001) "Measurement of the Entropy of Reaction as a Function of State of Charge in Doped and Undoped Lithium Manganese Oxide," *Journal of the Electrochemical Society.* 148(6):A570-A575.
Thomas et al. (2003) "Heats of Mixing and of Entropy in Porous Insertion Electrodes," *Journal of Power Sources.* 119:844-849.
Thomas et al. (2003) "Thermal Modeling of Porous Insertion Electrodes," *Journal of the Electrochemical Society.* 150(2):A176-A192.
Tuinstra et al. (1970) "Raman Spectrum of Graphite," *J. Chem. Phys.* 53:1126.
Van der Ven et al. (1998) "First-Principles Evidence for Stage Ordering in $Li_xCoO_2$," *Journal of the Electrochemical Society.* 145(6):2149-2155.
Vicente et al. (2004) "Understanding the Voltage Profile of Li Insertion Into $LiNi_{0.5-y}Fe_yMn_{1.5}O_4$ in Li Cells," *Electrochimica Acta.* 49(12):1963-1967.
Vitins et al. (1997) "Lithium intercalation into layered $LiMnO_2$," *Journal of the Electrochemical Society.* 144(8) :2587-2592.
Wada et al. (1980) *J. Non-Cryst. Solids* 35:543.
Wagemaker et al. (2005) "Thermodynamics of Spinel $Li_xTiO_2$ from First Principles," *Chemical Physics.* 317(2-3):130-136.
Wakihara (2005) "Lithium Manganese Oxides with Spinel Structure and Their Cathode Properties for Lithium Ion Battery," *Electrochemistry.* 73(5):328-335.
Wang et al. (2004) "Enthalpy of Formation of $LiNiO_2$, $LiCoO_2$ and Their Solid Solutions $LiNi_{1-x}Co_xO_2$," *Solid State Ionics.* 166(1-2):167-173.
Wang et al. (2005) "$LiMO_2$ (M 32 Mn, Fe, and Co): Energetics, Polymorphism and Phase Transformation," *Journal of Solid State Chemistry.* 178(4):1230-1240.
Wang et al. (2007) "A First-Principles Approach to Studying the Thermal Stability of Oxide Cathode Materials," *Chemistry of Materials.* 19(3):543-552.
Xu et al. (2003) "Nanocrystalline Ferric Oxide Cathode for Rechargeable Lithium Batteries," *Electrochemical and Solid State Letters.* 6(9):A190-A193.
Yamaki et al. (2001) "Thermodynamics and Phase Separation of Lithium Intercalation Materials Used in Lithium Ion Cells," *Electrochemistry.* 69(9):664-669.
Yamaki et al. (2001) "Voltage Prediction from Coulomb Potential Created by Atoms of Spinel $LiMn_2O_4$ Cathode Active Material for Li Ion Cells," *Journal of Power Sources.* 97(8):349-353.
Yamaki et al. (2000) "Potential and Thermodynamics of Graphite Anodes in Li-Ion Cells," *Journal of the Electrochemical Society.* 147(2):460-465.
Yazami et al. (2006) "Thermodynamics and crystal structure anomalies in lithium-intercalated graphite," *J. Power Sources* 153:312-318.
Yazami et al. (Web Release Apr. 30, 2007) "Fluorinated Carbon Nanofibres for High Energy and High Power Densities Primary Lithium Batteries," Electrochem. Commun. 9:1850-1855.
Yazami, R. (Dec. 2009) "Thermodynamics of Electrode Materials for Lithium-Ion Batteries," In; Kazunori Ozawa Ed., Lithium Ion Rechargeable Batteries: Materials, Technology, and New Applications, Wiley-VCH Verlag GmbH and Co. CH. 5, pp. 67-101.
Zhou et al. (2006) "Configurational Electronic Entropy and the Phase Diagram of Mixed-Valence Oxides: The Case of $Li_xFeO_4$," *Physical Review Letters.* 97(15).
First Office Action issued Nov. 22, 2013, from the State Intellectual Property Office of China, for Chinese Patent Application No. 2011104273589 and Search Report.
First Office Action issued Jun. 28, 2012 from the State Intellectual Property Office of China for Chinese Patent Application No. 200680028690.5.
Second Office Action issued Mar. 11, 2013, from the State Intellectual Property Office of China for Chinese Patent Application No. 200680028690.5.
Notice of Reasons for Rejection corresponding to Japanese Patent Application No. P2008-525161, Dispatch Date May 21, 2013—includes English translation.
Notice of Reasons for Rejection corresponding to Japanese Patent Application No. P2008-525161, dispatched May 22, 2012 from the Japanese Patent Office—includes English translation.
Notice of Reasons for Rejection corresponding to Japanese Patent Application No. P2012-255415, dispatched Jan. 21, 2014—includes English translation.
First Office Action, Chinese Patent Application No. 2013800339457, May 20, 2016, 23 pages.

(56) References Cited

OTHER PUBLICATIONS

Supplementary European Search Report, European Application No. 06851120, completed Mar. 9, 2015, 6 pages.

* cited by examiner $$V_{out} = -RC \frac{dV_{in}}{dt}$$

| SOC (%) | OCV (V) | ΔS (JK$^{-1}$mole$^{-1}$) | ΔH (kJmole$^{-1}$) |
|---|---|---|---|
| 3 | 3.484 | 12.8 | -374.3 |
| 40 | 3.788 | -26.8 | -373.5 |
| 65 | 3.917 | -22.8 | -384.7 |
| 98 | 4.173 | -14.2 | -406.2 |

Figure 15

| Weeks 60°C | $Q_d$ (mAh) | CL (%) | <E> (V) | $\varepsilon_d$ (mWh) | SOH (%) |
|---|---|---|---|---|---|
| 0 | 43.07 | --- | 3.82 | 164 | 100 |
| 1 | 42.95 | 0.28 | 3.79 | 163 | 99.72 |
| 2 | 41.31 | 4.09 | 3.78 | 156 | 95.91 |
| 3 | 40.16 | 6.76 | 3.77 | 151 | 93.24 |
| 4 | 39.98 | 7.17 | 3.77 | 151 | 92.83 |
| 5 | 39.68 | 7.87 | 3.78 | 150 | 92.13 |
| 6 | 38.65 | 10.26 | 3.76 | 145 | 89.74 |
| 7 | 37.66 | 12.56 | 3.75 | 141 | 87.44 |
| 8 | 36.88 | 14.37 | 3.72 | 137 | 85.63 |

Figure 21A

| Weeks 70°C | $Q_d$ (mAh) | CL (%) | <E> (V) | $\varepsilon_d$ (mWh) | SOH (%) |
|---|---|---|---|---|---|
| 0 | 43.07 | 0 | 3.82 | 164 | 100 |
| 1 | 42.06 | 2.35 | 3.79 | 159 | 97.65 |
| 2 | 40.84 | 5.18 | 3.77 | 154 | 94.82 |
| 3 | 38.94 | 9.59 | 3.76 | 146 | 90.41 |
| 4 | 38.00 | 11.77 | 3.76 | 142 | 88.23 |
| 5 | 36.97 | 14.16 | 3.76 | 139 | 85.84 |
| 6 | 35.77 | 16.95 | 3.75 | 134 | 83.05 |
| 7 | 34.93 | 18.90 | 3.74 | 131 | 81.1 |
| 8 | 32.65 | 24.19 | 3.73 | 122 | 75.81 |

Figure 21B

| COV (V) | (mAh) | (%) | <> (V) | $\varepsilon_d$ (mWh) | SOH (%) |
|---|---|---|---|---|---|
| 4.2 | 43.07 | 0 | 3.82 | 164 | 100 |
| 4.3 | 42.51 | 1.30 | 3.81 | 162 | 98.7 |
| 4.4 | 41.44 | 3.78 | 3.80 | 157 | 96.13 |
| 4.5 | 40.62 | 5.69 | 3.78 | 153 | 94.32 |
| 4.6 | 38.09 | 11.56 | 3.77 | 143 | 88.44 |
| 4.7 | 37.35 | 13.28 | 3.76 | 140 | 82.72 |
| 4.8 | 36.16 | 16.04 | 3.77 | 136 | 83.96 |
| 4.9 | 34.90 | 18.97 | 3.62 | 126 | 81.03 |

Figure 29

| Cycle number | (mAh) | (%) | <> (V) | $\mathcal{E}_d$ (mWh) | SOH (%) |
|---|---|---|---|---|---|
| 1 | 36.58 | -- | 3.72 | 136 | 100 |
| 100 | 34.28 | 6.3 | 3.73 | 128 | 93.7 |
| 200 | 32.92 | 10 | 3.72 | 122 | 90 |
| 300 | 31.78 | 13.1 | 3.68 | 117 | 86.9 |
| 400 | 30.75 | 15.9 | 3.67 | 113 | 84.1 |
| 500 | 29.11 | 20.4 | 3.65 | 106 | 79.6 |
| 600 | 28.10 | 23.2 | 3.65 | 103 | 76.8 |
| 700 | 25.99 | 28.9 | 3.65 | 95 | 71.1 |
| 800 | 25.19 | 31.1 | 3.58 | 90 | 68.9 |
| 900 | 24.40 | 33.3 | 3.56 | 87 | 66.7 |
| 1000 | 23.55 | 35.62 | 3.54 | 83 | 64.38 |

Figure 33

IMBEDDED CHIP FOR BATTERY APPLICATIONS

CROSS REFERENCE TO RELATED APPLICATION

This application claims the benefit of and priority to U.S. provisional application 61/639,712, filed on Apr. 27, 2012, which is hereby incorporated by reference in its entirety.

BACKGROUND

Over the last few decades, significant advances have been made in electrochemical storage and conversion devices, expanding the capabilities of these systems in a variety of fields including portable electronic devices, air and space craft technologies, and biomedical devices. Current state of the art electrochemical storage and conversion devices tend to have designs and performance attributes specifically selected for compatibility with the diverse range of user applications. For example, current electrochemical storage systems span a range from light weight, stable batteries providing reliable, long runtimes to high capacity batteries capable of providing extremely high discharge rates. Despite recent advances, widespread development and demand for high power portable electronic products has created significant pressure for researchers to develop even more high performance batteries suitable for the wide range of these applications. Furthermore, demands of miniaturization in the field of consumer electronics and instrumentation continue to stimulate research into novel design and material strategies for reducing the sizes, weights and form factors of high performance batteries.

Many recent advances in electrochemical storage and conversion technology are directly attributable to discovery and integration of new materials for battery components. Lithium-ion battery technology, for example, continues to rapidly develop, at least in part, due to the integration of novel cathode and anode materials for these systems. From the pioneering discovery and optimization of intercalated carbon anode materials to more recent discoveries of nano-structured transition metal oxide intercalation cathode materials and nano-phosphate cathode materials, development of new materials has revolutionized the design and performance capabilities of primary and secondary lithium ion batteries. For example, advanced electrode materials have significantly enhanced the energy capacities, energy densities, discharge current rates and cycle life provided by these systems, thus positioning lithium ion batteries to be the preferred technology for the next generation of high-power portable electronic systems, hybrid electric car (HEV) and electric vehicles (EV). Advances in electrode materials also has great promise to positively impact other systems including electrochemical capacitors and supercapacitors, and fuel cells, and is likely to be critical to implementation of these technologies for a range of device applications. Accordingly, the identification and performance evaluation of novel electrode materials is currently a research priority in the development of new and improved electrochemical energy storage and conversion systems.

Electrochemical energy storage and conversion devices use two electrodes; an anode and a cathode, which are electrical conductors, separated by a purely ionic conductor, the electrolyte. The electric current generated during discharge results from chemical reactions and physical processes (e.g., transport) taking place at the electrodes' surfaces, in which positively or negatively charged ions are exchanged with the electrolyte. These processes, in turn, generate or absorb electrons so as to keep the electrical neutrality of the system. The charge exchange induces important modifications in the electrodes surface and bulk structures properties. In particular, charge transfer processes affect each electrode's potential and reaction rate, which set the energy and the power density outputs of an electrochemical power generating device. In the case of a rechargeable battery, for example, the mechanism(s) and extent of changes in the electrodes surface and bulk structure determine the cycle life under specific thermodynamic and kinetic operating conditions (e.g., temperature, charge and discharge voltage limits, current rates and so on).

Knowing the thermodynamics of electrode reactions and physical transformations is essential in predicting the performance and stability of any electrochemical storage and conversion system. For example, important thermodynamic state functions establish, at least in part, the energy, the power and the cycle life of an autonomous electrochemical power source. In fact, the energy density reflects the total amounts of charges reversibly exchanged and the potential at which the exchange occurs. On the other hand, cycle life relates to the stability of states or phases resulting from electrode transformations in the process of charge and discharge. All these processes are controlled, at least to a certain degree, by the thermodynamics of the electrode reactions.

A number of techniques have been developed and applied to evaluating the thermochemical kinetics of electrode reactions including electroanalytical methods (e.g., cyclic voltammetry, potentiometry etc.) and spectroscopic techniques (e.g. x-ray diffraction, NMR, LEEDs, etc.). Given the importance of thermodynamics in virtually all electrochemical energy storage and conversion systems, however, there is currently a need in the art for systems and methods for measuring key thermodynamic parameters, such as changes in entropy, enthalpy and Gibbs free energy, with the accuracy needed for predicting and optimizing the performance attributes and capabilities of these systems. Such systems would play a significant role in identifying new materials for the next generation of electrochemical energy storage and conversion systems, and would significantly contribute to enhancing understanding of the thermochemical kinetics of established cathode and anode materials. New thermodynamic analysis systems also have great potential as versatile test instruments for characterizing materials properties and performance in commercially manufactured electrode systems, including batteries and fuel cells.

SUMMARY

The present invention provides systems and methods for accurately characterizing thermodynamic and materials properties of electrodes and electrochemical energy storage and conversion systems. Systems and methods of the present invention are capable of simultaneously collecting a suite of measurements characterizing a plurality of interconnected electrochemical and thermodynamic parameters relating to the electrode reaction state of advancement, voltage and temperature. Enhanced sensitivity provided by the present methods and systems combined with measurement conditions that reflect or approximate thermodynamically stabilized electrode conditions allow very accurate measurement of thermodynamic parameters, including state functions such as the Gibbs free energy, enthalpy and entropy of electrode/electrochemical cell reactions, that enable prediction of important performance attributes of electrode materials and electrochemical systems, such as the energy, power density, current rate, state of health, state of safety and the cycle life of an electrochemical cell.

The present systems and methods also allow sensitive characterization of the composition, phase and materials properties important for design and performance of electrodes in electrochemical systems. The present methods enable identification and characterization of phase transitions, crystallite size, surface and bulk defects and crystal structure defects in electrode materials that dramatically impact the electrochemical properties of electrodes and the performance of electrochemical storage and conversion systems. For example, thermodynamic state functions can be measured by the present systems and methods with an accuracy that enables identification of major or small phase transformations, which may be difficult, if not impossible, to detect via conventional means such as x-ray diffractometry or simple open-circuit cell potential measurements. Some small transformations may be the onset or the prelude of more drastic ones, which upon prolonged cycling will affect the battery's energy, power and cycle life performances. Detection of such transformations and understanding their origin is crucial for optimized electrode materials design.

Systems and methods of the present invention are also applicable for characterizing a range of thermodynamic parameters useful for designing, testing and characterizing electrochemical cells, such as primary and secondary batteries and electrode materials, including but not limited to intercalating electrode materials. The capabilities of the present systems and methods, however, extend beyond batteries and encompass electrode reactions in other electrochemical devices/systems including fuel cells, EDLCs, gas electrodes, catalysis, corrosions, electro-deposition, and electro-synthesis, where the acquisition of thermodynamics data also provides important insights on the energetics of electrode reactions and device performance.

In one aspect, provided are devices for monitoring a condition of an electrochemical cell. A device of this aspect comprises an integrated circuit comprising a voltage monitoring circuit for measuring a plurality of open circuit voltages of an electrochemical cell, a temperature monitoring circuit for measuring a plurality of temperatures of the electrochemical cell, a current monitoring circuit for measuring a charging current or a discharging current of the electrochemical cell and a circuit for determining a thermodynamic parameter of the electrochemical cell. In embodiments, one or more of a plurality of open circuit voltages and a plurality of temperatures of the electrochemical cell are generated upon charging or discharging the electrochemical cell or upon stopping a charging or discharging of the electrochemical cell. Useful thermodynamic parameters include one or more of a change in entropy ($\Delta S$) of the electrochemical cell, a differential entropy (dS) of the electrochemical cell, a change in enthalpy ($\Delta H$) of the electrochemical cell, a differential enthalpy (dH) of the electrochemical cell and a change in free energy ($\Delta G$) of the electrochemical cell.

In embodiments, the circuit for determining a thermodynamic parameter is positioned in electrical or data communication with the temperature monitoring circuit to receive temperature measurements from the temperature monitoring circuit. In embodiments, the circuit for determining a thermodynamic parameter is positioned in electrical or data communication with the voltage monitoring circuit to receive open circuit voltage measurements from the voltage monitoring circuit. In embodiments, the circuit for determining a thermodynamic parameter is positioned in electrical or data communication with the current monitoring circuit to receive current measurements from the current monitoring circuit or to provide thermodynamics parameters to the current monitoring circuit.

Optionally, a device of this aspect is a component of an electrochemical cell or is imbedded in the electrochemical cell. Imbedded devices and battery systems of this nature are beneficial, for example, as they can be used as a self-analyzing battery, battery system or battery package or as a component of a larger system. Imbedded devices and battery systems also provide the benefit of the ability to quickly and efficiently diagnose and characterize individual cells within a multi-cell battery system, such as to diagnose and identify cells that are malfunctioning, improperly charging or discharging, unsafe, suitable for removal or replacement, or to characterize one or more cell's cycle number, state of health or state of safety. Optionally, electrochemical cells useful with the devices and methods described herein comprise two or more electrodes, such as a cathode, an anode and, optionally, one or more reference electrodes. Use of electrochemical cells comprising one or more reference electrodes, in embodiments, provides for directly determining a condition of each electrode individually.

In embodiments, devices of this aspect are positioned so that the device and any associated components are not corroded or degraded, for example by exposure to components of an electrochemical cell. Preventing corrosion and degradation is useful, for example, to provide for durability of the device and any associated components, such as printed circuit boards, resistors, capacitors, inductors and other circuit components. In embodiments, the device is mounted on a printed circuit board or, optionally, the device is mounted on a flexible circuit board. In certain embodiments, the device is mounted on a flexible circuit board that is wrapped at least partially around an electrochemical cell. Optionally, the device comprises one or more resistors, capacitors and inductors positioned in electrical communication with one or more components of the integrated circuit. In an exemplary embodiment, a device of this aspect is positioned in electrical communication with one or more of an anode and a cathode of an electrochemical cell, for example by one or more wires positioned to provide electrical communication between the device and the anode or cathode.

Optionally, devices of this aspect comprise a wireless transceiver circuit, for example positioned in data communication or electrical communication with one or more components of the device or of the integrated circuit. In a specific embodiment, a device of this aspect comprises one or more wireless transceivers providing data communication between components of the device, such as between one or more of the voltage monitoring circuit, the temperature monitoring circuit, the current monitoring circuit the circuit for determining a thermodynamic parameter and other circuits of the devices of this aspect. Including wireless transceivers in devices of this aspect provides, for example, for flexibility in the design and configuration of the devices.

In a specific embodiment, the device and optional circuit components, such as inductors, capacitors, resistors and external circuit components, are surface mount type components. In embodiments, the device and optional circuit components have a thickness of 5 mm or less, 3 mm or less or 2 mm or less. Optionally, the device is attached to an electrochemical cell between fabrication of the electrochemical cell and packaging of the electrochemical cell.

In one embodiment, for example, the device itself further comprises the electrochemical cell. In one embodiment, for example, the device is a component of a package comprising the device and one or more electrochemical cells, such as in a battery pack. In certain embodiments, the device is positioned in selective data communication, selective electrical communication, switchable data communication or switchable electrical communication with one or more electrochemical cells. In another embodiment, the device is positioned outside a housing of the electrochemical cell or outside a package comprising the electrochemical cell.

In embodiments, the integrated circuit of devices of this aspect comprises a circuit for determining an open circuit state of an electrochemical cell, for example a current monitoring circuit. Optionally, the integrated circuit comprises a power switching circuit and the power switching circuit optionally determines an open circuit state of the electrochemical cell. In a specific embodiment, the circuit for determining an open circuit state is configured to provide an indication, such as a data or voltage indication, to the voltage monitoring circuit to measure the open circuit voltage of the electrochemical cell when the electrochemical cell is in an open circuit voltage state or operating under open circuit voltage conditions. Optionally, the circuit for determining an open circuit state is configured to provide an indication to one or more of a voltage monitoring circuit, a temperature monitoring circuit and a current monitoring circuit to stop measuring an open circuit voltage, a temperature or a current of the electrochemical cell after a preselected time period. Optionally, the circuit for determining an open circuit state is configured to provide an indication to one or more of a voltage monitoring circuit, a temperature monitoring circuit and a current monitoring circuit to measure or re-measure an open circuit voltage, a temperature or a current of the electrochemical cell after a preselected time period. Thus, devices of this aspect optionally can detect when the cell is open circuit and then can measure the open circuit voltage immediately, thereby improving measurement accuracy and determining when the electrochemical cell or a device comprising the electrochemical cell is powered off or shut down and thereby disable devices of this aspect from draining energy from the electrochemical cell.

Optionally, devices of this aspect do not directly or actively control the temperature of the electrochemical cell. Devices which do not directly control the temperature of the electrochemical cell are useful, for example, to minimize the number of components and complexity of operation of the system. Devices which do not directly control the temperature of the electrochemical cell are beneficial as they do not require long times for establishing the temperature of an electrochemical cell, but can still efficiently characterize and analyze one or more conditions of the cell, such as a thermodynamic parameter, taking advantage of the changes in a temperature of the cell that occur during charging and discharging or which occur after charging or discharging is stopped as the cell temperature proceeds to the ambient temperature due to passive heat exchange between the cell and the air or environment. Advantages gained from not including a temperature controller and related components include, but are not limited to, minimizing the size of the device, minimizing the cost of the device, simplification of the complexity of the device. One benefit of the devices of this aspect that do not directly or actively control the temperature of the electrochemical cell is that they are capable of determining one or more thermodynamic parameters of an electrochemical cell, regardless of the ability to control the electrochemical cell temperature. An additional benefit of the devices of this aspect of the that do not directly or actively control the temperature of the electrochemical cell results from a reduced time for acquiring and processing an electrochemical cell's temperature, voltage, OCV, thermodynamic parameters, such as $\Delta S$ and $\Delta H$, and state of charge and state of health data. Such a reduction in acquisition and processing time is advantageous, for example, because the data can be collected more frequently and does not require the time necessary for waiting for the electrochemical cell's temperature to stabilize to the controlled temperature.

For example, in one embodiment, the device does not comprise a temperature controller or a means for controlling or establishing a temperature of the electrochemical cell, such as a heating element or an element that transfers heat into the electrochemical cell by conduction from an external heat source, or a cooling element, such as a thermoelectric cooler, a Peltier cooler or an element that actively transports heat out of the electrochemical cell by conduction to an external heat sink. In an embodiment, for example the device does not comprise a temperature controller or a means for actively controlling or establishing a temperature of the electrochemical cell. In an embodiment, for example the device does not comprise a temperature controller or a means for actively controlling or establishing a specified or selected temperature of the electrochemical cell.

In certain embodiments, however, an electrochemical cell comprises or is in thermal communication with one or more heat sinks, heat exchangers, liquid cooling or air cooling systems or heat pipes, even when a device of this aspect does not directly control the temperature of the electrochemical cell. Heat sinks, heat exchangers, liquid cooling or air cooling systems or heat pipes are optionally used to maintain the temperature of an electrochemical cell within a selected working range or to prevent the temperature of an electrochemical cell from rising beyond a specified, maximum, or rated temperature. Use of a heat sink, heat exchanger, liquid cooling or air cooling system or heat pipe permits more efficient heat transfer between an electrochemical cell and the environment than by passive transport of heat than if a heat sink, heat exchanger or heat pipe were not used. In certain embodiments, a heat sink or heat exchanger is positioned such that air is moved across the heat sink or heat exchanger to facilitate passive heat transport to the air or environment. Optionally, a liquid cooling or air cooling system or heat pipe is used to transport heat between an electrochemical cell and a heat sink or heat exchanger. In certain embodiments, a liquid cooling or air cooling system or heat pipe is positioned such that heat is transported using the liquid cooling or air cooling system or heat pipe to a remotely located heat sink or heat exchanger to facilitate passive heat transport to the air or environment.

Other useful temperature regulating systems include forced air cooling systems (e.g., fan driven systems), compressed air cooling systems and heat exchangers using high heat exchange surface areas and fast heat transfer materials, such as copper or aluminum. A heat exchanger optionally comprises a cooling fluid such as compressed air, cooled water, a phase transition heat absorbent or a heat transferring material such as a liquid metal or a molten salt.

Optionally, a device of this aspect further comprises a temperature sensor positioned in thermal communication with the electrochemical cell and also positioned in electrical or data communication with the temperature monitoring circuit. Optionally, the temperature monitoring circuit determines or monitors a temperature of the electrochemical cell as the electrochemical cell is charging or discharging. Optionally, the temperature monitoring circuit determines or monitors a temperature of the electrochemical cell when the electrochemical cell is not charging or when the electrochemical cell is not discharging. Useful temperature sensors include those comprising thermocouples, resistance thermometers and thermistors.

Optionally, a device of this aspect is a component of an automobile, such as an electric vehicle or a hybrid electric vehicle. Incorporation of devices of this aspect into automobiles is beneficial to permit monitoring and characterizing of the electrochemical cells used to drive an electric motor in an automobile. Optionally, in devices of this aspect that comprise a component of an automobile, the voltage monitoring circuit measures a plurality of open circuit voltages of the electrochemical cell when the automobile is idle, stopped, parked, powered off, powering off, powered on, powering on, accelerating or decelerating. Optionally, in devices of this aspect that comprise a component of an automobile, the temperature monitoring circuit measures a plurality of temperatures of the electrochemical cell when the automobile is idle, stopped, parked, powered off, powering off, powered on, powering on, accelerating or decelerating.

In embodiments, a change in open circuit voltage of the electrochemical cell occurs when the automobile is idle, stopped, parked, powered off, powering off, powered on, powering on, accelerating or decelerating. In embodiments, a change in temperature of the electrochemical cell occurs when the automobile is idle, stopped, parked, powered off, powering off, powered on or powering on off, powered on, powering on, accelerating or decelerating. Optionally, a plurality of temperatures of the electrochemical cell are measured during or after one or more of idling of the automobile, stopping the automobile, parking the automobile, powering off the automobile, powering on the automobile, accelerating the automobile, and decelerating the automobile. Optionally, a plurality of open circuit voltages of the electrochemical cell are measured during or after one or more of idling of the automobile, stopping the automobile, parking the automobile, powering off the automobile, powering on the automobile, accelerating the automobile, and decelerating the automobile.

Optionally, a device of this aspect is a component of a mobile or portable electronic device, such as a cell phone, a laptop computer, a tablet computer, an e-book reader, a portable music player, a portable audio player, a portable video player, a bar code reader, a telemetric reader, a portable light device, a portable sound or alarm device, a portable autonomous electric power devices, such as for military, telecommunications, aerospace and space applications, games, watches, clocks, portable medical devices, implantable medical devices. Optionally, a device of this aspect is a component of a stationary, though portable, electronic device, such as a gas detector, a smoke detector or an alarm system. Incorporation of devices of this aspect into mobile and portable electronic devices is beneficial to permit monitoring and characterizing of the electrochemical cells used to power the mobile or portable electronic device. Optionally, in devices of this aspect that comprise a component of a mobile or portable electronic device, the voltage monitoring circuit measures a plurality of open circuit voltages of the electrochemical cell when the portable electronic device is idle, powered off, powering off, powered on or powering on. Optionally, in devices of this aspect that comprise a component of a mobile or portable electronic device, the temperature monitoring circuit measures a plurality of temperatures of the electrochemical cell when the portable electronic device is idle, powered off, powering off, powered on or powering on.

In embodiments, a change in open circuit voltage of the electrochemical cell occurs when the portable electronic device is idle, powered off, powering off, powered on or powering on. In embodiments, a change in temperature of the electrochemical cell occurs when the portable electronic device is idle, powered off, powering off, powered on or powering on. Optionally, a plurality of temperatures of the electrochemical cell are measured during or after one or more of idling of the portable electronic device, powering off the portable electronic device and powering on the portable electronic device. Optionally, a plurality of open circuit voltages of the electrochemical cell are measured during or after one or more of idling of the portable electronic device, powering off the portable electronic device and powering on the portable electronic device.

Optionally, a device of this aspect is a component of a battery backup system, such as an uninterruptable power supply. Optionally, a device of this aspect is a component of a stationary energy storage system or facility, such as those attached to photovoltaic, wind, geothermal, hydraulic and tide energy generating systems and generally for electric power plants. Incorporation of devices of this aspect into these and other systems is beneficial to permit monitoring and characterizing of the electrochemical cells used in battery backup systems, load leveling systems and peak shaving systems.

In embodiments, devices of this aspect are useful determining a thermodynamic parameter of the electrochemical cell. In a specific embodiment, the thermodynamic parameter of the electrochemical cell is determined using one or more of the plurality of open circuit voltages of the electrochemical cell the plurality of temperatures of the electrochemical cell. For example, in an embodiment, a change in free energy of the electrochemical cell is determined by measuring an open circuit voltage of the electrochemical cell. In an embodiment, for example, a change in enthalpy of the electrochemical cell is determined by measuring an open circuit voltage of the electrochemical cell at a plurality of temperatures. Optionally, a change in enthalpy of the electrochemical cell is determined by computing an intercept of a linear regression of open circuit voltage measurements of the electrochemical cell versus temperature measurements of the electrochemical cell. In an embodiment, for example, a change in entropy of the electrochemical cell is determined by measuring an open circuit voltage of the electrochemical cell at a plurality of temperatures. Optionally, a change in entropy of the electrochemical cell is determined by computing a slope of a linear regression of open circuit voltage measurements of the electrochemical cell versus temperature measurements of the electrochemical cell.

In embodiments, different temperatures of the electrochemical cell are achieved through the temperature changes that naturally occur through use of the electrochemical cell, for example by charging or discharging. In embodiments, the temperature of an electrochemical cell increases as the electrochemical cell is charged or discharged. Conversely, in embodiments, the temperature of an electrochemical cell decreases after charging or discharging of the electrochemical cell stops. Such natural temperature changes are used by the devices and methods of the present invention for determining one or more thermodynamic parameters.

Although it may not uniformly be the case for all electrochemical cell chemistries, in embodiments, the open circuit voltage for an electrochemical cell increases as the temperature of the electrochemical cell increases or decreases as the temperature of the electrochemical cell decreases. In many embodiments, the open circuit voltage of an electrochemical cell changes as the electrochemical cell is charged or discharged. In some embodiments, the open circuit voltage of an electrochemical cell changes after charging or discharging of the electrochemical cell stops.

In embodiments, a thermodynamic parameter of the electrochemical cell is determined using a first temperature of the electrochemical cell and a second temperature of the electrochemical cell different from the first temperature of the electrochemical cell. Optionally, a thermodynamic parameter of the electrochemical cell is determined using a first temperature of the electrochemical cell and a second temperature of the electrochemical cell after the electrochemical cell is heated by charging or discharging. Optionally, a thermodynamic parameter of the electrochemical cell is determined using a first temperature of the electrochemical cell and a second temperature of the electrochemical cell after the electrochemical cell cools from the first temperature.

In embodiments, a thermodynamic parameter of the electrochemical cell is determined using a first open circuit voltage of the electrochemical cell and a second open circuit voltage of the electrochemical cell different from the first open circuit voltage of the electrochemical cell. For example, a thermodynamic parameter of the electrochemical cell is optionally determined using a first open circuit voltage of the electrochemical cell and a second open circuit voltage of the electrochemical cell after the electrochemical cell is charged or discharged. For example, a thermodynamic parameter of the electrochemical cell is optionally determined using a first open circuit voltage of the electrochemical cell after charging or discharging of the electrochemical cell is stopped and a second open circuit voltage of the electrochemical cell while charging or discharging of the electrochemical cell remains stopped and after the temperature of the electrochemical cell changes.

Optionally, for a device of this aspect, the integrated circuit further comprises a state of charge calculating circuit for determining a state of charge of the electrochemical cell. In embodiments, a state of charge calculating circuit comprises a current measuring circuit. Monitoring, calculating and determination of the state of charge of an electrochemical cell can be useful, in embodiments, for determination of one or more conditions of the electrochemical cell. For example, a state of health, charge cycle, or a state of safety can optionally be determined through a plurality of measurements or determinations of electrochemical cell state of charge. In some embodiments, the state of health, charge cycle or state of safety of the electrochemical cell is determined by comparing a state of charge of the electrochemical cell with one or more thermodynamic parameters of the electrochemical cell or by computing a linear or other regression of the state of charge of the electrochemical cell versus one or more thermodynamic parameters of the electrochemical cell. In embodiments, a plurality of states of charge of the electrochemical cell are generated upon charging or discharging the electrochemical cell. In embodiments, the circuit for determining a thermodynamic parameter is positioned in electrical or data communication with the state of charge calculating circuit to receive state of charge measurements from the state of charge calculating circuit or to provide thermodynamic parameters to the state of charge calculating circuit.

In embodiments, the state of charge of the electrochemical cell refers to a ratio of a first value to a second value. In one specific embodiment, the first value is a net amount of charge remaining in the electrochemical cell and the second value is a rated charge capacity of the electrochemical cell or a theoretical charge capacity of the electrochemical cell. In another specific embodiment, the first value is a net amount of charge required to charge the electrochemical cell to a rated charge capacity of the electrochemical cell or to a theoretical charge capacity of the electrochemical cell and the second value is the rated charge capacity of the electrochemical cell or the theoretical charge capacity of the electrochemical cell.

In one embodiment, a state of charge calculating circuit determines a coulometric state of charge of an electrochemical cell, for example, based on current measurements received from a current measuring circuit. In an embodiment, a state of charge calculating circuit determines a true state of charge of an electrochemical cell based on thermodynamic parameters received by the state of charge calculating circuit. Optionally, the true state of charge of the electrochemical cell is determined by looking up received thermodynamic parameters in a look up table or interpolating between points in a look up table. In a specific embodiment, the integrated circuit of devices of this aspect monitors an electrochemical cell as it is charged under controlled conditions and the integrated circuit updates entries in a look up table as the electrochemical cell is charged. For example, during charging of an electrochemical cell under controlled conditions, entries in the lookup table, such as states of charge, open circuit voltages and thermodynamic parameters are updated.

Devices of this aspect include voltage monitoring circuits for measuring, determining and/or estimating an open circuit voltage of an electrochemical cell. Measurements or estimates of an open circuit voltage of an electrochemical cell are useful for a variety of purposes, including determining a condition of an electrochemical cell, such as a thermodynamic parameter of the electrochemical cell, a state of charge of the electrochemical cell, a state of health of the electrochemical cell, a state of safety of the electrochemical cell and a cycle number of the electrochemical cell. In embodiments, open circuit voltage measurements or estimates provide insight into the electrochemical cell's usage, safety, health, duration, durability and remaining life. In embodiments, open circuit voltage measurements or estimates provide insight into the physical construction and or distribution of materials and components within an electrochemical cell, such as to indicate a phase or components of the electrochemical cell, a composition of components of the electrochemical cell, or an event or condition taking place within the electrochemical cell.

In embodiments, a device of this aspect measures or monitors an open circuit voltage of an electrochemical cell, for example, using the voltage monitoring circuit. Optionally, the voltage monitoring circuit determines an open circuit voltage of the electrochemical cell when the electrochemical cell is not charging or when the electrochemical cell is not discharging. Optionally, the voltage monitoring circuit determines an open circuit voltage of the electrochemical cell after a charging or discharging of the electrochemical cell is stopped. Optionally, the voltage monitoring circuit determines an open circuit voltage of the electrochemical cell for thermochemically stabilized conditions of the electrochemical cell. Optionally, the voltage monitoring circuit determines an open circuit voltage of the electrochemical cell for non-thermochemically stabilized conditions of the electrochemical cell.

In certain embodiments, it may require significant time for an electrochemical cell to relax to thermochemically stabilized conditions, for example a time period longer than one second, longer than ten seconds, longer than thirty seconds, etc. Devices of this aspect are capable of estimating an open circuit voltage of an electrochemical cell for thermochemically stabilized conditions by monitoring changes in the open circuit voltage of the electrochemical cell as the electrochemical cell relaxes towards thermochemically stabilized conditions over a shorter time period than required for the electrochemical cell to fully relax to a thermochemically stabilized condition. For example, in some embodiments, the relaxation of open circuit voltage follows an exponential decay towards the open circuit voltage corresponding to thermochemically stabilized conditions. Monitoring the open circuit voltage and computing the exponential decay time constant thereby permits calculation of the asymptotic open circuit voltage corresponding to thermochemically stabilized conditions. In an embodiment, the voltage monitoring circuit determines or estimates an open circuit voltage of the electrochemical cell for thermochemically stabilized conditions of the electrochemical cell based on the open circuit voltage of the electrochemical cell for the non-thermochemically stabilized conditions of the electrochemical cell. This latter embodiment is useful, for example, for situations where it takes time for the electrochemical cell to relax to thermochemically stabilized conditions.

Optionally, devices of this aspect are useful for monitoring one or more conditions of an electrochemical cell, for example, a thermodynamic parameter, a state of health, a state of safety and a cycle number of the electrochemical cell. Monitoring one or more of these conditions permits, for example, detailed information about the electrochemical cell's usage, safety, health, duration, durability and remaining life. Such monitoring, for example, facilitates replacement of failing or aging electrochemical cells, as well as warning of imminent failure or degraded performance of an electrochemical cell, thereby preventing catastrophic failure of an electrochemical cell or a system drawing power from the electrochemical cell.

In a specific embodiment, the integrated circuit of a device of this aspect is configured to monitor a condition of one or more electrochemical cells, wherein the condition is one or more of a thermodynamic parameter, a state of health, a state of safety and a cycle number. In an embodiment, the circuit for determining a thermodynamic parameter of the electrochemical cell further determines one or more of a state of health of the electrochemical cell, a state of safety of the electrochemical cell and a cycle number of the electrochemical cell.

Optionally, the integrated circuit further comprises an additional circuit for determining one or more of a state of health of the electrochemical cell, a state of safety of the electrochemical cell and a cycle number of the electrochemical cell. Optionally, a device of this aspect further comprises an additional circuit for determining one or more of a state of health of the electrochemical cell, a state of safety of the electrochemical cell and a cycle number of the electrochemical cell, for example as a component external to the integrated circuit.

Useful conditions for monitoring of electrochemical cells include, but are not limited to, a thermodynamic parameter of the electrochemical cell, a state of charge of the electrochemical cell, a state of health of the electrochemical cell, a state of safety of the electrochemical cell and a cycle number of the electrochemical cell. In embodiments, the state of health of the electrochemical cell refers to the amount of energy (W·h) and power (W) deliverable or available in a system compared to the best, ideal, theoretical or rated amounts when the system is newly fabricated and tested, such as at 100% state of charge. In embodiments, battery state of health decays or reductions result from electrode and electrolyte materials degradation, from an increase in internal resistance and from mechanical and chemical effects, such as hardware deformation due to heat, gazing and corrosion. In embodiments, a metric for state of health assessment is the relative peak power fade at a specified or defined state of charge, such as expressed by $SOH=100(P(SOC)/P_0(SOC))$, where, SOH refers to the state of health of the electrochemical cell, $P(SOC)$ is the peak power at a state of charge (SOC) of an aged cell and $P_0(SOC)$ is the peak power at a state of charge of a freshly manufactured and tested cell at the same state of charge (SOC); optionally a state of charge of 50% is used in determination of SOH, though other states of charge are optionally used as well. The following references, hereby incorporated by reference, disclose methods for estimating, calculating or measuring a state of health of an electrochemical cell: Ng et al., Applied Energy 86 (2009) 1506-1511; Remmlinger et al., J. Power Sources 196 (2011) 5357-5363; Andre et al., Engineering Applications of Artificial Intelligence 26 (2013) 951-961; Lin et al., IEEE Transactions on Industrial Informatics, 9:2 (2013) 679-685; Eddahech et al., Electrical Power and Energy Systems 42 (2012) 487-494.

In embodiments, the state of safety (SOS) of the electrochemical cell refers to the likelihood or probability of the electrochemical cell to undergo a thermal runaway. In embodiments, one useful metric for determination of SOS is the onset temperature of a thermal event within the electrochemical cell at a defined state of charge. In embodiments, the lower the onset temperature, such as that measured by a thermal analysis method including calorimetric methods, differential thermal analysis (DTA) methods and differential scanning calorimetric methods (DSC), the higher the thermal runaway risk and thus the lower the SOS. In embodiments, the cycle number of the electrochemical cell refers to a number of charge or discharge cycles the electrochemical cell has experienced, for example the number of full charge or discharge cycles, the number of partial charge or discharge cycles or combinations thereof.

In embodiments, devices of this aspect analyze a history of one or more electrochemical cells in order to determine a state of health or a state of safety of the electrochemical cell. Useful histories of electrochemical cells include, but are not limited to, as an open circuit voltage history, a temperature history, a state of charge history, a thermodynamic parameter history, a cycle number history. As used herein, the term "history" refers to previous measurements, estimates or analyses of conditions or events of an electrochemical cell made over a time period. In embodiments, a state of health of an electrochemical cell is determined by measurement of a peak power of the electrochemical cell, such as at a specified state of health. In one embodiment, the electrochemical cell under consideration is brought to a defined state of charge and discharged at a fast increasing power (P=UI, U=voltage, I=current). Optionally, peak power is defined as the highest power the cell can sustain for a short period of time, for example over a fraction of a second to a few seconds. In embodiments, a peak power measurement is not reversible and may itself adversely affect the cell's state of health. In embodiments, a state of safety of an electrochemical cell is determined through calorimetric methods, such as differential scanning calorimetry (DSC) and accelerated rate calorimetry (ARC), by determining a temperature one set, total heat and self-heating rates of processes within an electrochemical cell at a defined initial state of charge.

In a specific embodiment, a device of this aspect determines an entropy, a change in entropy or a differential entropy of the electrochemical cell and compares the determined entropy, change in entropy or differential entropy with a reference entropy, a reference change in entropy or a reference differential entropy and disables charging or discharging of the electrochemical cell when the determined entropy, change in entropy, or differential entropy is different from the reference entropy, reference change in entropy or reference differential entropy. In embodiments, the reference entropy, reference change in entropy or reference differential entropy is an entropy, change in entropy or differential entropy of a reference electrochemical cell, such as an electrochemical cell having a preselected state of charge, a preselected state of safety, a preselected state of health or any combination of these. In embodiments, the electrochemical cell is disabled from charging or discharging when the determined entropy, change in entropy, or differential entropy is greater than the reference entropy, reference change in entropy or reference differential entropy or less than the reference entropy, reference change in entropy or reference differential entropy. In an embodiment, a device of this aspect determines a temperature of the electrochemical cell and compares the determined temperature with a reference temperature and disables charging or discharging said electrochemical cell when the determined temperature is greater than the reference temperature.

In embodiments, devices of this aspect comprise one or more integrated circuits or one or more integrated circuit components. For example, in one embodiment, the integrated circuit comprises a field programmable gate array. In an embodiment, for example, the integrated circuit comprises an application-specific integrated circuit. Optionally, a circuit component of an integrated circuit comprises a field programmable gate array or an application-specific circuit. For example, in embodiments, a circuit for determining a thermodynamic parameter of the electrochemical cell comprises a field programmable gate array or an application-specific integrated circuit.

In another aspect, the present invention provides methods, including methods of determining a condition of an electrochemical cell and methods of determining a parameter of an electrochemical cell. In embodiments, methods of this aspect provide ways for determining states of health of an electrochemical cell, for determining a state of charge of an electrochemical cell, determining a state of safety of an electrochemical cell, for determining states of safety of an electrochemical cell, for determining a cycle number of an electrochemical cell, determining a composition of an electrochemical cell, determining a change in a phase of one or more components of an electrochemical cell, and for determining a thermodynamic parameter of an electrochemical cell, such as a change in entropy ($\Delta S$), a change in enthalpy ($\Delta H$) and a change in free energy ($\Delta G$).

In an embodiment, a method of this aspect comprises the steps of: providing an integrated circuit comprising: a voltage monitoring circuit for measuring a plurality of open circuit voltages of the electrochemical cell, the plurality of open circuit voltages generated upon charging or discharging the electrochemical cell or stopping charging or discharging the electrochemical cell, a temperature monitoring circuit for measuring a plurality of temperatures of the electrochemical cell, the plurality of temperatures generated upon charging or discharging the electrochemical cell or stopping charging or discharging the electrochemical cell, and a circuit for determining a thermodynamic parameter of the electrochemical cell, wherein the thermodynamic parameter is one or more of a change in entropy of the electrochemical cell, a change in enthalpy of the electrochemical cell and a change in free energy of the electrochemical cell, the circuit for determining a thermodynamic parameter positioned in electrical or data communication with the temperature monitoring circuit to receive temperature measurements from the temperature monitoring circuit and positioned in electrical or data communication with the voltage monitoring circuit to receive open circuit voltage measurements from the voltage monitoring circuit; generating the plurality of open circuit voltages of the electrochemical cell, the plurality of temperatures of the electrochemical cell or both the plurality of open circuit voltages of the electrochemical cell and the plurality of temperatures of the electrochemical cell; and determining a first thermodynamic parameter of the electrochemical cell using the integrated circuit.

Optionally, a generating step of a method of this aspect comprises charging or discharging the electrochemical cell. Optionally, one or more of a temperature of the electrochemical cell and an open circuit voltage of the electrochemical cell changes during the charging or discharging. In this way, embodiments of this aspect can utilize the natural temperature and open circuit voltage changes associated with charging or discharging the electrochemical cell for determination of a parameter or condition of the electrochemical cell.

Optionally, a generating step of a method of this aspect comprises stopping a charging or a discharging of the electrochemical cell. Optionally, one or more of a temperature of the electrochemical cell and an open circuit voltage of the electrochemical cell changes after stopping the charging or the discharging. Here, embodiments of this aspect can utilize the natural changes in temperature and open circuit voltage that occur as an electrochemical cell relaxes back towards ambient temperature after being heated during charging or discharging for determination of a parameter or condition of the electrochemical cell.

In embodiments, methods of this aspect further comprise a step of comparing the first thermodynamic parameter with one or more reference thermodynamic parameters for a reference electrochemical cell. In a specific embodiment, a cell chemistry of the reference electrochemical cell is identical to a cell chemistry of the electrochemical cell. In embodiments, methods comprising steps of comparing thermodynamic parameters are useful, for example, because they permit thorough characterization of an reference electrochemical cell under carefully controlled conditions in order to provide useful reference measurements for later comparison with an electrochemical cell as it is being used, for example in an automotive or portable electronic device application. By comparing a thermodynamic parameter measured for an electrochemical cell as it is being used with reference thermodynamic parameters for a reference electrochemical cell, insights into a condition of the electrochemical cell can be obtained. For example, method embodiments incorporating comparison of thermodynamic parameters permit estimation or determination of an electrochemical cell's state of health, state of safety, cycle number, and other characteristics of cell aging.

In one embodiment, for example, the step of determining a first thermodynamic parameter comprises determining a change in entropy for the electrochemical cell at a first open circuit voltage. Optionally, a method of this aspect further comprises a step of determining a second thermodynamic parameter of the electrochemical cell using the integrated circuit. Optionally, a method of this aspect further comprises a step of comparing the second thermodynamic parameter with one or more reference thermodynamic parameters for a reference electrochemical cell. In an embodiment, for example, the step of determining a second thermodynamic parameter comprises determining a change in entropy for the electrochemical cell at a second open circuit voltage.

Optionally, a step of comparing the first thermodynamic parameter with one or more reference thermodynamic parameters comprises interpolating between points in an array of reference thermodynamic parameters or in a look-up table of reference thermodynamic parameters. As described above, useful reference thermodynamic parameters or in a look-up table of reference thermodynamic parameters include values determined for a reference electrochemical cell. In an embodiment, the step of comparing the first thermodynamic parameter with one or more reference thermodynamic parameters comprises determining a condition of the electrochemical cell based on the comparison.

In an exemplary embodiment, the step of determining a first thermodynamic parameter of the electrochemical cell comprises the steps of: charging or discharging the electrochemical cell to a first open circuit voltage value; stopping the charging or discharging; measuring open circuit voltages of the electrochemical cell as a function of time using the integrated circuit; and measuring temperatures of the electrochemical cell as a function of time using the integrated circuit. Optionally, the step of determining a first thermodynamic parameter for the electrochemical cell further comprises computing a linear regression of open circuit voltage measurements versus temperature measurements. In an embodiment, the measured open circuit voltages of the electrochemical cell provide values for changes in free energy of the electrochemical cell, wherein an intercept of the linear regression provides values for changes in enthalpy of the electrochemical cell and wherein a slope of the linear regression provides values for changes in entropy of the electrochemical cell.

As described previously with reference to devices of the invention, some method embodiments do not comprise controlling a temperature of the electrochemical cell using a temperature controller, a heater, a cooler or any combination of these.

In embodiments, another method of this aspect comprises the steps of: providing a reference array of values comprising thermodynamic parameter values for a reference electrochemical and cell condition values for the reference electrochemical cell; determining a thermodynamic parameter for the electrochemical cell; and determining the condition of the electrochemical cell using the reference array of values, wherein the condition of the electrochemical cell corresponds to a cell condition of the reference electrochemical cell for a reference thermodynamic value equal to the determined thermodynamic parameter for the electrochemical cell.

Optionally, the array of values further comprises open circuit voltage values for the reference electrochemical cell, as described above. In a specific embodiment, the array of values comprises two or more open circuit voltage values, a plurality of thermodynamic parameter values for each of the two or more open circuit voltage values and one or more cell condition values for each of the two or more open circuit voltage values and the plurality of thermodynamic parameter values. Optionally, the step of determining the condition of the electrochemical cell comprises interpolating between values of the array of values.

In embodiments, methods of this aspect advantageously determine one or more conditions of an electrochemical cell including a state of health of the electrochemical cell, a state of charge of the electrochemical cell, a state of safety of the electrochemical cell and a cycle number of the electrochemical cell. In a specific embodiment, cell condition values in an array of values comprises one or more of a state of health of the reference electrochemical cell, a state of charge of the reference electrochemical cell, a state of safety of the reference electrochemical cell and a cycle number of the reference electrochemical cell. Optionally, the array of values comprises values for changes in entropy of the reference electrochemical cell at two or more open circuit voltages.

In specific embodiments, the thermodynamic parameter values for an electrochemical cell, such as a reference electrochemical cell, are obtained by a method comprising the steps of: controlling a composition of the reference electrochemical cell to establish a plurality of reference electrochemical cell compositions; controlling a temperature of the reference electrochemical cell to establish a plurality of electrochemical cell compositions for each of the plurality of reference electrochemical cell compositions; measuring open circuit voltages of the reference electrochemical cell for each of the plurality of reference electrochemical cell compositions and the reference electrochemical cell temperatures. Such methods are useful, as described above, for carefully and thoroughly characterizing an electrochemical cell, such as a reference electrochemical cell, and particularly for developing multiple arrays of values for a variety of electrochemical cell chemistries. Optionally, the thermodynamic parameter values for an electrochemical cell, such as a reference electrochemical cell, are obtained by a method further comprising a step of computing a linear regression of open circuit voltage measurements of the reference electrochemical cell versus temperature measurements of the reference electrochemical cell. Optionally, the measured open circuit voltages of the electrochemical cell provide values for changes in free energy of the electrochemical cell, wherein an intercept of the linear regression provides values for changes in enthalpy of the electrochemical cell and wherein a slope of the linear regression provides values for changes in entropy of the electrochemical cell.

In a specific embodiment, the step of determining a thermodynamic parameter for the electrochemical cell comprises the steps of: charging or discharging the electrochemical cell to a first open circuit voltage value; stopping the charging or discharging; measuring open circuit voltages of the electrochemical cell as a function of time; and measuring temperatures of the electrochemical cell as a function of time. Optionally, the step of determining a thermodynamic parameter for the electrochemical cell further comprises computing a linear regression of open circuit voltage measurements of the electrochemical cell versus temperature measurements of the electrochemical cell. Optionally, the measured open circuit voltages of the electrochemical cell provide values for changes in free energy of the electrochemical cell, wherein an intercept of the linear regression provides values for changes in enthalpy of the electrochemical cell and wherein a slope of the linear regression provides values for changes in entropy of the electrochemical cell.

In an exemplary embodiment, the step of determining a thermodynamic parameter for the electrochemical cell is performed using an integrated circuit comprising: a voltage monitoring circuit for measuring a plurality of open circuit voltages of the electrochemical cell, the plurality of open circuit voltages generated upon charging or discharging the electrochemical cell or stopping charging or discharging the electrochemical cell; a temperature monitoring circuit for measuring a plurality of temperatures of the electrochemical cell, the plurality of temperatures generated upon charging or discharging the electrochemical cell or stopping charging or discharging the electrochemical cell; and a circuit for determining a thermodynamic parameter of the electrochemical cell, wherein the thermodynamic parameter is one or more of a change in entropy of the electrochemical cell, a change in enthalpy of the electrochemical cell and a change in free energy of the electrochemical cell, the circuit for determining a thermodynamic parameter positioned in electrical or data communication with the temperature monitoring circuit to receive temperature measurements from the temperature monitoring circuit and positioned in electrical or data communication with the voltage monitoring circuit to receive open circuit voltage measurements from the voltage monitoring circuit.

In a specific embodiment, the step of determining a thermodynamic parameter for the electrochemical cell does not comprise controlling a temperature of the electrochemical cell using a temperature controller, a heater, a cooler or any combination of these. Optionally, the step of determining a thermodynamic parameter for the electrochemical cell comprises generating a plurality of open circuit voltages of the electrochemical cell, a plurality of temperatures of the electrochemical cell or both a plurality of open circuit voltages of the electrochemical cell and a plurality of temperatures of the electrochemical cell.

Optionally, the generating step comprises charging or discharging the electrochemical cell; wherein a temperature of the electrochemical cell changes during the charging or discharging, wherein an open circuit voltage of the electrochemical cell changes during the charging or discharging or wherein both a temperature of the electrochemical cell and an open circuit voltage of the electrochemical cell change during the charging or discharging. Optionally, the generating step comprises stopping a charging or a discharging of the electrochemical cell; wherein a temperature of the electrochemical cell changes after stopping the charging or the discharging, wherein an open circuit voltage of the electrochemical cell changes after stopping the charging or the discharging or wherein both a temperature of the electrochemical cell and an open circuit voltage of the electrochemical cell change after stopping the charging or the discharging.

In another aspect provided are methods for safely operating an electrochemical cell. A specific embodiment of this aspect comprises the steps of: providing an electrochemical cell; providing an entropy monitoring circuit for monitoring an entropy of the electrochemical cell, the circuit positioned in electrical communication with the electrochemical cell; determining an entropy of the electrochemical cell using the entropy monitoring circuit; comparing the determined entropy of the electrochemical cell with a reference entropy; and disabling the electrochemical cell from charging or discharging when the determined entropy of the electrochemical cell is different from the reference entropy. In embodiments, methods of this aspect provide for safe operation and monitoring of electrochemical cells, such as to prevent electrochemical cells from operating under conditions in which thermal runaway of the electrochemical cell is likely to take place. In embodiments, methods of this aspect provide a way to disable or bypass electrochemical cells which are determined to be unfit for safe operation, thereby preventing further increasing the likelihood that the electrochemical cell will undergo thermal runaway.

Optionally, the reference entropy is an entropy of a reference electrochemical cell having a preselected state of safety, a preselected state of charge, a preselected state of health or any combination of these, such as a reference electrochemical cell that is approaching the end of its useful life and should be removed from operation to prevent unsafe conditions. In a specific embodiment, the disabling step comprises actuating a switch, relay or transistor in electrical communication with an electrode of the electrochemical cell, thereby disabling charging or discharging the electrochemical cell. Optionally, the determining step comprises determining a change in entropy of the electrochemical cell. Optionally, the comparing step comprises comparing the change in entropy of the electrochemical cell with a reference change in entropy. Optionally, the disabling step comprises disabling the electrochemical cell from charging or discharging when the determined change in entropy of the electrochemical cell is greater than the reference change in entropy. Optionally, the determining step comprises determining a differential entropy of the electrochemical cell. Optionally, the comparing step comprises comparing the differential entropy of the electrochemical cell with a reference differential entropy. Optionally, the disabling step comprises disabling the electrochemical cell from charging or discharging when the determined differential entropy of the electrochemical cell is greater than the reference differential entropy. In a specific embodiment, the step disabling step disables the electrochemical cell from charging or discharging with the determined entropy is greater than the reference entropy or less than the reference entropy.

In another embodiment, a method of this aspect further comprises the steps of: monitoring a temperature of the electrochemical cell; comparing the temperature of the electrochemical cell with a reference temperature; and disabling the electrochemical cell from charging or discharging when the temperature of the electrochemical cell is greater than the reference temperature. Optionally, these embodiments provide another means for ensuring safe operation of an electrochemical cell or for determining whether an electrochemical cell has begun thermal runaway or will later undergo thermal runaway if the cell is continued in operation. Optionally, the reference temperature is a temperature of a reference electrochemical cell having a preselected state of safety, a preselected state of charge, a preselected state of health or any combination of these. Optionally, the disabling step comprises actuating a switch, relay or transistor in electrical communication with an electrode of the electrochemical cell, thereby disabling charging or discharging the electrochemical cell.

In an exemplary embodiment, methods of this aspect utilize devices described herein for monitoring an entropy of an electrochemical cell. In a specific embodiment, the entropy monitoring circuit comprises an integrated circuit comprising: a voltage monitoring circuit for measuring a plurality of open circuit voltages of the electrochemical cell, the plurality of open circuit voltages generated upon charging or discharging the electrochemical cell or stopping charging or discharging the electrochemical cell; a temperature monitoring circuit for measuring a plurality of temperatures of the electrochemical cell, the plurality of temperatures generated upon charging or discharging the electrochemical cell or stopping charging or discharging the electrochemical cell; a current monitoring circuit for measuring a charging current of the electrochemical cell or a discharging current of the electrochemical cell; and a circuit for determining a thermodynamic parameter of the electrochemical cell, wherein the thermodynamic parameter is one or more of a change in entropy of the electrochemical cell, a change in enthalpy of the electrochemical cell and a change in free energy of the electrochemical cell, the circuit for determining a thermodynamic parameter positioned in electrical or data communication with the temperature monitoring circuit to receive temperature measurements from the temperature monitoring circuit, positioned in electrical or data communication with the voltage monitoring circuit to receive open circuit voltage measurements from the voltage monitoring circuit and positioned in electrical or data communication with the current monitoring circuit to receive current measurements from the current monitoring circuit or to provide thermodynamics parameters to the current monitoring circuit.

In the context of this description, the term "thermodynamically stabilized conditions" refers to experimental conditions wherein measured open circuit voltages approximate equilibrium cell voltage such that the measurements can be used to determine thermodynamic parameters and materials properties with accuracies such that these parameters may be used to evaluate the electrochemical, materials and performance attributes of the electrodes and/or electrochemical cell. Measurement of open circuit voltages for thermodynamically stabilized conditions enables determination of state functions such as the Gibbs free energy, enthalpy and entropy of electrode/electrochemical cell reactions. It is intended that thermodynamically stabilized conditions include some deviations from absolute equilibrium conditions. In some embodiments open circuit voltages for thermodynamically stabilized conditions deviate from true equilibrium voltages by less than 1 mV and preferably, for some embodiments, conditions deviate from true equilibrium voltages by less than 0.1 mV. Under some experimental conditions of the present invention, the open circuit voltages are nearly an exact measure of the difference in Gibbs free energy of Li in the anode and cathode and any observed deviations originate from limitations in the measurement techniques employed during analysis. The ability to accurately identify open circuit voltage measurements reflecting thermodynamically stabilized conditions is useful for providing measurements of open circuit voltage, temperature and composition that may be used for characterization of important thermodynamic, electrochemical and materials properties of the electrodes analyzed.

In some embodiments, the expression "electrochemical cell" refers to a device comprising of three major active materials:

anode: is typically the electrode where an oxidation takes place. Oxidation is a loss of electron and can be schematized as: $R_a \rightarrow O_a + n_a e$, wherein $R_a$ is the reduced form and $O_a$ is the oxidized form of a chemical specie or used for the anode material. It comprises a neutral or positively charged (cation) or negatively charged (anion), $n_a$=number of electron moles exchanged in the anode reaction per $R_a$ mole. The anode is the negative pole of the cell during discharge;

cathode: is typically the electrode where a reduction (electron gain) takes place. The reaction is the reverse of the previous one, i.e. $O_c + n_c e \rightarrow R_c$, wherein $O_c$ is the oxidized form and $R_c$ is the reduced form of a chemical specie or used for the cathode material. It comprises a neutral or positively charged (cation) or negatively charged (anion), $n_c$=number of electron moles exchanged in the anode reaction per $O_c$ mole. The cathode is the positive pole of the cell during discharge; and electrolyte: is an ionically conductive material, which role is to provide anions and cations needed for the electrode reactions to be achieved. It usually comprises a solvent medium and a solute material such as a salt, an acid or a base. In some cases, the electrolyte changes composition a result of the cell's charge and discharge (see, lead-acid batteries for example where sulfuric acid is consumed during discharge: $Pb + PbO_2 + 2H_2SO_4 \rightarrow 2PbSO_4 + 2H_2O$)

As used herein, the expressions "electrochemical cell composition" or "composition of an electrochemical cell" are used synonymously and refer to compositions and/or physical states of active materials comprising the electrochemical cell (i.e., electrodes such as cathode and anode, and the electrolyte). Accordingly, in some embodiments electrochemical cell composition refers to surface and/or bulk compositions of cathode and anode materials, the composition of the electrolyte or any combination of these). In some embodiments of the present invention, the expression "composition of an electrochemical cell" refers to the state of charge of the electrochemical cell or any component thereof (e.g. active material such as electrodes or electrolyte).

Examples of electrochemical cells useful in the present invention include, but are not limited to, batteries (primary and secondary) and fuel cells. While the above anode and cathode reactions are characteristic of electrode processes in batteries and fuel cells and involve electron transfer between the electrolyte and the electrode in a so called faradaic process (or Redox process), there are other non-faradaic processes that allow for electrical charges storage at the electrode surface without a charge transfer or a Redox process.

Examples of electrochemical cells useful in the present invention include, but are not limited to, electrochemical double layer capacitors (EDLC) and electrochemical double layer supercapacitors. In an electrochemical double layer capacitor EDLC (or supercapacitor), an anion $A^-$ or a cation $C^+$ is stored on the electrode surface owing to accumulation of electrons ($e^-$) or electron holes ($h^+$) at the electrode-electrolyte interface to balance the adsorbed charge species and form neutral species in a double layer structure: $(A^-, h^+)$ and $(C^+, e^-)$. During charge and discharge the anions and/or cations are adsorbed or desorbed from the surface, which causes an electric current flow in the external circuit (charger or load) to balance for surface charges.

Hybrid supercapacitors are an intermediary category of electrical power sources between batteries and EDLC. They are hybrid because they combine two electrodes, one is a faradaic electrode like in a battery, and the other is a non-faradaic (capacitive) electrode like in an EDLC.

Batteries, fuel cells and EDLC are polarized systems in that the voltage of the anode and the cathode are different. During discharge, the cathode has the higher voltage $V^+$, therefore it is the positive pole, whereas the anode bears the lower voltage $V^-$ and is the negative pole. The difference in voltage $U = V^+ - V^-$ depends on different parameters, the most important are:

State of charge: (SOC) of each electrode. SOC is usually given in % of the total charge theoretically stored in the anode ($Q_{th}(an)$) or the cathode ($Q_{th}(ca)$; Density of discharge current (i): Under zero current, $U_{i=0}$ is the open-circuit voltage, which with time tends to an equilibrium value $U_\infty$ fixed by SOC and temperature; Temperature; State of health (SOH) of the system components: for anode, cathode and electrolyte the SOH varies with the system 'history', such as for the most common charge/discharge cycles, overcharge and overdischarge and thermal aging. Since a battery, a fuel cell and an EDLC function in a 'series' mode, any degradation of one of the active components: anode, cathode and electrolyte, will affect the cell's SOH.

With changing SOC, the electrodes surface or bulk composition changes and in some cases the electrolyte composition changes too. These changes in electrode surface and/or bulk composition and/or electrolyte composition establish, at least in part, the composition of the electrochemical cell (i.e. electrochemical cell composition) as described herein. Change in electrode composition is especially relevant for battery systems wherein electrolyte is consumed (e.g., lead acid, NiCd and Zn-silver batteries (See: reactions below)) and in normal or hybrid EDLCs.

A. Reactions for lead acid battery

Negative Electrode:

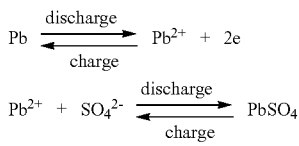

Positive Electrode:

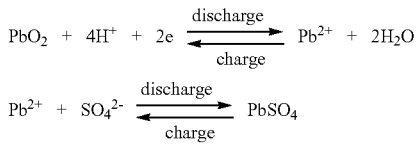

Overall Reaction:

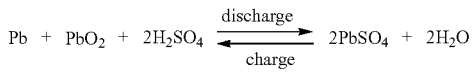

B. Reactions for nickel-cadmium system

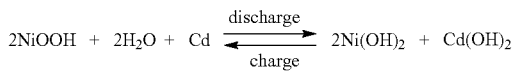

C. Reactions for silver-zinc, silver-cadmium and silver-iron systems

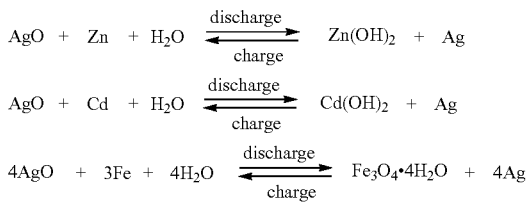

The present measurement system is capable of measuring thermodynamic functions of a half- or a full-cell at different SOC of the anode, cathode and electrolyte.

As used herein the expression "composition of an electrochemical cell" refers generally to bulk compositions and/or surface compositions of components of an electrochemical cell. In some embodiments, composition of an electrochemical cell refers to the composition of electrodes of the electrochemical cell, such as compositions of electrodes (e.g., cathode and/or anode electrodes) of the electrochemical cell. In embodiments wherein the electrode(s) is an intercalating electrode, the composition of an electrochemical cell may refer to the stoichiometry of the intercalating electrode materials with respect to the amount of intercalant physically associated with the electrode, the absolute amount of intercalant physically associated with the electrode, or the concentration of intercalant physically associated with the electrode. In some embodiments, the expression "composition of the electrochemical cell" refers to the composition of the electrolyte (e.g., the concentration(s) of components (ionic and/or nonionic) of the electrolyte). In some useful embodiments of the present invention, the expression "composition of an electrochemical cell" refers to the state of charge of the electrochemical cell or any component thereof, such as the state of charge of an electrode (cathode, anode, working, counter etc.) or combination of electrodes.

Coulometry is a technique useful in the present invention for measuring and/or selecting the electrochemical cell composition by establishing and/or determining the SOC of an electrochemical cell. In some embodiments, therefore, the composition controller comprises a coulometer. For example, let i(t) be the current intensity in the cell at time 't'. The total amount of charge Q(t) at time τ is given by the time integration of i(t):

$$Q(\tau) = \int_0^\tau i(t)dt \qquad (1)$$

The SOC of anode (an), cathode (cat) and electrolyte (elec) is given in % as:

$$SOC(an, cat, elec.) = 100 \frac{Q(t)}{Q_{th}(an, cat, elec.)} \qquad (2)$$

The SOC of the full cell is fixed by that of the limiting component, anode, cathode or electrolyte:

$$SOC(\text{full cell}) = \inf(SOC(an), SOC(cat), SOC(elec)) \qquad (3)$$

(the 'inf' function refers to the lowest value of a group of parameters). The electrochemical techniques for acquiring i(t) include, but are not limited to, the following:

Galvanostatic method: here the applied current or current density is constant i(t)=I. The amount of electricity passed is therefore proportional to time: Q(t)=It. Usually the electrode or cell voltage is plotted versus time, a technique called chronopotentiometry.

Constant voltage: applying a constant voltage different from the thermodynamic OCV will cause a current i(t) to flow in the cell. The latter is recorded versus time, a technique called chronoamperometry. A variant of this method is the 'voltage step' method, where a series of voltage steps $U_n$ (n=step number) are applied usually with a constant increment δU ($U_n=U_0\pm n$ δU). At each step, the current is recorded and integrated.

Potentio-dynamic methods such as linear sweep voltammetry and cyclic voltammetry: in this method the voltage is driven between two limit values $U_{up}$ and $U_{low}$ at a constant pace (U(t)=Uo±kt, k=constant, $U_{low}$<U(t)<$U_{up}$). The current response i(t) is recorded and generally plotted against U(t).

Discharge under constant load: the cell is connected to a resistance and the current is recorded versus time.

By proper selection of the compositions, design and/or experimental conditions of the electrochemical cell, the measurement system of the present invention can probe the materials properties, SOH, thermodynamics and/or materials properties of a single component of the electrochemical cell, such as a selected electrode (cathode or anode) or the electrolyte, and chemical reactions occurring on or in a single component of the electrochemical cell. Selection of such electrochemical cell and measurement system configurations are beneficial for using the present measuring system to generate useful information (thermodynamic, composition, physical properties etc.) relating to a single active component of an electrochemical cell and chemical reactions thereof. For example, by choice of an electrochemical cell having a first electrode (e.g. counter electrode) having a chemical potential that is independent of the state of charge of the electrochemical cell, the system of the present invention is capable of generating measurements of open circuit voltage for thermodynamically stabilized conditions for different compositions and/or states of charge of the second electrode (e.g. working electrode). In one embodiment, for example, use of a first electrode (e.g. counter electrode) comprising a pure electrode material (e.g., a lithium, cadmium or zinc pure metal electrode) is useful for providing open circuit voltage measurements that principally reflect the state of charge, composition and/or chemical reactions of the second electrode (e.g. working electrode). More generally, however, systems of the present invention employing a reference electrode (i.e., a third electrode), in addition to first and second electrodes, may be used to provide measurements of open circuit voltage or thermodynamic parameters, for example, as a function of the composition and/or state of charge (SOC) of a selected electrode (e.g., cathode or anode). In these embodiments, the incorporation of a reference electrode (i.e. a third electrode), therefore, allows accurate measurements of open circuit voltage for thermodynamically stabilized conditions for different compositions, temperatures and chemical reactions of a selected electrode of the electrochemical cell. Use of such system configurations is highly beneficial for providing thermodynamic and other useful information that principally reflects the chemistry, physical properties, thermodynamics and structure of a single electrochemical cell component. For example, use of a reference electrode or selection of an electrode having a chemical potential that is independent of the state of charge of the electrochemical cell allows thermodynamic state functions ($\Delta H$, $\Delta S$ and $\Delta G$) to be determined that correspond to a single electrode reaction. Such information is useful for the structural, thermodynamic and chemical characterization of electrochemical cell components, and may serve the basis for testing and quality control methods for evaluating components of electrochemical cells.

Open circuit voltage analyzers and voltage monitoring circuits of the present invention are capable of determining open circuit voltages, for example, that correspond to thermodynamically stabilized conditions or approximately thermodynamically stabilized conditions. In some embodiments, an open circuit voltage analyzer or voltage monitoring circuit is also capable of open circuit voltage data acquisition and, of optionally providing analysis of the data generated by the measurement system including calculating thermodynamic state functions, such as changes in entropy and enthalpy, and generating plots of thermodynamic state functions versus open circuit voltage or electrochemical cell composition useful for characterizing electrochemical cells and electrode materials. Useful open circuit analyzers and voltage monitoring circuits include, but are not limited to, those comprising processors capable of executing algorithms that utilize open circuit measurements as a function of time to identify open circuit voltages that correspond to thermodynamically stabilized conditions or approximately thermodynamically stabilized conditions. In an embodiment, an open circuit voltage analyzer or voltage monitoring circuit is capable of calculating observed rates of change in open circuit voltage per unit time ($\Delta OCV/\Delta t)_{observed}$ for electrochemical cell as a function of time. For example, an open circuit voltage analyzer or voltage monitoring circuit is optionally configured such that it directly or indirectly monitors open circuit voltage and calculates observed rates of change in open circuit voltage per unit time. For each observed rate of change in open circuit voltage per unit time, the absolute value of the observed rates of change in open circuit voltage per unit time is optionally compared to a threshold rate of change in open circuit voltage per unit time ($\Delta OCV/\Delta t)_{threshold}$. An open circuit voltage analyzer or voltage monitoring circuit determines that an open circuit voltage is equal to the open circuit voltage of the electrochemical cell for thermochemically stabilized conditions for the selected electrochemical cell temperature and composition combination when the absolute value of the observed rate of change in open circuit voltage per unit time is equal to or less than the threshold rate of change in open circuit voltage per unit time:

$$\left| \left( \frac{\Delta OCV}{\Delta t} \right)_{observed} \right| \leq \left( \frac{\Delta OCV}{\Delta t} \right)_{Threshold}.$$

In exemplary embodiments, the threshold rate of change in open circuit voltage as a function of time is equal to or less than 1 mV h$^{-1}$ (millivolt per hour) and preferably for some applications the threshold rate of change in open circuit voltage as a function of time is equal to or less than 0.3 mV h$^{-1}$, and more preferably for some applications the threshold rate of change in open circuit voltage as a function of time is equal to or less than 0.1 mV h$^{-1}$.

Optionally, an open circuit voltage analyzer or voltage monitoring circuit monitors the open circuit voltage of an electrochemical cell for a set period of time, for example a time period smaller than that required for the electrochemical cell to relax to thermochemically stabilized conditions. The open circuit voltage analyzer or voltage monitoring circuit then determines an exponential or other growth or decay rate in order to compute the open circuit voltage for thermochemically stabilized conditions from the growth or decay rate and a measured open circuit voltage for non-thermochemically stabilized conditions. Such a process permits determination of an open circuit voltage for thermochemically stabilized conditions even though thermochemically stabilized conditions are not directly measured, for example by extrapolating the open circuit voltage trend without having to wait for equilibrium values to be reached. For example, in one embodiment, a mathematical model is used for determination of equilibrium values by extrapolation. D. M. Bernardi et al., J. Power Sources 196 (2011) 412-427, herein incorporated by reference in its entirety, provides example methods for determination of equilibrium values by extrapolation In one embodiment, for example, the open circuit voltage analyzer, voltage monitoring circuit or other system component measures open circuit voltages at various times and uses this information to repeatedly (periodically or aperiodically) calculate observed rates of change in open circuit voltage per unit time. When the observed rate of change ($\Delta OCV/\Delta t)_{observed}$ calculated is equal to or less than the threshold rate of change ($\Delta OCV/\Delta t)_{threshold}$, the open circuit voltage analyzer or voltage monitoring circuit may determine that the most recent open circuit voltage measurement is equal to the open circuit voltage for thermochemically stabilized conditions, may determine the next open circuit voltage to be measured is equal to the open circuit voltage for thermochemically stabilized conditions, or may calculate a time averaged valued of open circuit voltage corresponding to experimental conditions when $|(\Delta OCV/\Delta t)_{observed}| \leq (\Delta OCV/\Delta t)_{threshold}$.

A significant capability of the present system is that it provides a means of establishing electrochemical cell conditions and collecting voltage, time and temperature measurements with the enhanced accuracy required to enable accurate thermodynamic analysis. Selection of a combination of a means for measuring open circuit voltage accurate to within about 1 mV and a temperature sensor capable of sensing electrochemical cell temperatures to within about 0.1 degrees Kelvin, for example, provides a number of benefits. For example, this combination of system component performance attributes provides measurements accurate enough to determine a range of important thermodynamic parameters and materials properties of many electrode materials and/or electrochemical energy conversion and storage systems. Further, these performance attributes enable thermodynamic state functions, such as the Gibbs free energy, enthalpy and entropy of electrode/electrochemical cell reactions, to be determined using measurements corresponding to a relatively narrow range of temperatures (e.g. less than or equal to about 10 degrees Kelvin). For some applications, confining measurements to a narrow range of electrochemical cell temperatures is beneficial for avoiding thermally activated phase changes in electrode materials that make thermodynamic analysis difficult and for avoiding electrochemical cell temperatures where self-discharge of the electrochemical cell is significant.

Methods of the present invention may further comprise a number of analysis steps wherein measurements of open circuit voltage, electrochemical cell composition, time and/or temperature are used to characterize thermodynamics and materials properties of the electrodes, electrolyte and/or electrochemical cell and/or to predict electrochemical performance parameters for these systems such as energy, energy density, power density, current rate, discharge voltage, capacity and the cycle life.

One method of the present invention, for example, further comprises analysis steps of generating plots or computing a linear regression of the open circuit voltages of the electrochemical cell versus temperature. In this embodiment, determination of slopes and intercepts for each of the plots or regressions corresponds to measured changes in entropy ($\Delta S$) and enthalpy ($\Delta H$), respectively, for reactions at the electrodes for each of the cell compositions. Analysis steps of this aspect of the present invention may further comprise calculating changes in Gibbs free energy ($\Delta G$) for reactions at the electrodes for each of the cell compositions using the determined entropy and enthalpy data.

A method of the present invention, for example, further comprises analysis steps of: (i) generating a plot of measured changes in entropy ($\Delta S$) versus electrochemical cell composition and/or (ii) generating a plot of measured changes in enthalpy ($\Delta H$) versus electrochemical cell composition; (iii) generating a plot of measured changes in entropy ($\Delta S$) versus open circuit voltage and (iv) generating a plot of changes in entropy ($\Delta S$) versus changes in enthalpy ($\Delta H$). Features in such plots of $\Delta S$ or $\Delta H$ versus electrochemical cell composition or open circuit voltage are useful for characterizing phase (and changes in phase), morphology and/or structural defects in electrode materials. Furthermore, such parametric entropy and enthalpy curves can be used as a 'fingerprint' for characterizing and/or identifying an electrode (e.g., cathode and an anode) material, an electrolyte and/or an electrochemical cell. As the material cycles in the battery, these traces change due to physical and/or chemical changes occurring in the electrode materials. The present methods, therefore, are useful for evaluating the 'state of health' of an electrode material upon heavy cycling or exposing to high temperatures or to overpotentials (overcharge and overdischarge for a cathode and an anode, respectively) or to provide quality control information regarding the presence of defects in electrodes and electrochemical systems.

Even when the composition of the electrode material is not well known, it is still very useful to plot the $\Delta S$ versus the OCV or electrochemical cell composition to ascertain the materials properties of the electrodes. The $\Delta S$ and the $\Delta H$ are functions of the chemical composition of the electrode material, and parametric plots of $\Delta S$ and $\Delta H$ versus open circuit voltage or composition is very sensitive to differences in the composition and structures of different materials. Accordingly, these parametric plots can serve as a "fingerprinting" for different materials so as to ascertain the identity, composition, structure, defect structure etc. of electrode materials, even when composition is not well known in advance.

Thermodynamic measuring methods and systems of the present invention enable a broad range of functionalities. In embodiments, methods of the present invention comprise a method of predicting one or more performance parameter of an electrode and/or electrochemical cell including the capacity, specific energy, power, cycle life, cell voltage, stability, self-discharge or discharge current of the electrochemical cell. In embodiments, methods of the present invention comprise a method of assessing the composition, morphology, phase or physical state of an electrode(s) or electrochemical cell. In embodiments, methods of the present invention comprise a method of identifying surface, bulk and crystal defect structures in electrode materials or electrochemical cell. In embodiments, methods of the present invention comprise a method of identifying a phase transition in electrode materials.

In one aspect, the SOH of a battery is related to the SOH of one (or a combination) of three major cell components: anode, cathode and electrolyte. The thermodynamic functions ($\Delta G$, $\Delta S$ and $\Delta H$) of each electrode reaction are used as the fingerprint of the corresponding electrode's SOH. These functions can be plotted versus the 'electrode composition' or the 'electrode Potential' to provide a quantitative characterization of the electrochemical cell or any component thereof.

The present invention also provides methods for determining the SOH of an electrochemical cell, for example an electrochemical cell comprising a host material. An embodiment of this aspect comprises the steps of: determining a $\Delta G$, $\Delta S$ and/or $\Delta H$ of the electrochemical cell for a plurality of selected electrochemical cell compositions; determining states of charge of the electrochemical cell for each of the plurality of selected electrochemical cell compositions; identifying the states of charge and $\Delta G$, $\Delta S$ and/or $\Delta H$ corresponding to an event or condition of the electrochemical cell; and comparing the $\Delta G$, $\Delta S$ and/or $\Delta H$ corresponding to the event or condition of the electrochemical cell to reference $\Delta G$, $\Delta S$ and/or $\Delta H$ corresponding to the event or condition of a reference electrochemical cell.

In specific embodiments, the event or condition includes, but is not limited to: a 0% charge state of the electrochemical cell, a 100% charge state of the electrochemical cell, one or more specific partial charge states of the electrochemical cell and a phase transition taking place within the electrochemical cell. For certain embodiments, the selected electrochemical cell compositions correspond to compositions of an electrode of the electrochemical cell, compositions of an electrolyte of the electrochemical cell and/or compositions or more than one electrode of the electrochemical cell. In an exemplary embodiment, the reference $\Delta G$, $\Delta S$ and/or $\Delta H$ are $\Delta G$, $\Delta S$ and/or $\Delta H$ for the electrochemical cell at a previous charge cycle.

The methods and systems of the present invention also are capable of thermodynamically evaluating virtually any electrochemical system having an electrode pair including, but not limited to, gas electrodes, electrochemical sensors, catalysis materials, corrosion systems, electro-deposition systems and electrosynthesis systems.

The methods and systems of the present invention also are capable of thermodynamically evaluating and otherwise analyzing virtually any type of electrode or any electrode material including, but not limited to, host electrode materials and intercalating electrode materials such as carbon electrodes, nanostructure metal oxide electrodes and nanophosphate electrodes.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

BRIEF DESCRIPTION OF THE DRAWINGS

FIG. 15 provides a summary of the analysis results of FIGS. 11-14.

FIGS. 21A and 21B provide a summary of the discharge characteristics after aging at 60° C. and 70° C., respectively.

FIG. 29 summarizes the discharge characteristics after overcharging cells to different cut-off voltages.

FIG. 33 provides a summary of discharge characteristics of cells after cycling for a specified number of cycles.

DETAILED DESCRIPTION

Figure 1:
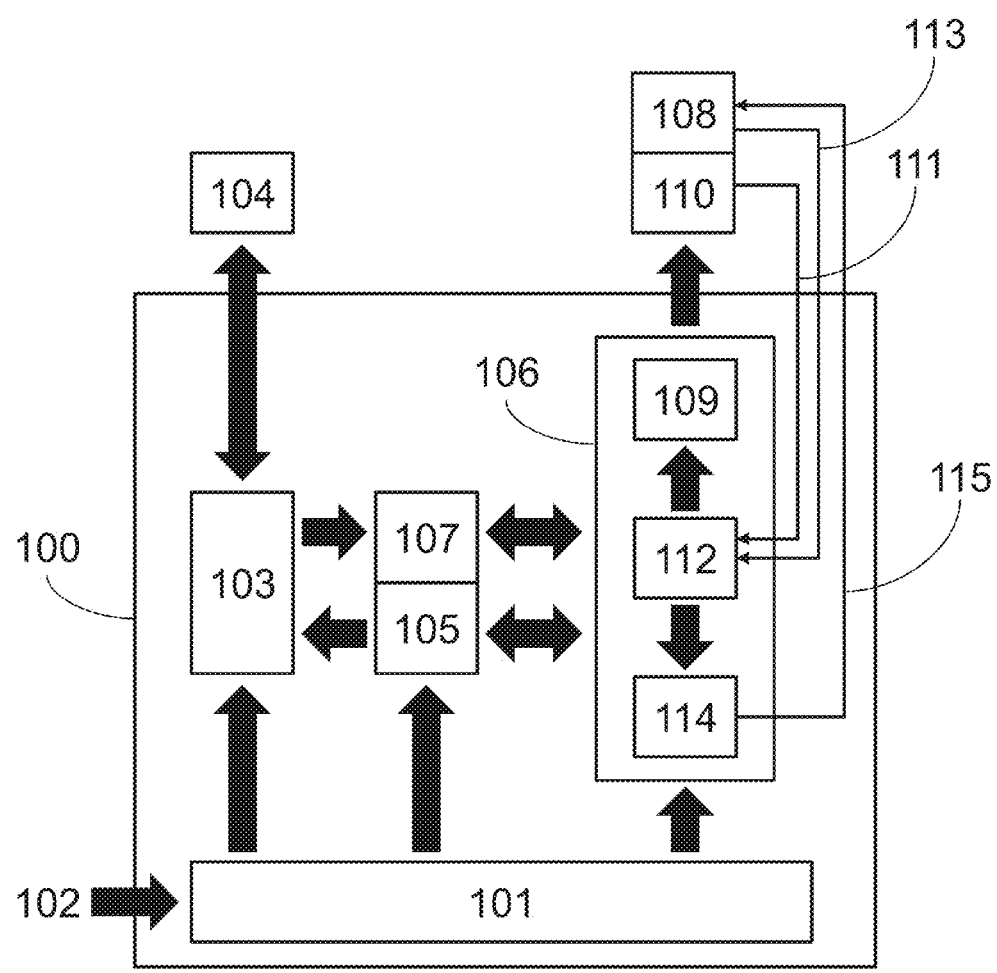
FIG. 1 provides a block diagram of an electrochemical thermodynamic measurement system (ETMS).

In general the terms and phrases used herein have their art-recognized meaning, which can be found by reference to standard texts, journal references and contexts known to those skilled in the art. The following definitions are provided to clarify their specific use in the context of the invention.

The term "electrochemical cell" refers to devices and/or device components that convert chemical energy into electrical energy or electrical energy into chemical energy. Electrochemical cells typically have two or more electrodes (e.g., cathode and anode) wherein electrode reactions occurring at the electrode surfaces result in charge transfer processes. Electrochemical cells include, but are not limited to, primary batteries, secondary batteries, galvanic cells, fuel cells and photovoltaic cells.

The term "open circuit voltage" refers to the difference in potential between terminals (i.e. electrodes) of an electrochemical cell when the circuit is open (i.e. no load conditions). Under certain conditions the open circuit voltage can be used to estimate the composition of an electrochemical cell. The present methods and system utilize measurements of open circuit voltage for thermochemically stabilized conditions of an electrochemical cell to determine thermodynamic parameters, materials properties and electrochemical properties of electrodes, electrochemical cells and electrochemical systems.

The term "capacity" is a characteristic of an electrochemical cell that refers to the total amount of electrical charge an electrochemical cell, such as a battery, is able to hold. Capacity is typically expressed in units of ampere-hours.

The expression "state of charge" or "SOC" is a characteristic of an electrochemical cell or component thereof (e.g. electrode—cathode and/or anode) referring to its available capacity, such as a battery, expressed as a percentage of its rated or theoretical capacity. The expression "state of charge" can optionally refer to a true state of charge or a coulometric state of charge. The state of charge of an electrochemical cell can be measured using a variety of methods, including those described herein. The following references, hereby incorporated by reference, disclose methods for estimating, calculating or measuring a state of charge of an electrochemical cell: Ng et al., Applied Energy 86 (2009) 1506-1511; Piller et al., J. Power Sources 96 (2001) 113-120; Coleman et al., IEEE Trans. Ind. Electron. 54 (2007) 2250-2257; Ng et al., "An enhanced coulomb counting method for estimating state-of-charge and state-of-health of lead-acid batteries," $INTELEC$ 31st, Incheon, K R, 2009; Snihir et al., J. Power Sources 159:2 (2006) 1484-1487;

The term "host material" refers to a component of an electrochemical cell configured for accommodating a molecule, atom, ion and/or group into the host material. In this context, accommodating includes insertion of a molecule, atom, ion and/or group into the host material, intercalation of a molecule, atom, ion and/or group into the host material and/or reaction of a molecule, atom, ion and/or group with the host material. In embodiments, accommodation of a molecule, atom, ion and/or group is a reversible process, such that a molecule, atom, ion and/or group can be released from the accommodating host material. For certain embodiments, reversible accommodation by host materials does not result in significant degradation or significant structural deformation of the material upon multiple accommodation/release cycles. In some embodiments a host material is an intercalation material. In some embodiments a host material is a framework material. In some embodiments a host material is a host electrode of an electrochemical cell and/or an intercalation electrode of an electrochemical cell.

"Intercalation" refers to refers to the process wherein an ion inserts into a host material to generate an intercalation compound via a host/guest solid state redox reaction involving electrochemical charge transfer processes coupled with insertion of mobile guest ions, such as fluoride ions. Major structural features of the host material are preserved after insertion of the guest ions via intercalation. In some host materials, intercalation refers to a process wherein guest ions are taken up with interlayer gaps (e.g., galleries) of a layered host material. Examples of intercalation compounds include, but are not limited to, fluoride ion intercalation compounds wherein fluoride ions are inserted into a host material, such as a layered fluoride host material or carbon host material.

"Embed" or "imbed" interchangeably refer to the arrangement of a first device or device component with relation to a second device or device component such that the two devices or device components are included within a common housing. In one embodiment, a device is embedded within a second device when they are packaged together. In a certain embodiment, a device is embedded within a second device when the devices are inextricably inseparable, or only separable by destroying or disassembling one of the devices.

"Thermal communication" refers to the arrangement of two or more devices or device components such that heat energy can efficiently flow between the devices or device components, either directly or indirectly by means of an intervening component or material. In some embodiments, two devices positioned in thermal communication are positioned in physical contact. In some embodiments, two devices positioned in thermal communication have an intermediate material positioned between them, such as a material that is an efficient conductor of heat, such as comprising aluminum or copper. In one embodiment, two devices or device components that are positioned in thermal communication have the same temperature.

"Electrical communication" refers to the arrangement of two or more devices or device components such that electrons can efficiently flow between the devices or device components. In an embodiment, two devices positioned in electrical communication are positioned in physical contact. In an embodiment, two devices positioned in electrical communication are positioned such that an electrical conductor is positioned between them, such as a copper wire or other metallic wire or conductor. "Switchable electrical communication" refers to the arrangement of two or more devices or device components such that the flow of electrons between two or more devices can be selectively terminated, for example using a switch. In one embodiment, three or more devices are in switchable electrical communication when, at any one time, only two of the three or more devices are in electrical communication with one another. In one embodiment, three or more devices are in switchable electrical communication when one device may be selectively placed into electrical communication with any one or more of the other two or more devices. In one embodiment, two or more devices are in switchable electrical communication when one device may be selectively placed into electrical communication with any one or more of the other devices.

"Data communication" refers to the arrangement of two or more devices or device components such that data can be transmitted between the devices or device component. Data communication includes one way and two way data transport. Data communication may be wired or wireless. In an embodiment, two devices or device components in data communication are in electrical communication. "Switchable data communication" refers to the arrangement of two or more devices or device components such that the transmission of data between two or more devices can be selectively terminated. In one embodiment, three or more devices are in switchable data communication when, at any one time, only two of the three or more devices are in data communication with one another. In one embodiment, two or more devices are in switchable data communication when one device may be selectively placed into data communication with any one or more of the other devices.

"Temperature sensor" refers to a device used to provide a signal indicative of a temperature of an object. In embodiments, a temperature sensor provides a voltage or a resistance to indicate the temperature of an object.

"Current monitoring circuit" refers to a circuit which receives a current and provides an indication of a magnitude or direction of current flow through the current monitoring circuit. In embodiments, an indication provided by a current monitoring circuit is a data indication, a visual indication or an electrical indication, such as a voltage indication or a current indication. In embodiments, a current monitoring circuit monitors a current from an electrochemical cell, for example a charging current or a discharging current. In embodiments, a current monitoring circuit continuously or periodically monitors a current.

"Circuit for determining an open circuit state" refer to a circuit which monitors whether or not an electrochemical cell is operating under open circuit voltage conditions. In embodiments, a circuit for determining an open circuit state comprises a current monitoring circuit. In embodiments, a circuit for determining an open circuit state comprises a power switching circuit.

"Open circuit state" refers to a configuration of an electrochemical cell providing a measure of whether the electrochemical cell is operating under open circuit voltage conditions. In embodiments, an electrochemical cell is operating under open circuit voltage conditions when a current flowing into or from the electrochemical cell is zero or is below a specified threshold value.

"Temperature monitoring circuit" refers to a circuit which receives a signal indicative of an object's temperature and calculates, derives, computes or otherwise determines or measures the object's temperature. In embodiments, a temperature monitoring circuit continuously monitors an object's temperature. In embodiments, a temperature monitoring circuit periodically monitors an object's temperature.

"Voltage monitoring circuit" refers to a circuit which receives a signal voltage from another object or device. In embodiments, a voltage monitoring circuit continuously monitors a voltage. In embodiments, a voltage monitoring circuit periodically monitors a voltage.

A "circuit for determining a thermodynamic parameter" refers to a circuit which computes, derives, calculates or otherwise determines or measures a thermodynamic state function or a change in a thermodynamic state function, including, but not limited to, the thermodynamic state functions of Enthalpy (H), Entropy (S) and Gibbs Free Energy (G). In embodiments, a circuit for determining a thermodynamic parameter determines a change in a thermodynamic state function from measurements of an electrochemical cell's open circuit voltage, temperature, composition and/or state of charge.

A "temperature controller" and a "means for controlling or establishing a temperature" refer to a device having the ability to actively establish and control its own temperature or a temperature of a device it is in thermal communication with or a device used for controlling the addition or heat to an external component.

A "field programmable gate array" or "FPGA" refers to a circuit or circuit component which can have its functionality defined after construction or fabrication. In an embodiment, an FPGA is a component of an integrated circuit. In embodiments, some integrated circuits comprise an FPGA. FPGAs are useful, for example, for providing desired functionality to an integrated circuit, such as to enable digital and/or analog signal processing.

An "application specific integrated circuit" or "ASIC" refers to a circuit or circuit component which has its functionality defined during construction or fabrication.

A "current monitoring circuit" refers to a circuit which measures or monitors a current being delivered by or delivered to another object or device, such as an electrochemical cell. In embodiments, a current monitoring circuit continuously monitors a current. In embodiments, a current monitoring circuit periodically monitors a current. In embodiments, a current monitoring circuit calculates a total amount of current delivered to or from another object or device, such as an electrochemical cell. In embodiments, a current monitoring circuit comprises a coulometer, a galvanometer or an ammeter.

The terms "true state of charge" and "thermodynamic state of charge" interchangeably refer to a fractional or percentage of the actual charge capacity remaining in an electrochemical cell as compared to the original, theoretical, or maximum capacity of charge in the electrochemical cell. In embodiments, the true state of charge of an electrochemical cell is determined by comparing a condition of the electrochemical cell, such as one or more thermodynamic parameters, with a condition of a reference electrochemical cell and identifying the true state of charge of the electrochemical cell as the state of charge of the reference electrochemical cell having the same condition as the electrochemical cell.

The term "Coulometric state of charge" refers to a fractional or percentage of the charge capacity remaining in an electrochemical cell as compared to the original, theoretical, or maximum capacity of charge in the electrochemical cell and measured by integrating a current actually delivered by or to the electrochemical cell. In embodiments, the Coulometric state of charge and the true state of charge can be different, such as when side reactions take place in an electrochemical cell that do not contribute to charging or discharging the electrodes of the electrochemical cell but are still associated with delivery of current from or to the electrochemical cell. Such side reactions include, but are not limited to, oxidation of an electrolyte in the electrochemical cell and reduction of electrochemical cell. In embodiments a Coulometric state of charge is determined by subtracting the total measured charge delivered by the electrochemical cell (including any charging and discharging of the electrochemical cell) from the original, theoretical or maximum charge capacity of the electrochemical cell and dividing by the original, theoretical or maximum charge capacity of the electrochemical cell.

The present invention provides methods and systems for thermodynamically evaluating electrochemical systems and components thereof, including electrochemical cells such as batteries, fuel, cells and photovoltaics. The present systems and methods are capable of monitoring selected electrochemical cell conditions, such as temperature and composition, and carrying out measurements of a number of cell parameters, including open circuit voltage, time and temperature, with accuracies large enough to allow for precise determination of thermodynamic state functions and materials properties relating to the composition, phase and electrochemical properties of electrodes and electrolytes in an electrochemical cell. Thermodynamic measurement systems of the present invention are highly versatile and provide information for predicting a wide range of performance attributes for virtually any electrochemical system having an electrode pair.

Figure 3:
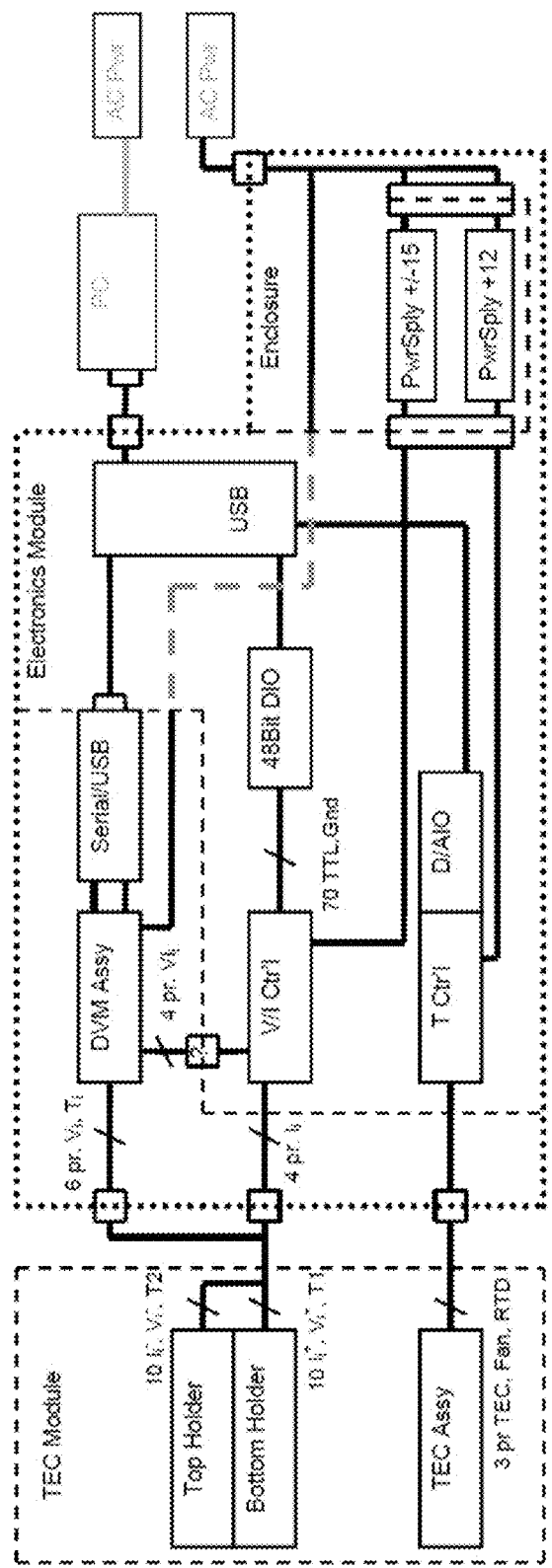
FIG. 3 illustrates a block diagram for a electrochemical thermodynamic measurement system including temperature control components.

FIG. 1 illustrates an exemplary embodiment of a device of the present invention constructed as an integrated circuit 100. Integrated circuit 100 comprises Multiple internal circuit components including an AC to DC converter 101 for converting from mains electricity 102 (e.g., AC 100-240 V) to DC voltages useful for providing power to other circuit components. AC to DC converter 101 is optionally provided as a separate component from integrated circuit 100, for example to reduce the complexity and size of integrated circuit 100, in which case DC voltages are directly provided to other circuit components of integrated circuit 100. The DC voltage output of AC to DC converter 101 is optionally adjustable to provide various DC voltages depending on the power requirements of other circuit components of integrated circuit 100. Optional input/output circuit 103 provides for data communication with an input/output device 104 (e.g., as a keyboard, touch screen or display), to obtain input from and display information to a user. Input/output circuit 103 receives information from display circuit 105 for displaying to a user on input/output device 104, such as computation results received from sub-circuit 106. Input/output circuit 103 provides information to command circuit 107 for converting user input from input/output device 104 to commands for sub-circuit 106. Sub-circuit 106 provides various functionality to integrated circuit 100, including voltage, current and temperature monitoring, voltage, current and temperature control, and a processor for determining thermodynamic parameters and conditions of an electrochemical cell 108 under test. In this embodiment, a temperature control circuit 109 provides control signals to temperature controller 110, which is positioned in thermal communication with electrochemical cell 108. Temperature controller 110 optionally comprises a thermoelectric cooler (TEC) and heat sink. The temperature 111 of temperature controller 110 and/or electrochemical cell 108 is provided to microcontroller 112, which comprises a temperature monitoring circuit. The voltage or current 113 of electrochemical cell 108 is also monitored by microcontroller 112, which comprises a voltage monitoring circuit, for example for monitoring an open circuit voltage of electrochemical cell 108. Microcontroller 112 optionally comprises a field programmable gate array circuit or another circuit having the desired functionality for measuring temperature, voltage and computing thermodynamic parameters and electrochemical cell conditions. In this embodiment, a voltage and current control circuit 114 provides voltage and/or current 115 to electrochemical cell 108, for example for charging electrochemical cell 108. Optionally, voltage and current control circuit 114 also provides voltage and current monitoring of electrochemical cell 108, thereby relieving microcontroller 112 from having to monitor voltage or current 113 of electrochemical cell 108. FIG. 3 illustrates a block diagram for a electrochemical thermodynamic measurement system including temperature control components.

Figure 2:
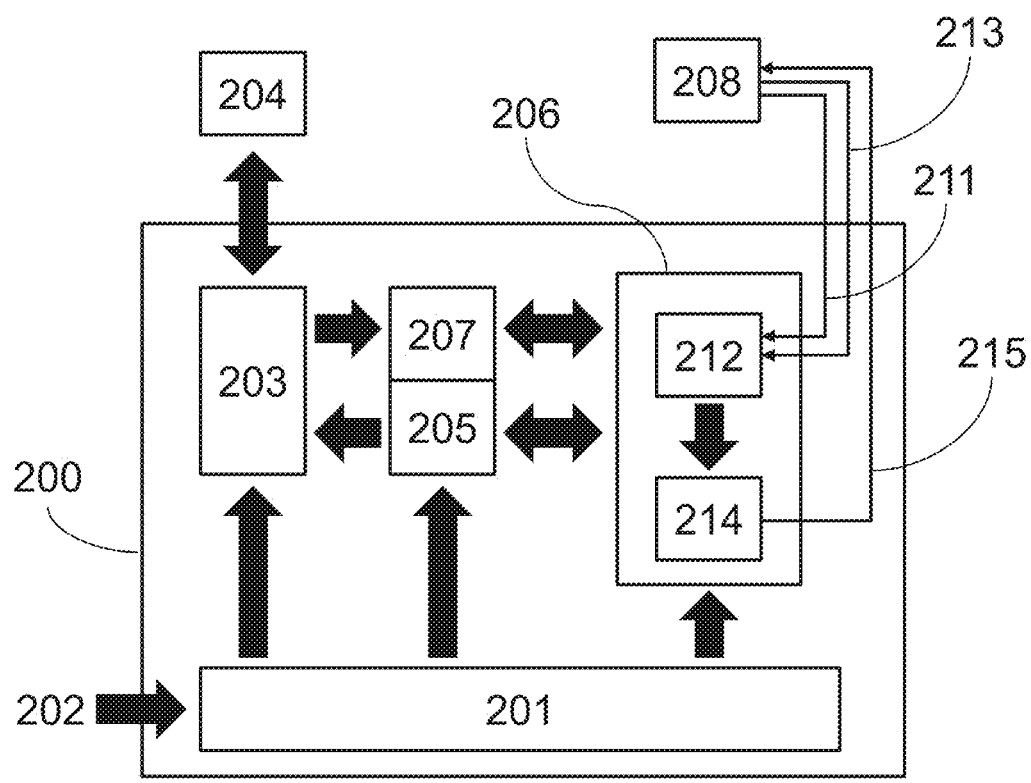
FIG. 2 provides a block diagram of an electrochemical thermodynamic measurement system (ETMS) incorporated into a single chip.

In embodiments, inclusion of temperature control circuitry and temperature control hardware adds complexity, size and cost to a device of the present invention. Instead, natural temperature changes of an electrochemical cell as it is charged and discharged can be exploited to obtain measurements on an electrochemical cell at various temperatures. FIG. 2 illustrates an exemplary embodiment of a device of the present invention that does not include a temperature controller or associate control circuitry. In this embodiment, integrated circuit 200 comprises multiple internal circuit components including an AC to DC converter 201 for converting from mains electricity 202 (e.g., AC 100-240 V) to DC voltages useful for providing power to other circuit components. AC to DC converter 201 is optionally provided as a separate component from integrated circuit 200, for example to reduce the complexity, size and cost of integrated circuit 200, in which case DC voltages are directly provided to other circuit components of integrated circuit 200. The DC voltage output of AC to DC converter 201 is optionally adjustable to provide various DC voltages depending on the power requirements of other circuit components of integrated circuit 200. Optional input/output circuit 203 provides for data communication with an input/output device 204 (e.g., as a keyboard, touch screen or display), to obtain input from and display information to a user. Input/output circuit 203 receives information from display circuit 205 for displaying to a user on input/output device 204, such as computation results received from sub-circuit 206. Input/output circuit 203 provides information to command circuit 207 for converting user input from input/output device 204 to commands for sub-circuit 206. Sub-circuit 206 provides various functionality to integrated circuit 200, including temperature, voltage and current monitoring and voltage and current control, and a processor for determining thermodynamic parameters and conditions of an electrochemical cell 208 under test. The temperature 211 of electrochemical cell 208 is provided to microcontroller 212, which comprises a temperature monitoring circuit. The voltage or current 213 of electrochemical cell 208 is also monitored by microcontroller 212, which comprises a voltage monitoring circuit, for example for monitoring an open circuit voltage of electrochemical cell 208. Microcontroller 212 optionally comprises a field programmable gate array circuit or another circuit having the desired functionality for measuring temperature, voltage and computing thermodynamic parameters and electrochemical cell conditions. In this embodiment, a voltage and current control circuit 214 provides voltage and/or current 215 to electrochemical cell 208, for example for charging electrochemical cell 208. Optionally, voltage and current control circuit 214 also provides voltage and current monitoring of electrochemical cell 208, thereby relieving microcontroller 212 from having to monitor voltage or current 213 of electrochemical cell 208.

Figure 4:
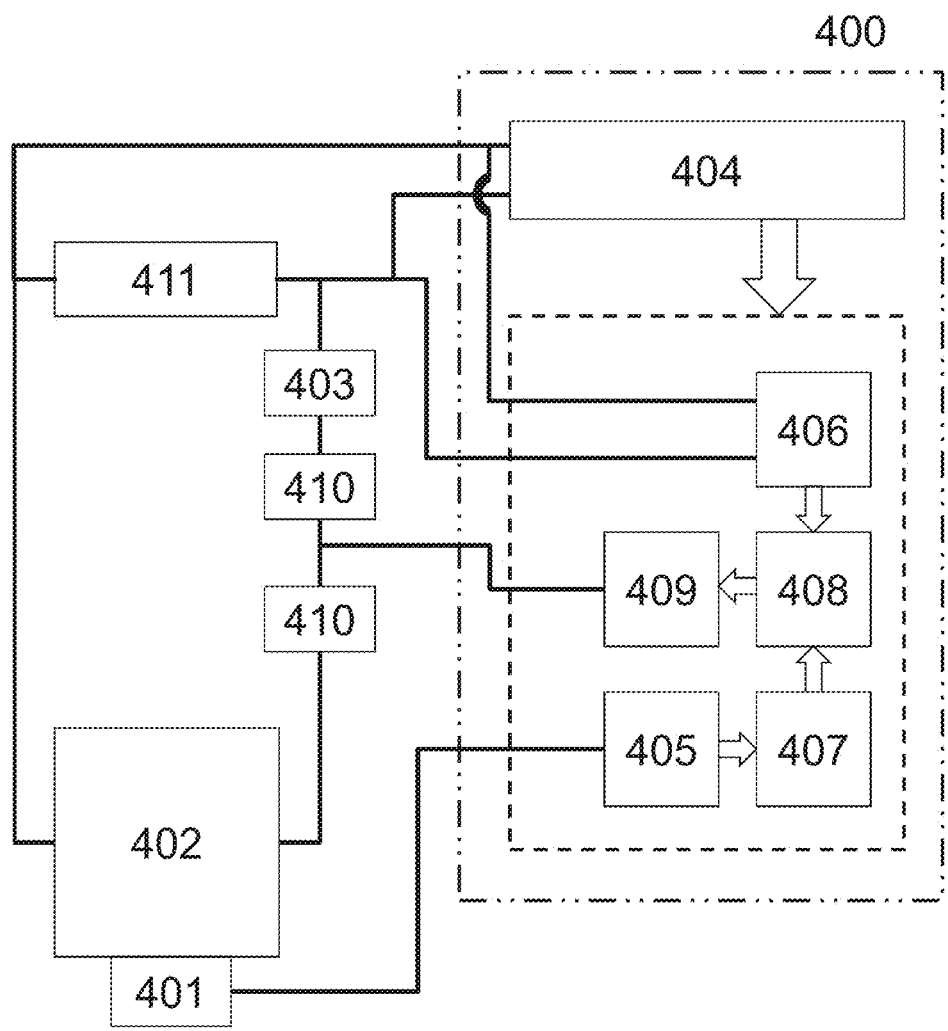
FIG. 4 illustrates an embodiment comprising a circuit for determining a thermodynamic parameter.

FIG. 4 illustrates an embodiment of a device of the present invention comprising a circuit for determining a thermodynamic parameter. For example, the embodiment shown in FIG. 4 comprises an entropy monitoring circuit 400. A temperature sensor 401 is positioned in thermal communication to the cathode or anode of the electrochemical cell 402. Useful temperature sensors 401 include, but are not limited to thermocouple, thermistor, diode or transistor based temperature sensors. As used herein the term thermistor refers to a resistive element where the resistance value changes according to the temperature, thereby permitting determination of temperature by measuring the resistance of the thermistor. A current sensor 403 is positioned in electrical communication with the electrochemical cell, and is useful for determining if the electrochemical cell 402 is under open circuit voltage conditions, for example, when no current is flowing into or from the electrochemical cell, thereby permitting a determination of the open circuit voltage of the electrochemical cell 402. The entropy monitoring circuit 400 shown in FIG. 4 comprises a power conditioning circuit 404, a temperature-voltage converter 405, voltage differentiators 406 and 407, a division circuit 408 and a modulation circuit 409. One or more inductors 410 are positioned in electrical communication with the electrochemical cell. In embodiments, the output of modulation circuit 409 is either a frequency modulated or phase shift modulated voltage signal that contains information related to the change in voltage of the electrochemical cell as a function of time (dV/dt). The inductors 410 are useful for blocking an AC signal from reaching the electrochemical cell 402 and any load 411. The power conditioning circuit 404 provides power to the monitoring circuit 400 and can cut off the power to the monitoring circuit 400 when the electrochemical cell 402 is not in use to prevent unnecessarily draining the energy stored in the electrochemical cell 402.

Figure 5:
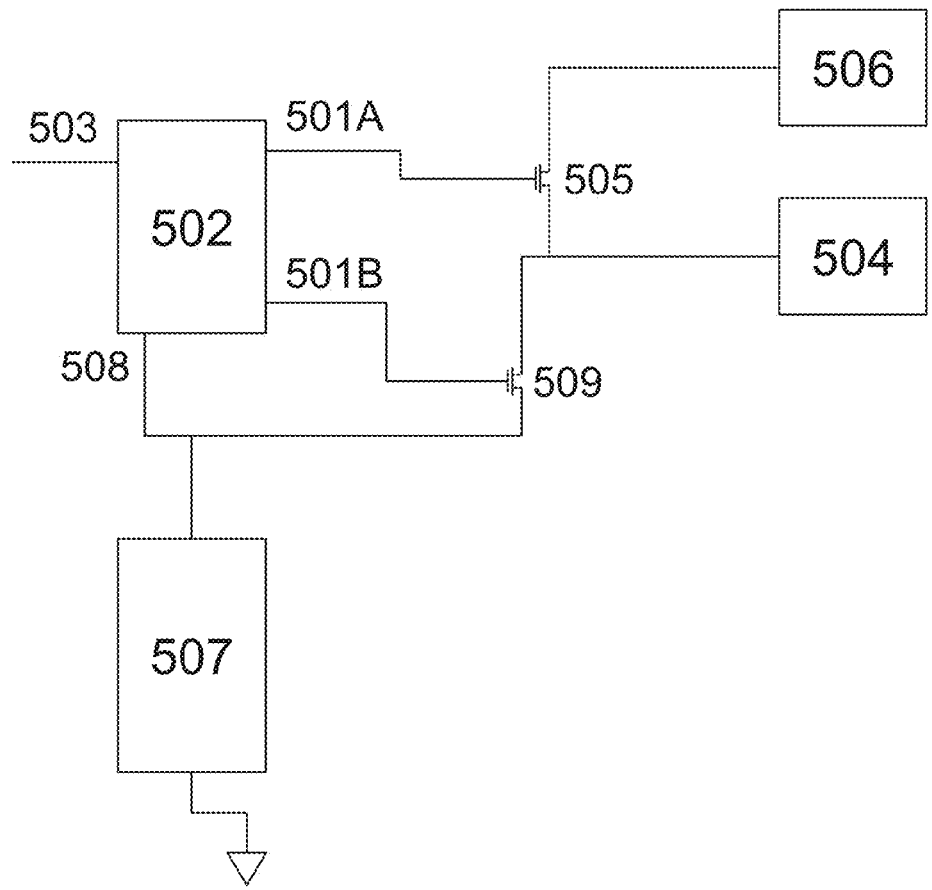
FIG. 5 illustrates a power switching circuit embodiment.

Power conditioning circuit 404 also operates to provide power to the monitoring circuit 400 only when the electrochemical cell 402 is under open circuit conditions such that monitoring circuit 400 does not consume additional energy unnecessarily. Power conditioning circuit 404 also serves to convert voltage from electrochemical cell 402 to voltages required for operation of various components of monitoring circuit 400. FIG. 5 illustrates an exemplary power switching circuit embodiment. Here, the output 501A of flip-flop 502 changes from low logic to high logic when the input signal 503 changes from high logic to low logic. The input signal 503 corresponds to a current measurement signal of the electrochemical cell 504. A change from high logic to low logic in input signal 503 corresponds to stopping the current being supplied by electrochemical cell 504, such as occurs when under open circuit voltage conditions, indicating that the open circuit voltage can be captured. When the output logic 501A is high, transistor 505 is turned on, allowing the monitoring circuit to be turned on by connecting the anode from electrochemical cell 504 to a switching mode power supply 506 which powers the monitoring circuit. An RC circuit 507, such as having a resistor and capacitor in parallel, is provided at the reset pin 508 of flip-flop 502 for turning off the monitoring circuit, such as after a pre-set time or if the electrochemical cell 504 is permanently shut off or put into open circuit voltage mode. This is useful for powering off switching mode power supply 506 and preventing the monitoring circuit from continuing to drain electrochemical cell 504. When electrochemical cell 504 is providing current, flip-flop output 501B is high logic, and therefore, transistor 509 is turned on and the capacitor in RC circuit 507 is charging. When the electrochemical cell 504 is open circuit, flip-flop output 501B is low logic and the capacitor in RC circuit 507 will be discharged through the resistor in RC circuit 507. After some time, the capacitor will become discharged and the voltage at reset pin 508 will become zero and this will reset flip-flop 502 such that flip flop output 501A becomes low logic and cuts off power supply 506 from delivering power to the monitoring circuit.

Figure 6A:
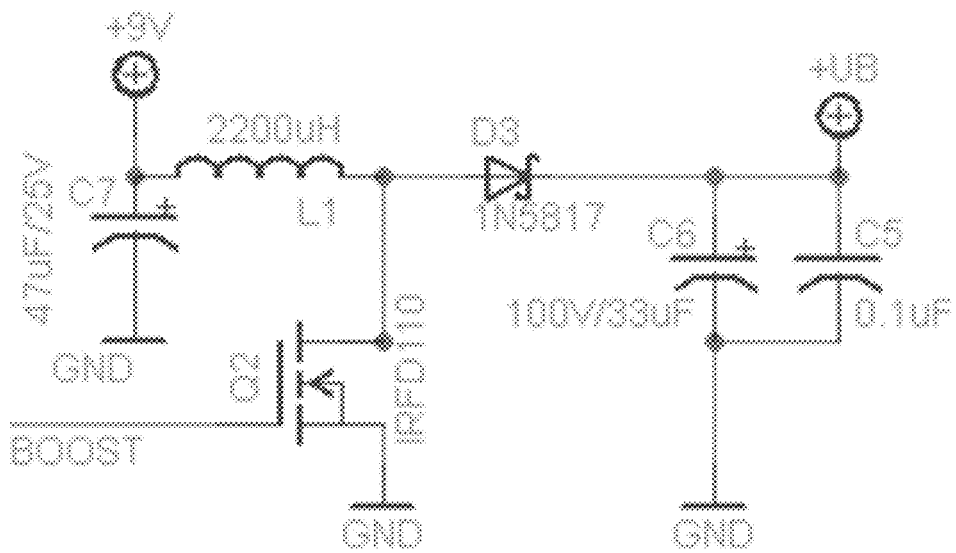
FIGS. 6A and 6B illustrate voltage converter circuit embodiments.
Figure 6B:
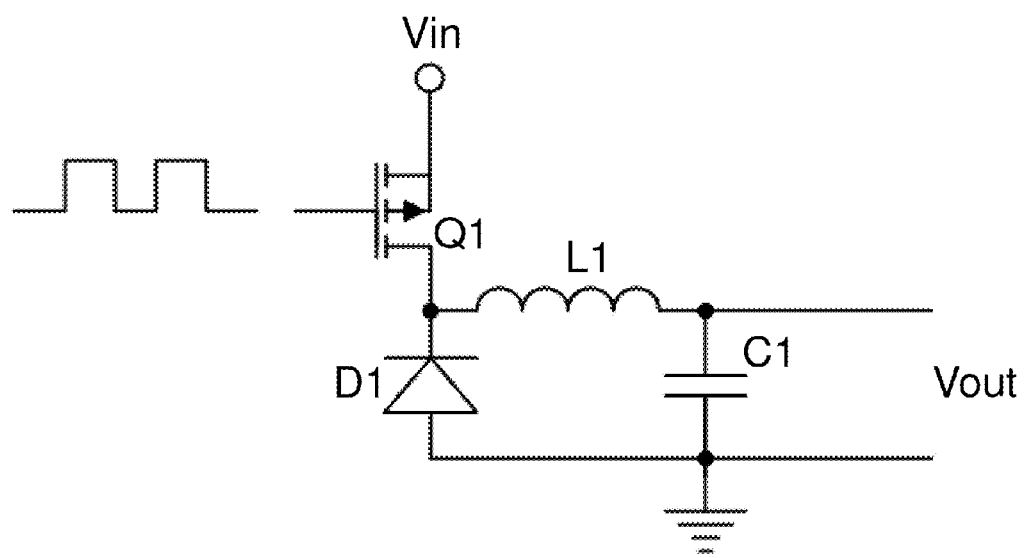

The voltage provided by the electrochemical cell 505 is optionally converted to different supply voltages for different sub-circuits, and this can be achieve using a switching mode power supply, such as comprising a voltage converting circuit. FIGS. 6A and 6B illustrate two exemplary voltage converting circuit embodiments. FIG. 6A illustrates a boost converter circuit embodiment that increases a voltage, for example, converting 3.0 V to 9 V and 15 V. FIG. 6B illustrates a Buck converter circuit embodiment that reduces a voltage, for example, converting 3.0 V to 1.5 V.

Figure 7:
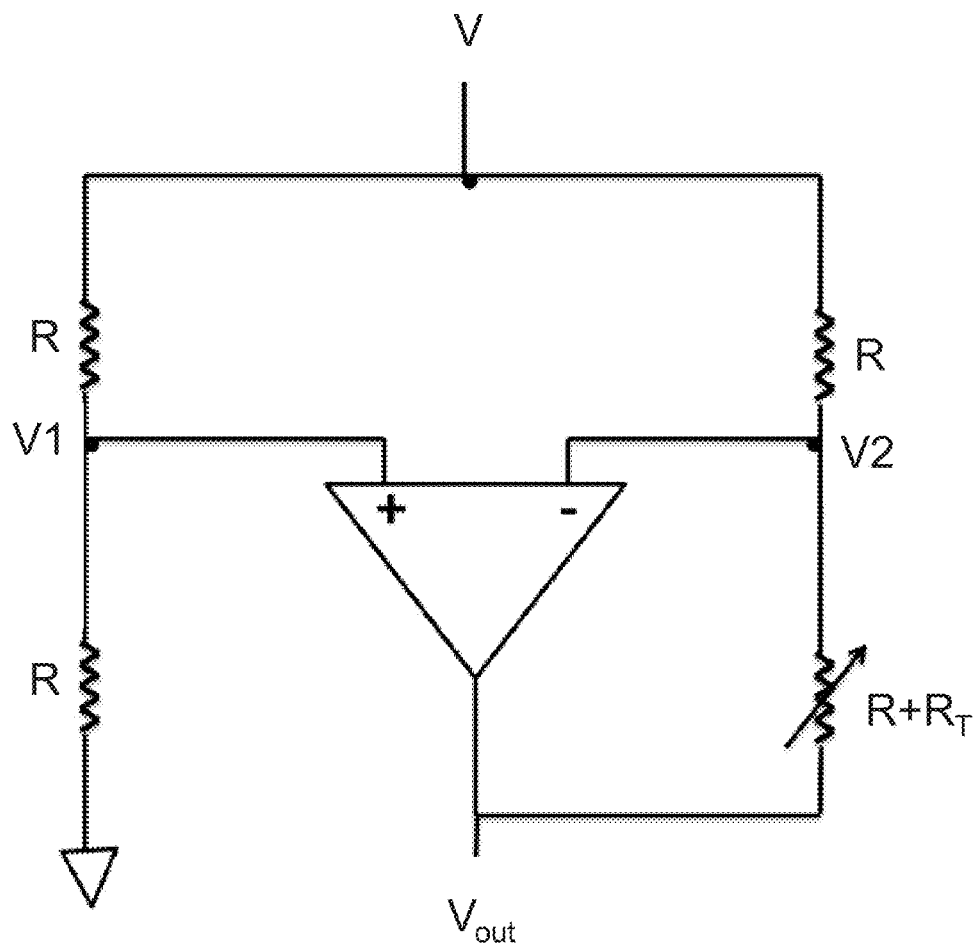
FIG. 7 illustrates a temperature to voltage converter embodiment

Temperature-voltage converter 405 is used to convert the temperature of electrochemical cell 402 sensed by temperature sensor 401 into voltage. In embodiments, the conversion is such that the converted voltage is linearly proportional to the temperature of electrochemical cell 402. FIG. 7 illustrates an exemplary temperature-voltage converter embodiment. In the embodiment shown in FIG. 7, the temperature is measured as a resistance, such as a change in resistance value ($R_T$) due to temperature. In the circuit embodiment shown in FIG. 7, three of four resistors have a resistance R, while the fourth has a resistance $R+R_T$. Here, $V1=V\cdot R/(R+R)=V/2$ and $V-V2/R=(V2-V_{out})/(R+R_T)$ and $V_{out}=-V\cdot R_T/2\cdot R$ and thus $V_{out}$ is linearly proportional to the resistance change due to temperature $R_T$.

Figure 8:
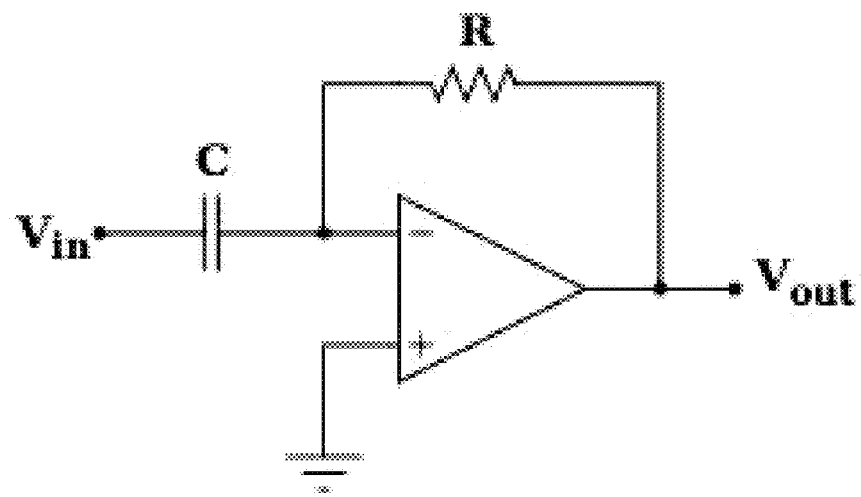
FIG. 8 illustrates a voltage differentiator embodiment.

Voltage differentiators 406 and 407 perform time differentiation of a voltage. In this embodiment, voltage differentiators 406 and 407 respectively provide dV/dt and dT/dt, where V is the open circuit voltage and T is the temperature (expressed in voltage) of electrochemical cell 402 and t is time. FIG. 8 illustrates an exemplary voltage differentiator embodiment.

Figure 9:
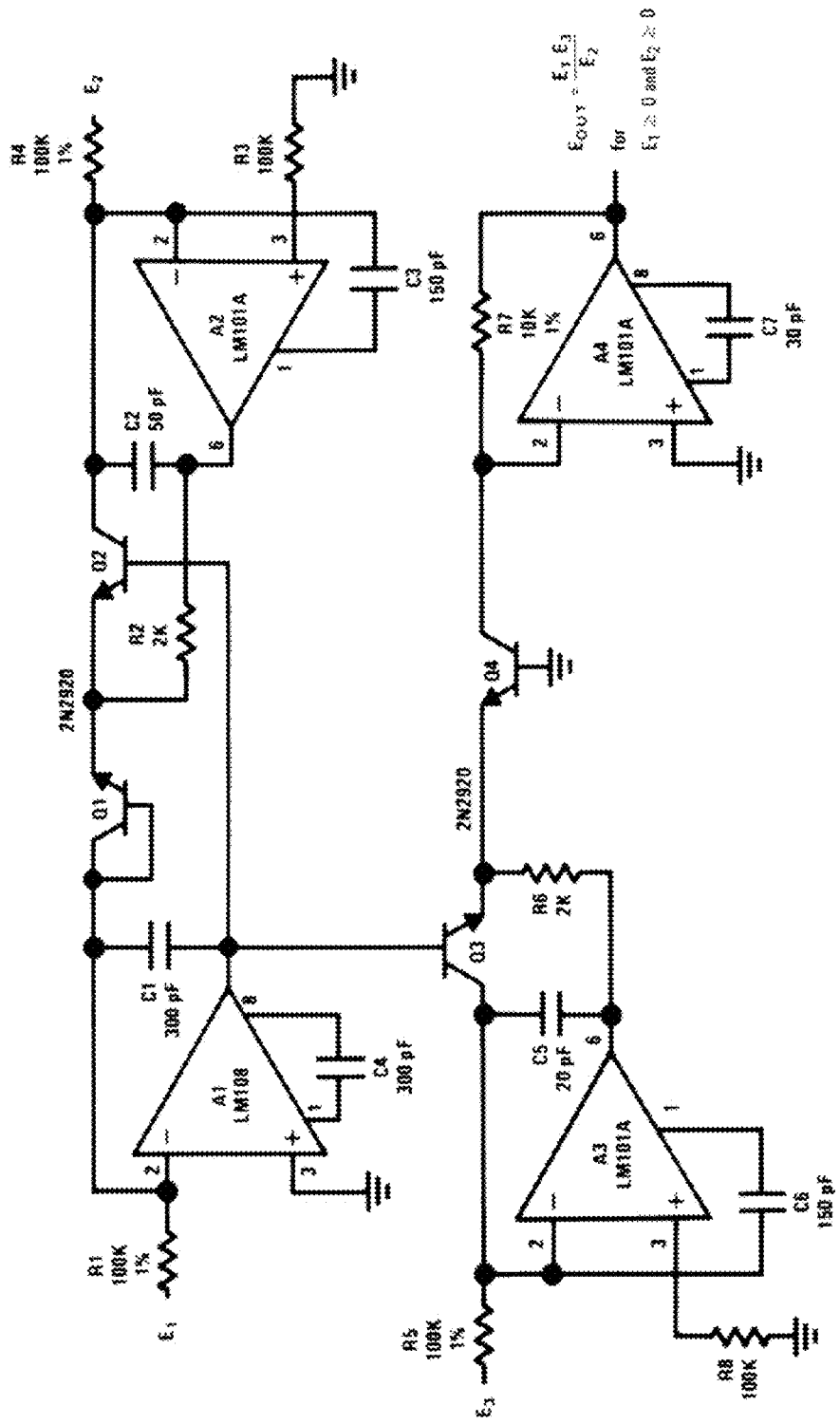
FIG. 9 illustrates a division circuit embodiment.

Division circuit 408 is used to perform division of two circuits. In this embodiment, the signals are dV/dt and dT/dt, which provides dV/dT by the division. FIG. 9 illustrates an exemplary division circuit embodiment.

Figure 10A:
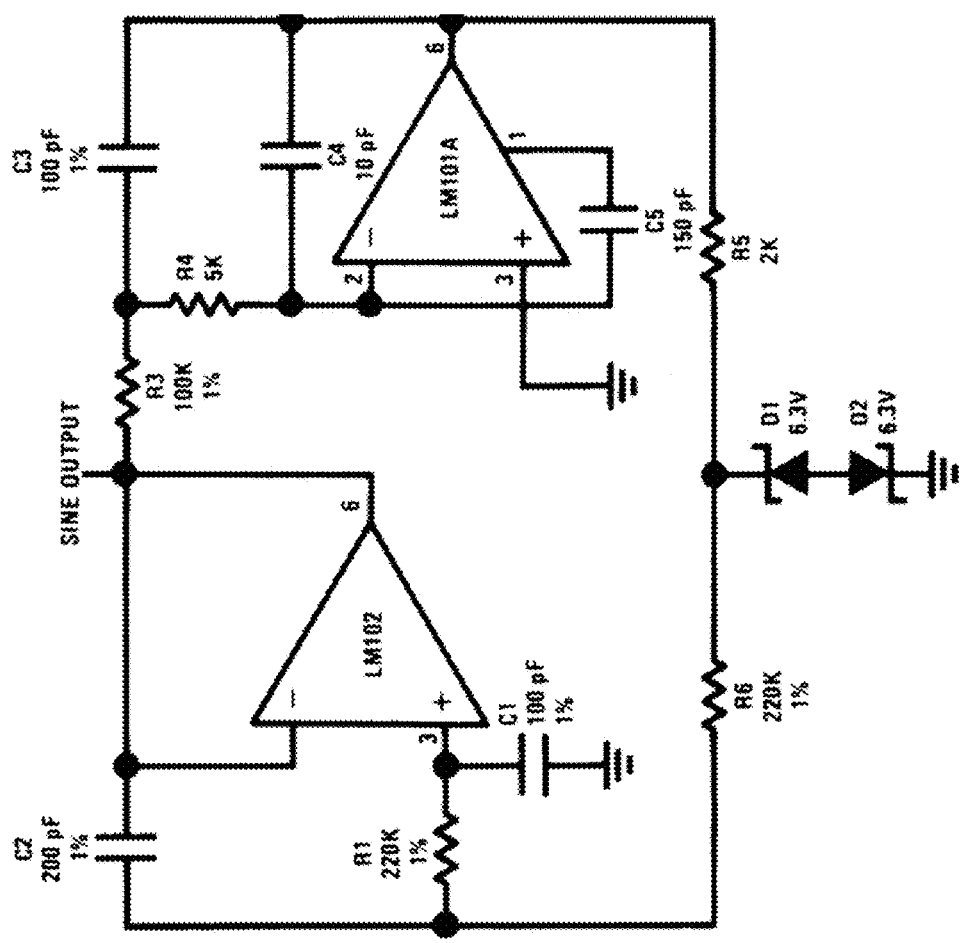
FIGS. 10A and 10B illustrate modulation circuit embodiments.
Figure 10B:
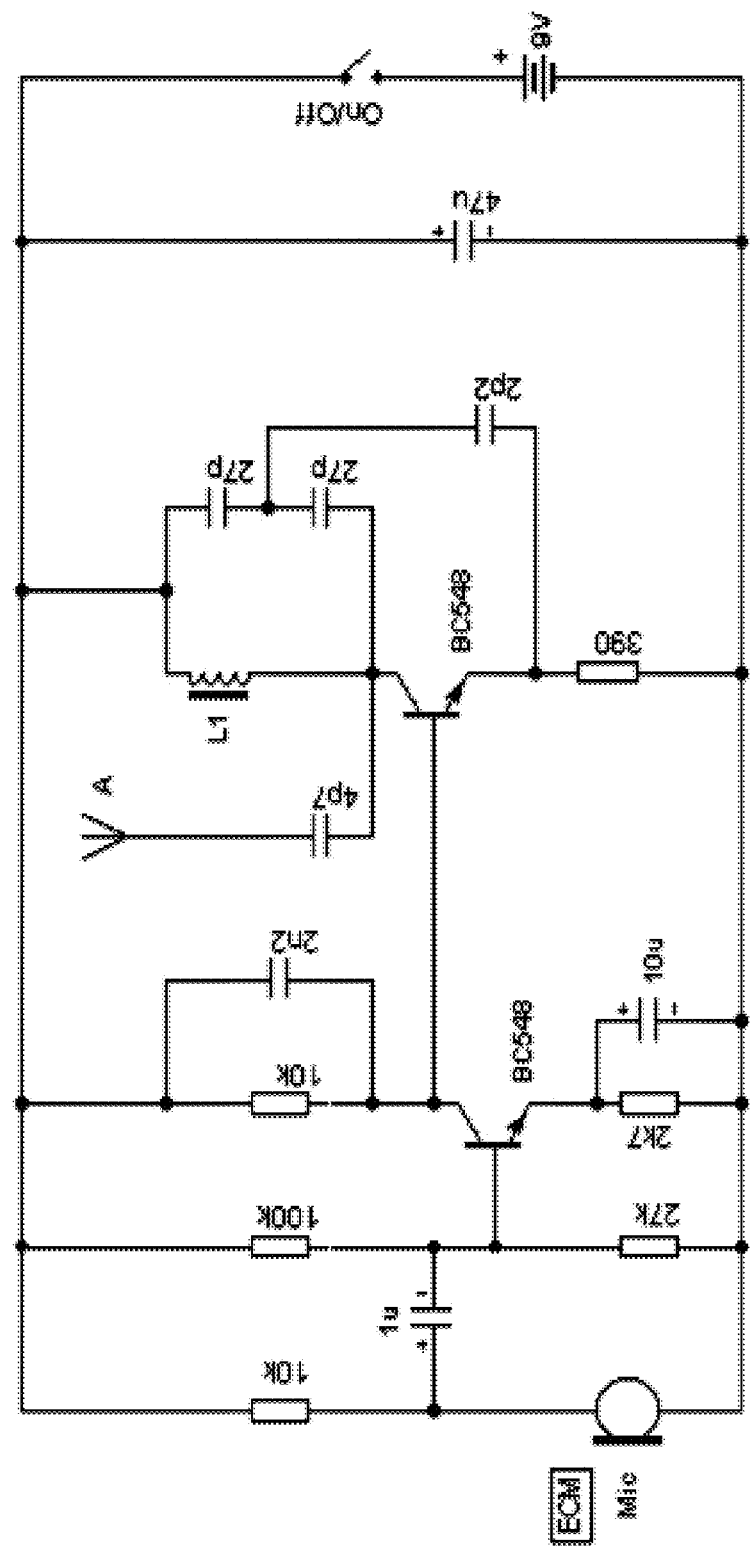
Figure 11:
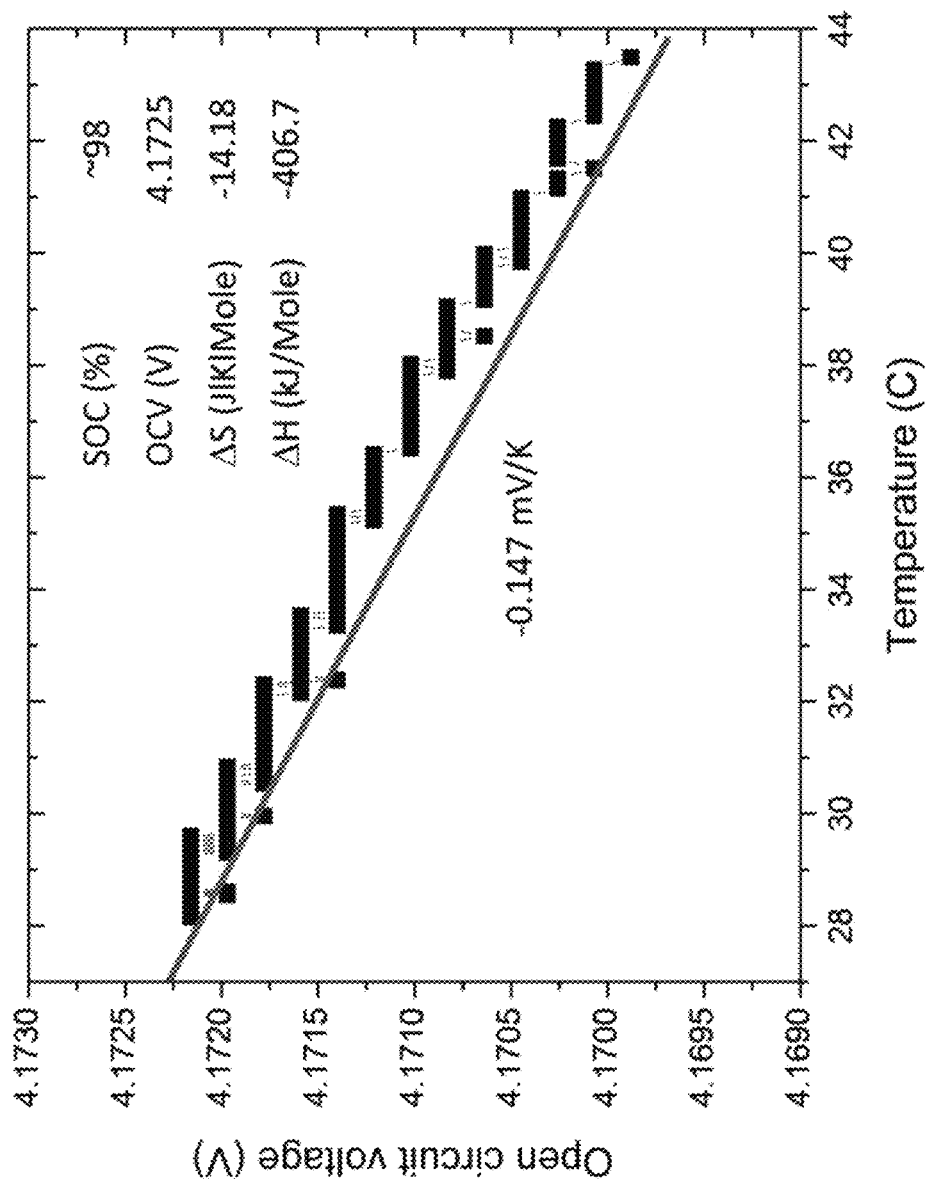
FIGS. 11-14 illustrates open circuit voltage versus temperature data obtained for four cells in which the temperature of the cells was not controlled.
Figure 12:
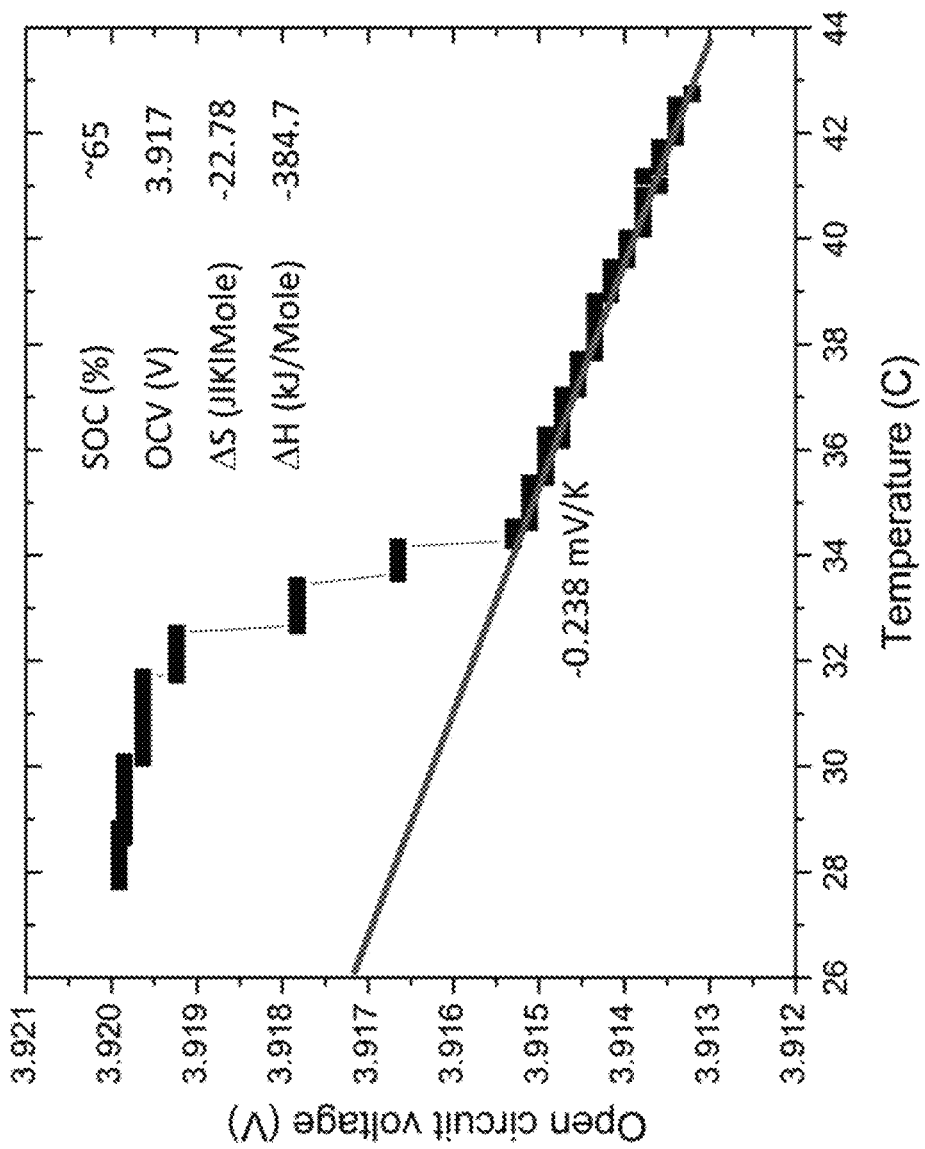
Figure 13:
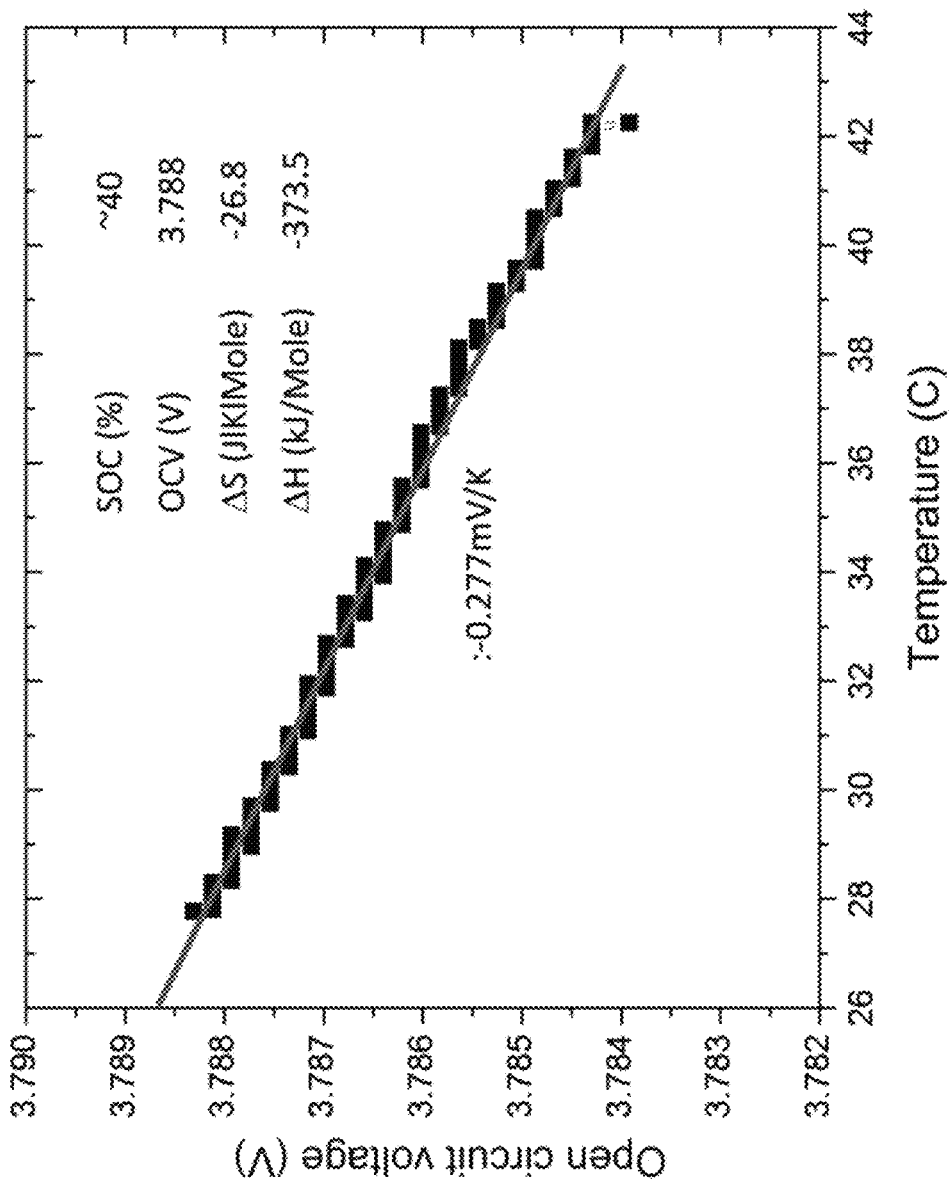
Figure 14:
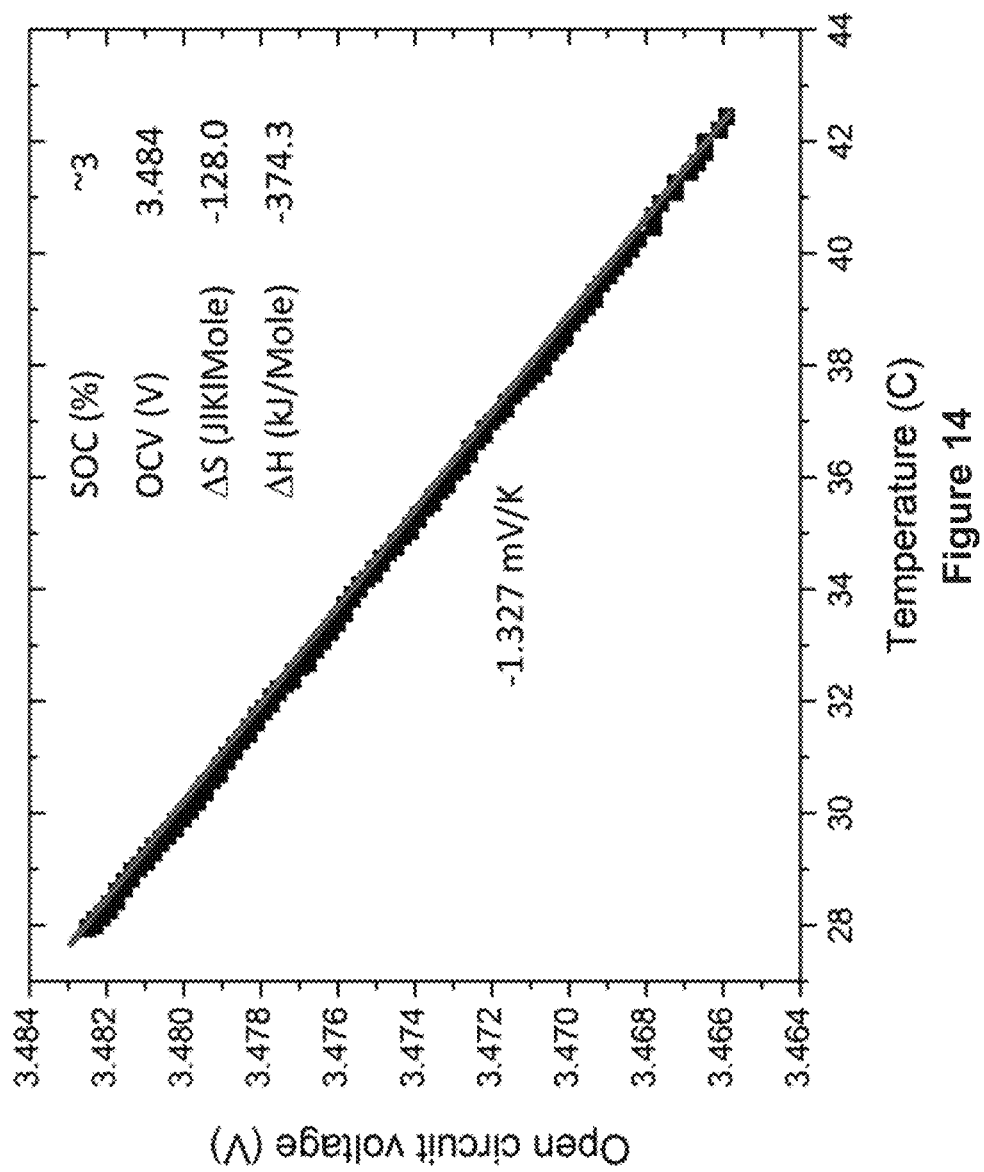

As no additional electrodes are to be introduced into electrochemical cell 402, the signal that contains dV/dt will be accessed through the two existing electrodes of electrochemical cell 402. Hence, the signal will be modulated by modulation circuit 409, for example, using either frequency or phase shift modulation for a specific carrier frequency such that the signal can be later extracted through an electronic filter without the influence of other noise. In addition, such a time varying signal will also not impact the load current and electrochemical cell 402 by using inductors 410 described above. FIGS. 10A and 10B illustrate exemplary modulation circuit embodiments. FIG. 10A depicts a typical high frequency sine wave generator for the carrier; FIG. 10B illustrates a typical frequency modulation circuit, where the input from the division circuit is provided at the Mic/ECM location and the antenna (denoted as A) is the output, optionally transmitted wirelessly or connected to the electrochemical cell, such as at the anode.

To further demonstrate the components, performance and functionality of the present systems and methods, entropies and enthalpies of electrochemical reactions taking place at an anode or a cathode is examined. First, a general background explanation is provided, establishing the relationships between experimental measurements provided and important thermodynamic parameters which govern important electrochemical properties of the electrode. Second, a description of the components of the measurement system is provided.

To determine the evolution of the entropy and enthalpy of a reaction taking place at an electrode, such as lithium intercalation into a material $Li_xM$ as a function of x, the temperature dependence of the open circuit voltage is examined using the present invention. This voltage is related to the Gibbs free energy of reaction by the thermodynamic identity:

$$\Delta G = -nFU$$

where U is the equilibrium potential of the electrode and F the Faraday number. For the $Li^+/Li$ electrochemical couple one electron is exchanged, so n=1.

The partial molar enthalpy, $\Delta H$, and entropy, $\Delta S$, of the reaction are derived with respect to the amount of charge passed. In the following, $\Delta H$ and $\Delta S$ are assumed independent of temperature. Although many measurements are made at varying temperatures, this assumption may be reliable as long as there are no phase transitions in the measured temperature range. Such is, for instance, the case for lithium cobalt oxide at the composition $Li_{0.5}CoO_2$, where a slight temperature change triggers the monoclinic to hexagonal phase transition close to room temperature.

The values measured are partial molar variables. From the first law of thermodynamics relating the internal energy of the system E to the work W and heat dissipated Q, the differential of the enthalpy can be obtained:

$$dE = \delta W + \delta Q$$
$$= -PdV + \mu dn + Tds$$
$$dH = dE + PdV + VdP$$
$$= \mu dn + TdS + VdP$$

with μ, the chemical potential of the cathode, referred to the metallic lithium anode, and n is the number of lithium atoms exchanged. The term μdn is the electrical work of the charge exchanged. In this study, the pressure P is constant, so the third term, VdP, is neglected. Using (6) the Gibbs free energy can then be written as:

$$dG = dH - TdS - SdT$$
$$= \mu dn - SdT$$

To get molar values we use x=n/N, where N is Avogadro's number. The chemical potential is related to the open circuit voltage U by μ–eU where e is the charge of the electron.

$$dG = -NeUdx - SdT$$
$$= -FUdx - SdT$$

Since F=Ne. Then using Maxwell's relation for mixed second derivatives, we get the partial molar entropy of lithium intercalation as a function of the open circuit voltage:

$$\left.\frac{\partial S}{\partial x}\right|_T = F\left.\frac{\partial U}{\partial T}\right|_x = \Delta S$$

Since by definition H=G+TS we find:

$$\left.\frac{\partial H}{\partial x}\right|_T = \left.\frac{\partial G}{\partial x}\right|_T + T\left.\frac{\partial S}{\partial x}\right|_T$$
$$= N\left.\frac{\partial G}{\partial n}\right|_T + TF\left.\frac{\partial U}{\partial T}\right|_x$$

By definition $(\partial G/\partial n)_T$ is the chemical potential μ=–eU. We thus obtain the partial molar enthalpy of lithium intercalation as a function of the open circuit voltage, U:

$$\left.\frac{\partial H}{\partial x}\right|_T = -FU + TF\left.\frac{\partial U}{\partial T}\right|_x = \Delta H$$

It must be noted that $\mu=\mu_c-\mu_a$, is the difference of chemical potential between the cathode and the anode. As a consequence all our results are referred to the lithium anode, for which the chemical potential is supposed to be a constant at different states of charge.

The invention may be further understood by the following non-limiting examples.

Example 1

The Imbedded Chip

The devices described in this example are designed to be imbedded in an electrochemical cell. Optionally, the chip can be imbedded in a battery module, such as a module comprising 2 to 20 electrochemical cells, and in a battery pack, such as comprising 1 to 100 modules). The imbedded chip is designed to collect current, voltage and temperature data within individual cells and convert them to useful thermodynamics data in order to assess the battery state of health and state of charge.

The block diagram shown in FIG. 3 illustrate the configuration of an electrochemical thermodynamics measurement system (ETMS). The ETMS comprises a thermoelectric couple (TEC) module for controlling the temperature of one or more electrochemical cells, as well as temperature control components, voltage and current monitoring and control components, power supply components and various data and communications components. In embodiments, devices of the present invention specifically exclude temperature control components, such as the thermoelectric couple module and associate control circuitry. In embodiments, devices of the present invention utilize temperature changes that occur naturally as an electrochemical cell is heated during charging or discharging or that occur naturally as an electrochemical cell relaxes towards ambient temperature after charging or discharging is halted.

Optionally, a number of functions of the ETMS can be implemented in a single chip. FIG. 1 illustrates a block diagram showing the configuration of the ETMS incorporated into a single chip. The functionality of such a single chip system is optionally different for different applications. For example, for a personal computer or laptop battery, the cell data is optionally collected automatically by the single chip that provides data periodically to the PC, where state of health or other cell conditions calculations are performed by software running on the PC. In other applications, the calculations of state of health or other cell conditions are optionally made within the single chip itself.

Example 2

Non-Equilibrium Measurements of Open Circuit Voltage

In embodiments, devices of the present invention are incorporated into electrochemical cells and systems drawing power from electrochemical cells. After charging or discharging of an electrochemical cell is halted, it may take time for the electrochemical cell to reach equilibrium or thermochemically stabilized conditions. For certain embodiments, the devices may seldom have the opportunity to measure an electrochemical cell's open circuit voltage when the electrochemical cell is at equilibrium. For these embodiments, the open circuit voltage needs to be estimated without having to wait for the electrochemical cell to reach equilibrium. In embodiments, the change of open circuit voltage of an electrochemical cell after charging or discharging of the electrochemical cell is halted follows an exponential decay shape. By monitoring a period of the exponential decay of open circuit voltage, the time constant for the exponential decay can be determined and the asymptotic value that the exponential decay is approaching (i.e., the equilibrium value) can be estimated.

Example 3

Comparison Between Controlled and Uncontrolled Temperature

Four 18650 lithium ion cells were subjected to two separate tests. In the first, thermodynamics parameters were measured using controlled temperature. The state of charge of the cells was change by 5% increments and at each state of charge the cell's open circuit voltage was measured during cooling from 25° C. to 10° C. in a cell holder equipped with temperature control, enabling ΔS and ΔH of the cell to be calculated at each state of charge.

In the second test, the cells were charged to 4.2 V and then discharged to a pre-defined state of charge: 98% (cell 1), 65% (cell 2), 40% (cell 3) and 3% (cell 4). A thermocouple was attached to each cell and the cells were heated in an oven to about 55° C., simulating natural heating by charging or discharging. The cells were taken out of the oven and covered with a thermal isolation material. The cells' temperatures and the open circuit voltages were monitored as the cells cooled to the ambient temperature. Using the open circuit voltage versus temperature profiles, $\Delta S$ and $\Delta H$ were calculated for each cell.

Figure 16:
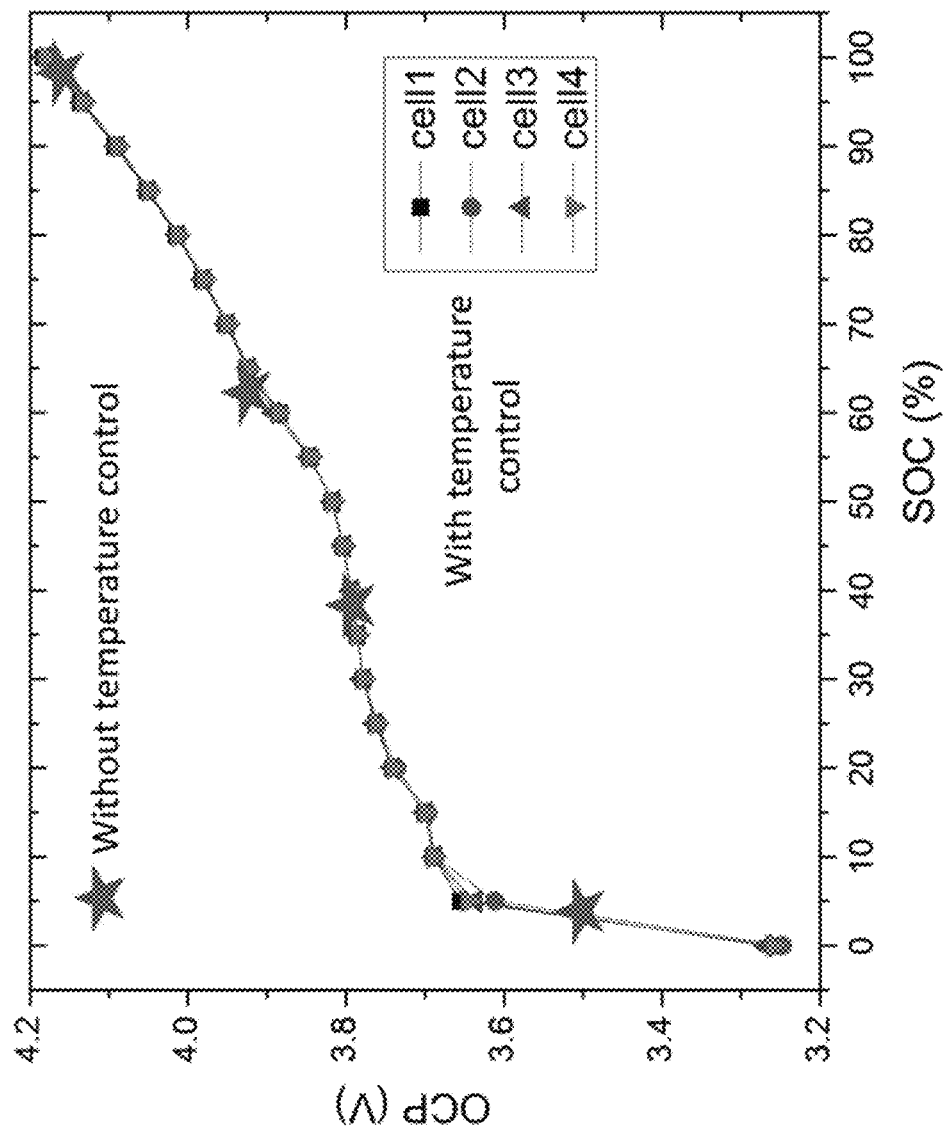
FIG. 16 illustrates data showing a comparison of measurements of open circuit voltage obtained with and without temperature control.
Figure 17:
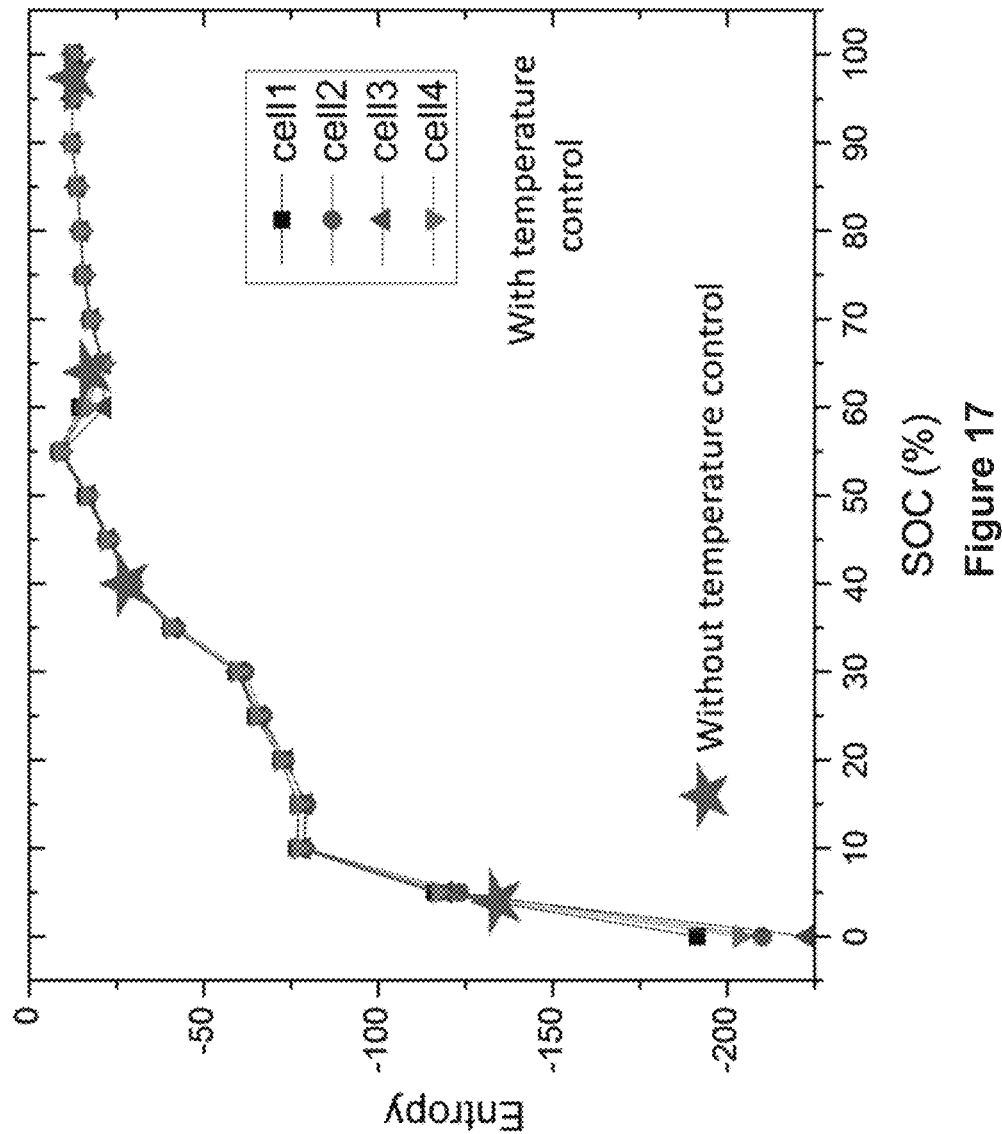
FIG. 17 illustrates data showing a comparison of measurements of changes in entropy obtained with and without temperature control.
Figure 18:
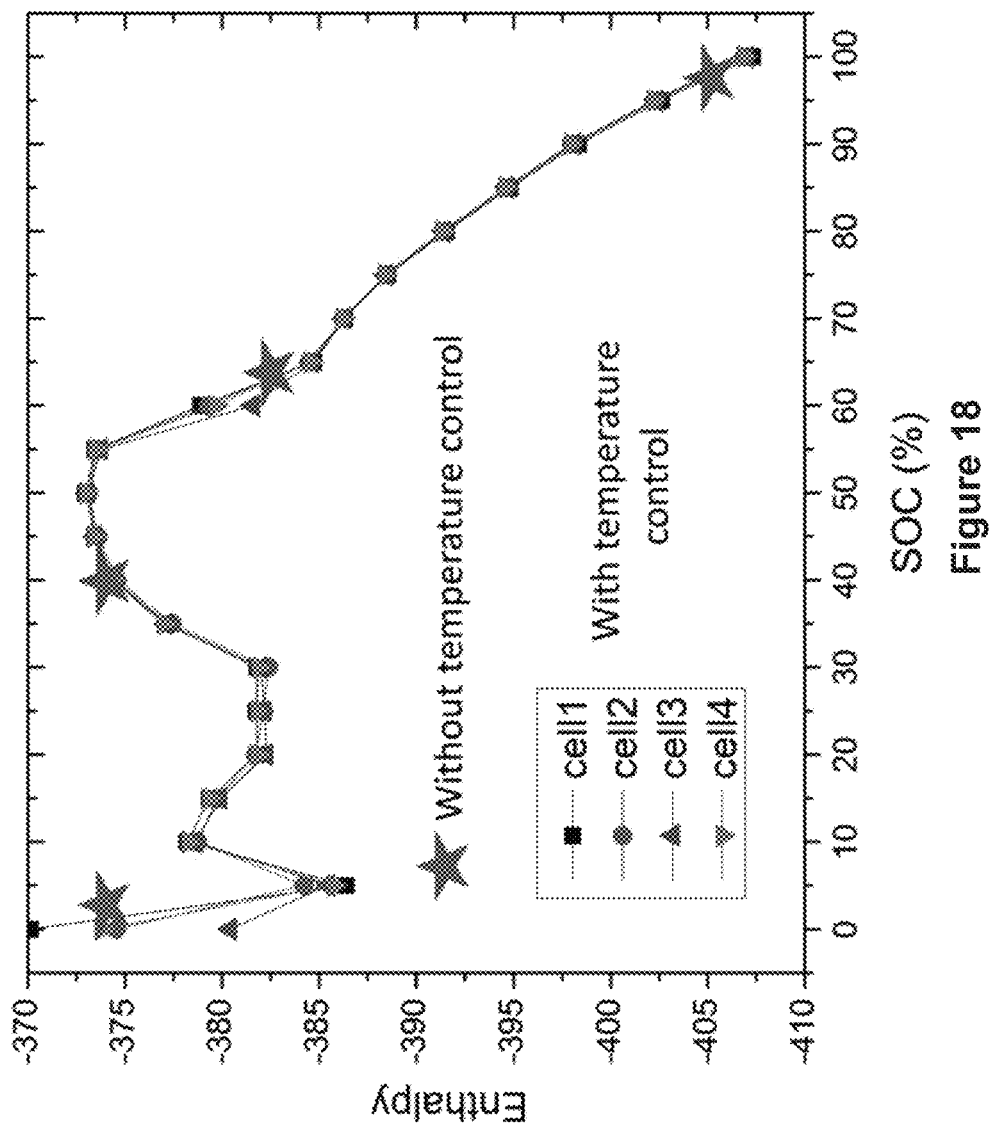
FIG. 18 illustrates data showing a comparison of measurements of changes in enthalpy obtained with and without temperature control.
Figure 19:
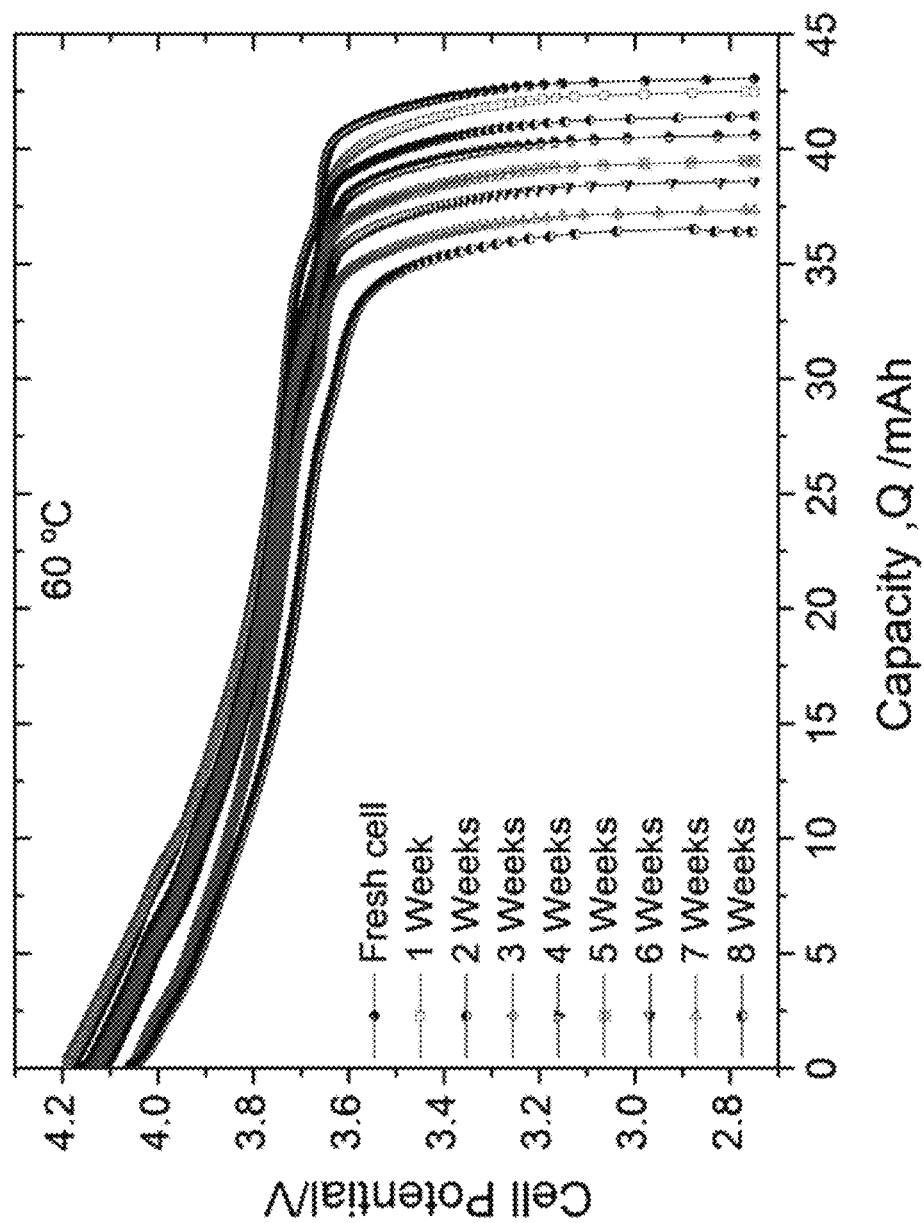
FIGS. 19 and 20 provide data illustrating the discharge profiles of cells aged at 60° C. and 70° C., respectively, over a period of 8 weeks.

FIGS. 11-14 illustrates data obtained for the four cells in which the temperature of the cells was not controlled. FIG. 15 provides a summary of the analysis results of FIGS. 11-14. FIG. 16 illustrates data showing a comparison of open circuit voltage data obtained with and without temperature control. FIG. 17 illustrates data showing a comparison of measurements of open circuit voltage obtained with and without temperature control. FIG. 18 illustrates data showing a comparison of measurements of changes in entropy obtained with and without temperature control. FIG. 19 illustrates data showing a comparison of measurements of changes in enthalpy obtained with and without temperature control.

The results of the comparison illustrate that thermodynamics data, including open circuit voltage, $\Delta S$ and $\Delta H$, can be obtained at different states of charge without temperature control, i.e., during cell cooling to ambient temperature. These data are consistent with that measured with active control over cell conditions, including SOC and temperature. This comparison illustrates that temperature control is not essential to measure thermodynamics data on an electrochemical cell.

The comparison also provides useful insights to determination of the true or thermodynamic state of charge of an electrochemical cell. As the electrochemical cell is charged and discharged under non-controlled conditions, side reactions can take place, such as oxidizing or reducing the electrolyte or other reactions that do not contribute to charging or discharging the cell electrodes. Under conditions where side reactions are taking place, measurement of the cell's SOC by a Coulometric measurement, such as Coulomb counting or current integration, will not provide a true measurement of the cell's SOC. Because the measured thermodynamics data under non-controlled temperature conditions are consistent with those measured under carefully controlled temperature conditions, the non-controlled temperature data can be used to determine the true SOC of the electrochemical cell. For example, the true SOC of a test electrochemical cell operating under non-controlled conditions can be obtained as the SOC for an equivalent chemistry electrochemical cell under controlled conditions having the same thermodynamics parameters as those measured for the test electrochemical cell operating under non-controlled conditions.

Example 4

State of Health and State of Safety Determination

This example describes the principle of assessment methods for determination of a state of safety (SOS) and state of health (SOH) of an electrochemical cell. Differential entropy and differential enthalpy at a defined state of charge (SOC) or open circuit voltage (OCV) can be used to assess an electrochemical cell's SOH and SOS. SOH relates to the cell's energy storage performance decay due to materials degradation as components of the cell age. Capacity loss and discharge voltage decreases are among the SOH metrics for electrochemical cells.

In the differential thermodynamics measurements technique, thermodynamics data (e.g., $\Delta S$ and $\Delta H$) are measured on a cell before and after aging of the cell. Differential entropy (dS) and differential enthalpy (dH) are obtained by taking the difference between the entropy/enthalpy data before and after aging at each SOC:

$$dS(SOC)=\Delta S(SOC)_{after\ aging}-\Delta S(SOC)_{before\ aging}\ \text{and}$$

$$dH(SOC)=\Delta H(SOC)_{after\ aging}-\Delta H(SOC)_{before\ aging}.$$

Three experiments were performed to examine the effects of accelerated aging on Lithium Ion Battery (LIB) cells, in particular with respect to the SOH of the cells. In the first experiment, aging of lithium ion cells was investigated due to thermal aging. Here, lithium ion cells were cycled between 2.75 V and 4.2 V at 10 mA (~C/4 rate) for four cycles then cells were charged to 4.2 V and stored in an oven at 60° C. and 70° C. for a period of time up to 8 weeks. At the end of each week, four cells were retrieved and tested by galvanostatic charge and discharge and thermodynamics measurements were performed.

Figure 20:
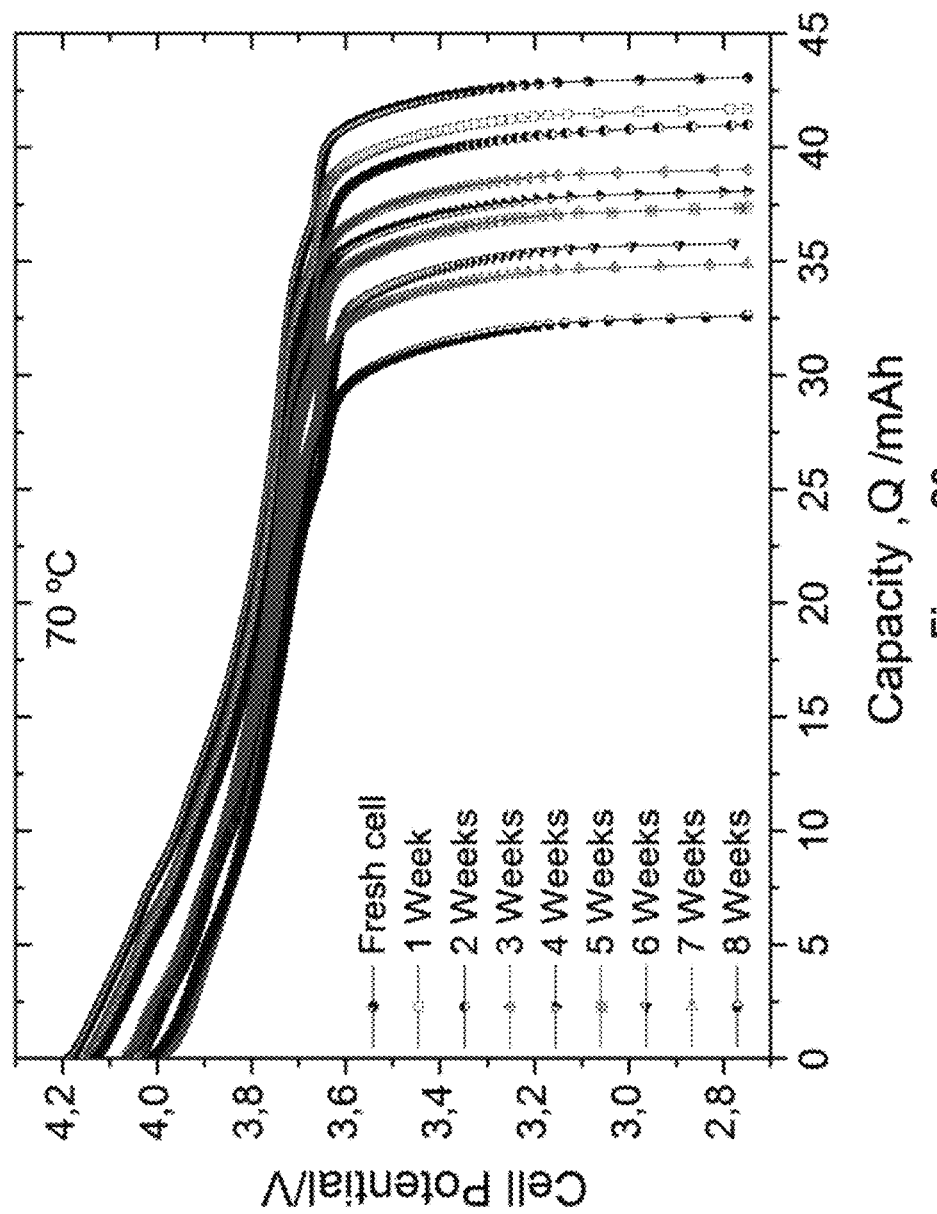

FIGS. 19 and 20 provide data illustrating the discharge profiles of cells aged at 60° C. and 70° C., respectively, over a period of 8 weeks. The data show a decrease in the capacity and cell potential as the cells age over time. FIGS. 21A and 21B provide a summary of the discharge characteristics after aging at 60° C. and 70° C., respectively. Here, $Q_d$ is discharge capacity, CL is Capacity loss, <E> is Average discharge voltage, $\mathcal{E}_d$ is discharge energy and is equal to $Q_d \times$ <E> and SOH is 100−CL.

Figure 22:
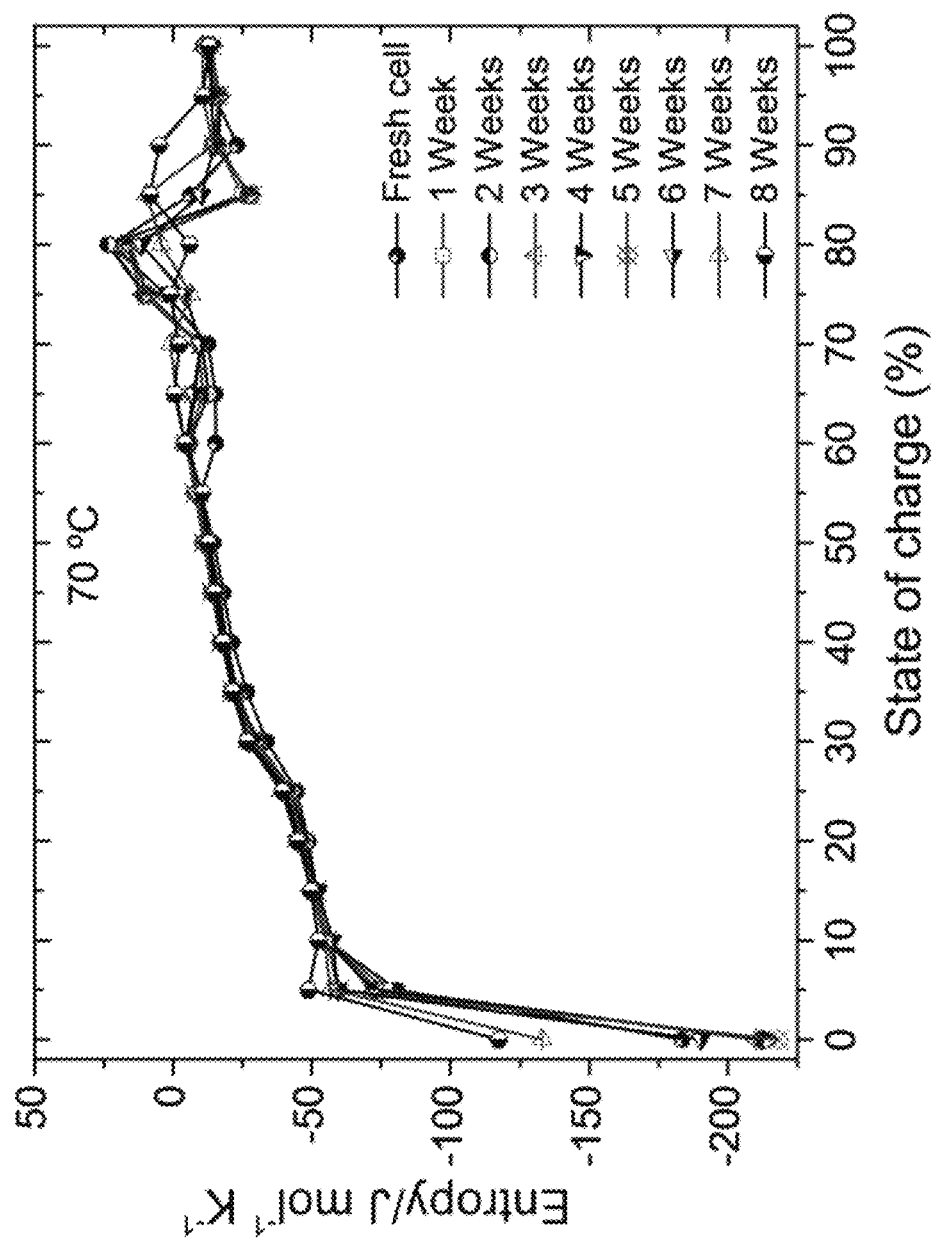
FIG. 22 provides data illustrating the entropy profiles of lithium ion cells aged at 70° C.
Figure 23:
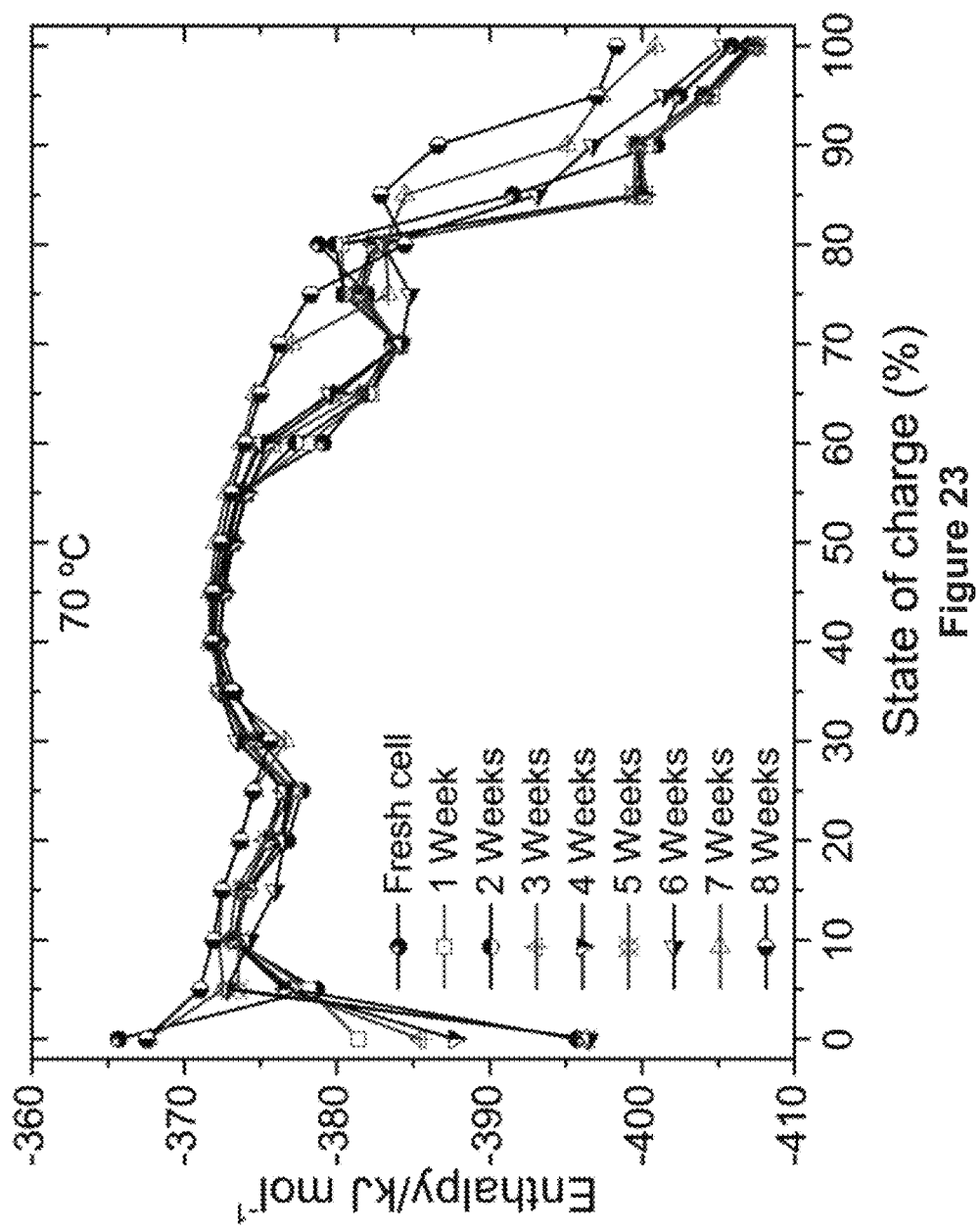
FIG. 23 provides data illustrating the enthalpy profiles of lithium ion cells aged at 70° C.
Figure 24:
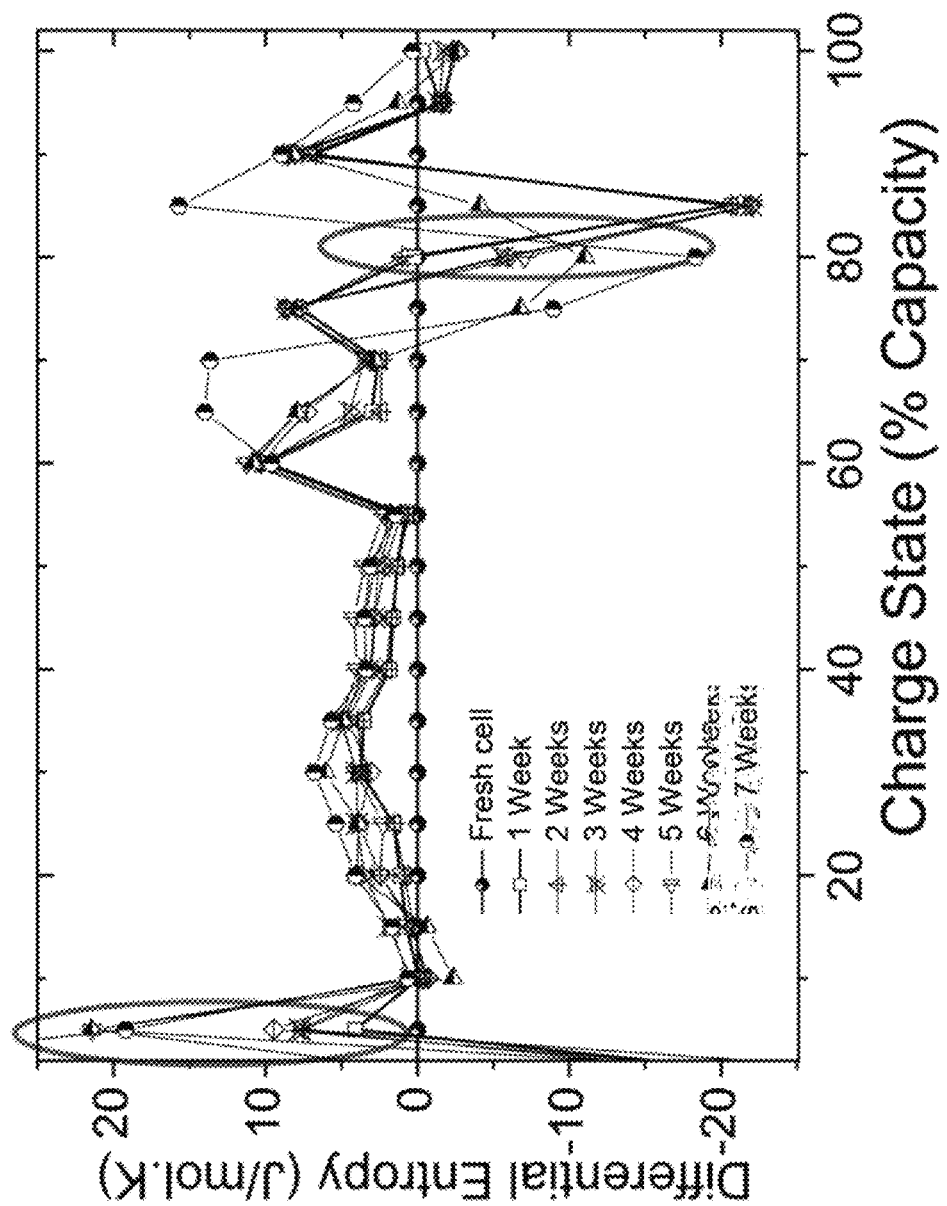
FIG. 24 provides data illustrating differential entropy profiles of lithium ion cells aged at 70° C.
Figure 25:
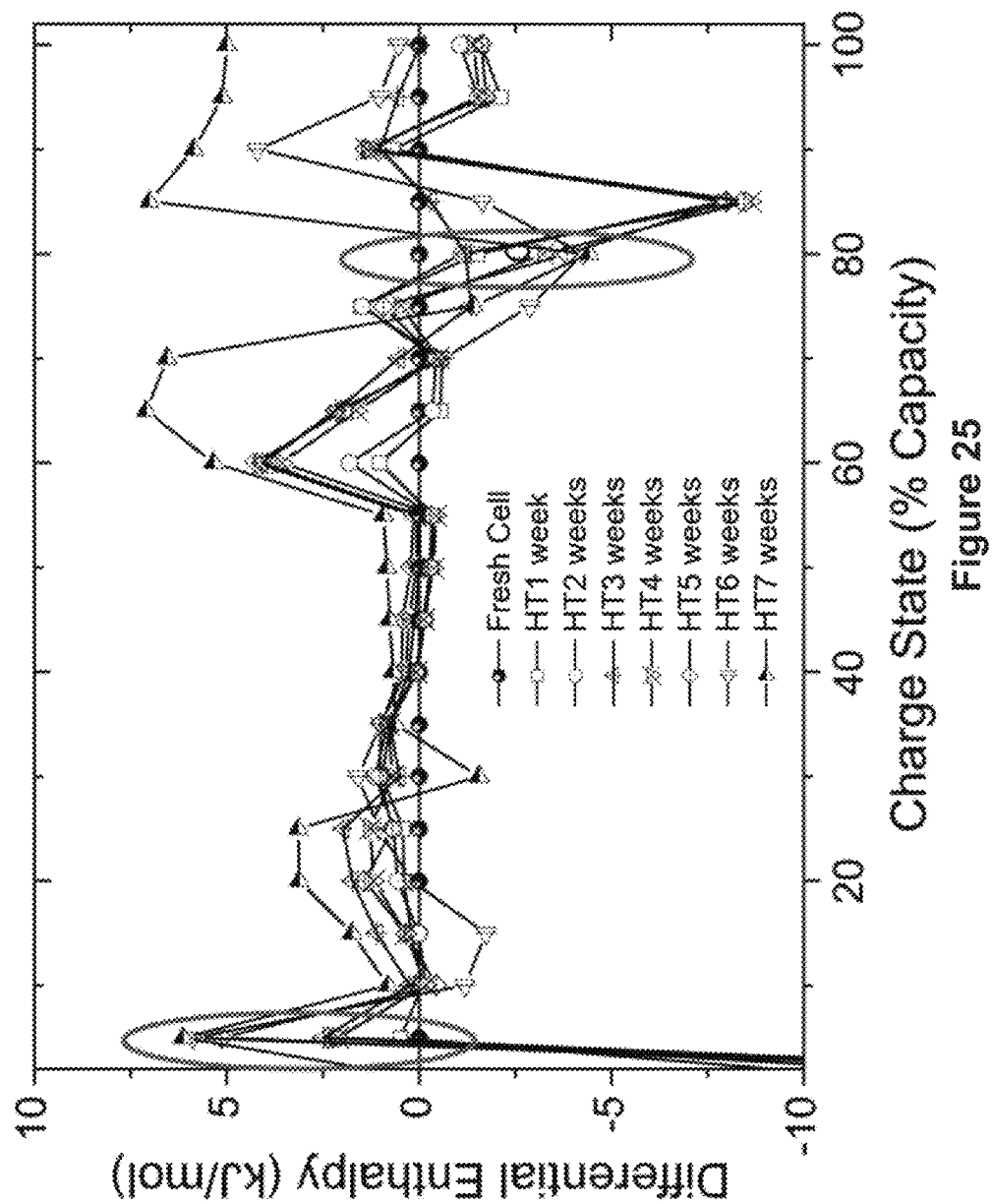
FIG. 25 provides data illustrating differential enthalpy profiles of lithium ion cells aged at 70° C.
Figure 26:
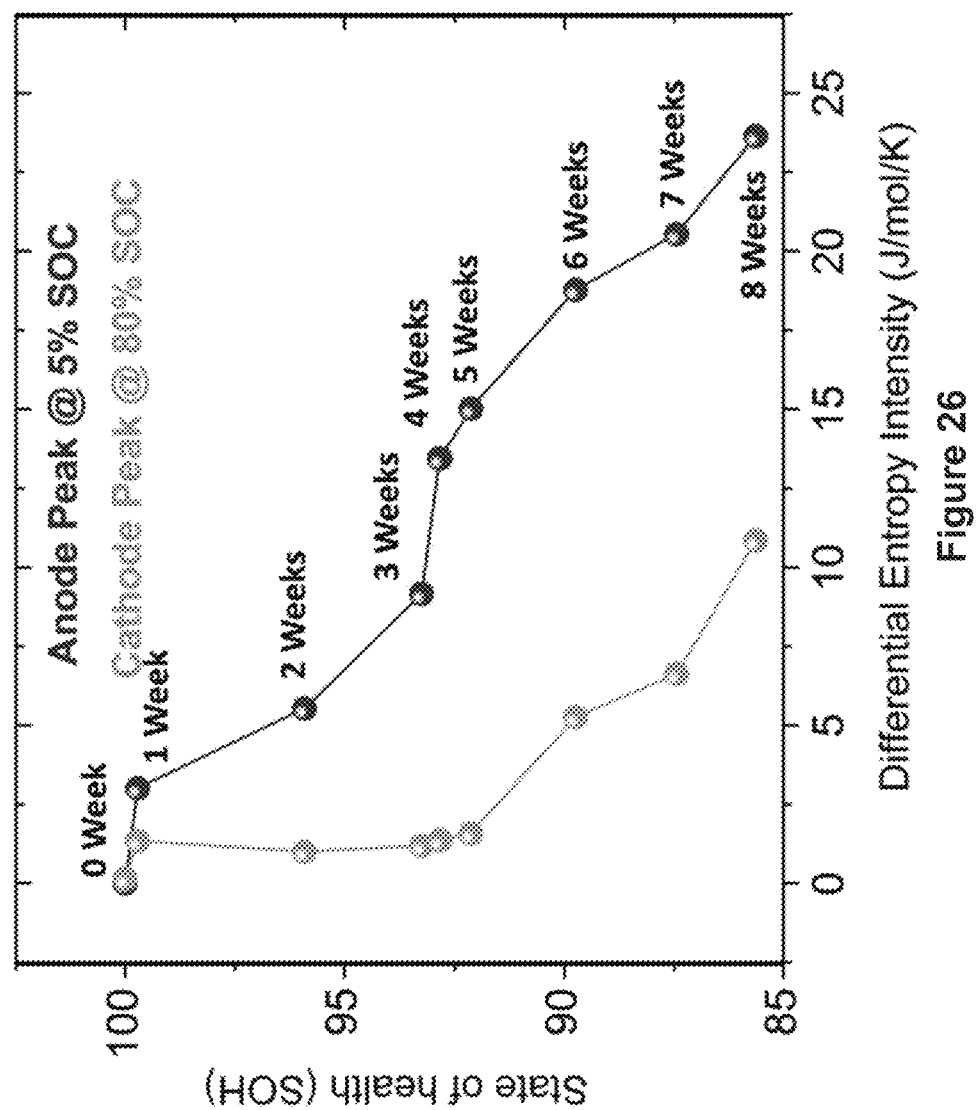
FIG. 26 illustrates data providing the state of health versus differential entropy of cells aged at 60° C.
Figure 27:
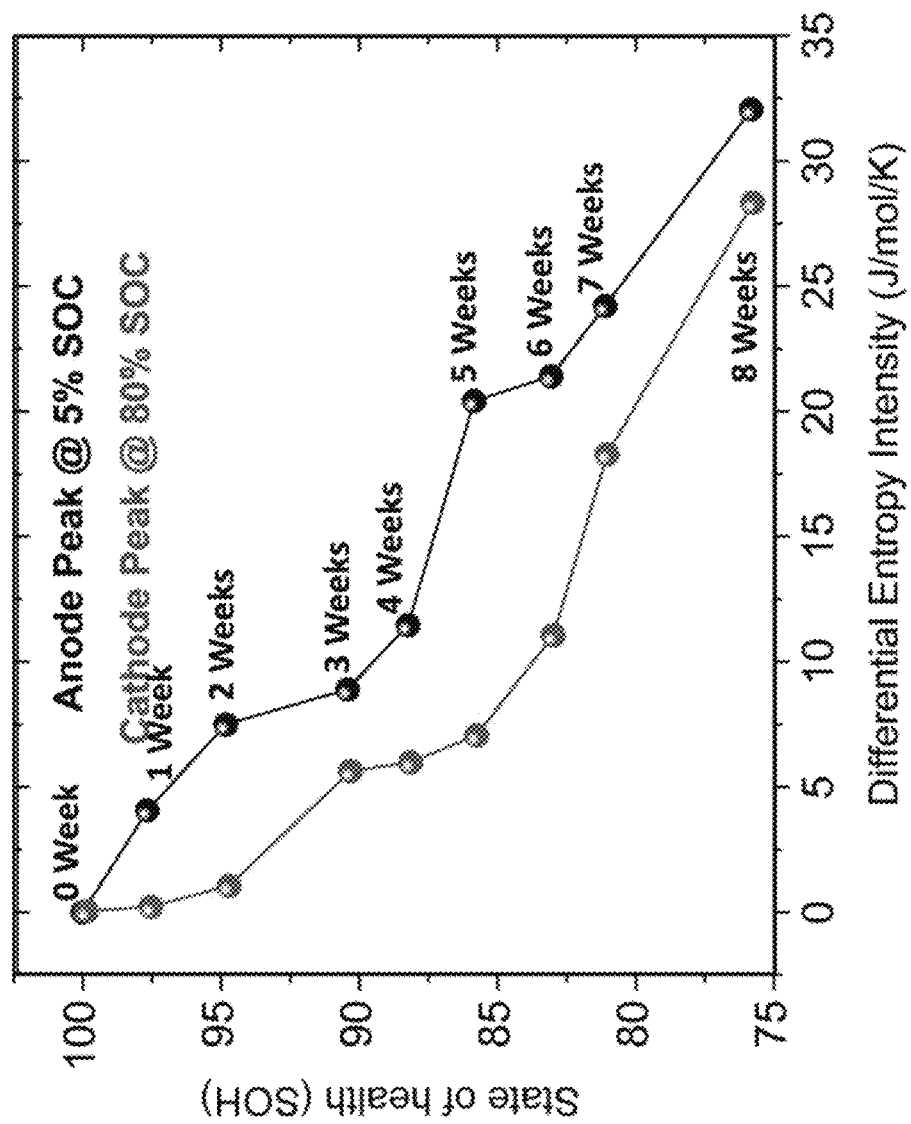
FIG. 27 illustrates data providing the state of health versus differential entropy of cells aged at 70° C.

FIG. 22 provides data illustrating the entropy profiles of LIB cells aged at 70° C. over a period of 8 weeks. FIG. 23 provides data illustrating the enthalpy profiles of LIB cells aged at 70° C. FIG. 24 provides data illustrating differential entropy profiles of LIB cells aged at 70° C. FIG. 25 provides data illustrating differential enthalpy profiles of LIB cells aged at 70° C. As indicated in the figures, a SOC of 5% and 80% are where dS and dH show the most significant changes in intensity. These states of charge correspond to changes in the anode and the cathode, respectively. Accordingly, 5% and 80% SOC will be used for all other aging methods to assess SOH vs. dS FIG. 26 illustrates data providing the state of health versus differential entropy of cells aged at 60° C., and shows a more rapid decrease in the state of health of the cathode over time compared to the anode. FIG. 27 illustrates data providing the state of health versus differential entropy of cells aged at 70° C., and again shows a more rapid decrease in the state of health of the cathode over time compared to the anode.

In the second experiment, aging of lithium ion cells was investigated due to overcharging. Coin cells rated at about 43 mAh were charged galvanostatically under a 10 mA rate up to a fixed cut-off voltage (COV) between 4.2 V and 4.9 V. A constant COV plateau was then applied for 1 hour. For each set of tests four new cells were used and the COV was increased by 0.1 V. Accordingly, different cells were charged to 4.2V, 4.3 V, 4.4 V and so on up to 4.9 V. The cells were then discharged to 2.75 V and charged to 4.2 V followed by a discharge to 2.75 V under 6 mA. The cells were then transferred to an electrochemical thermodynamic measurement system (BA-1000) to evaluate the cell's thermodynamics characteristics.

Figure 28:
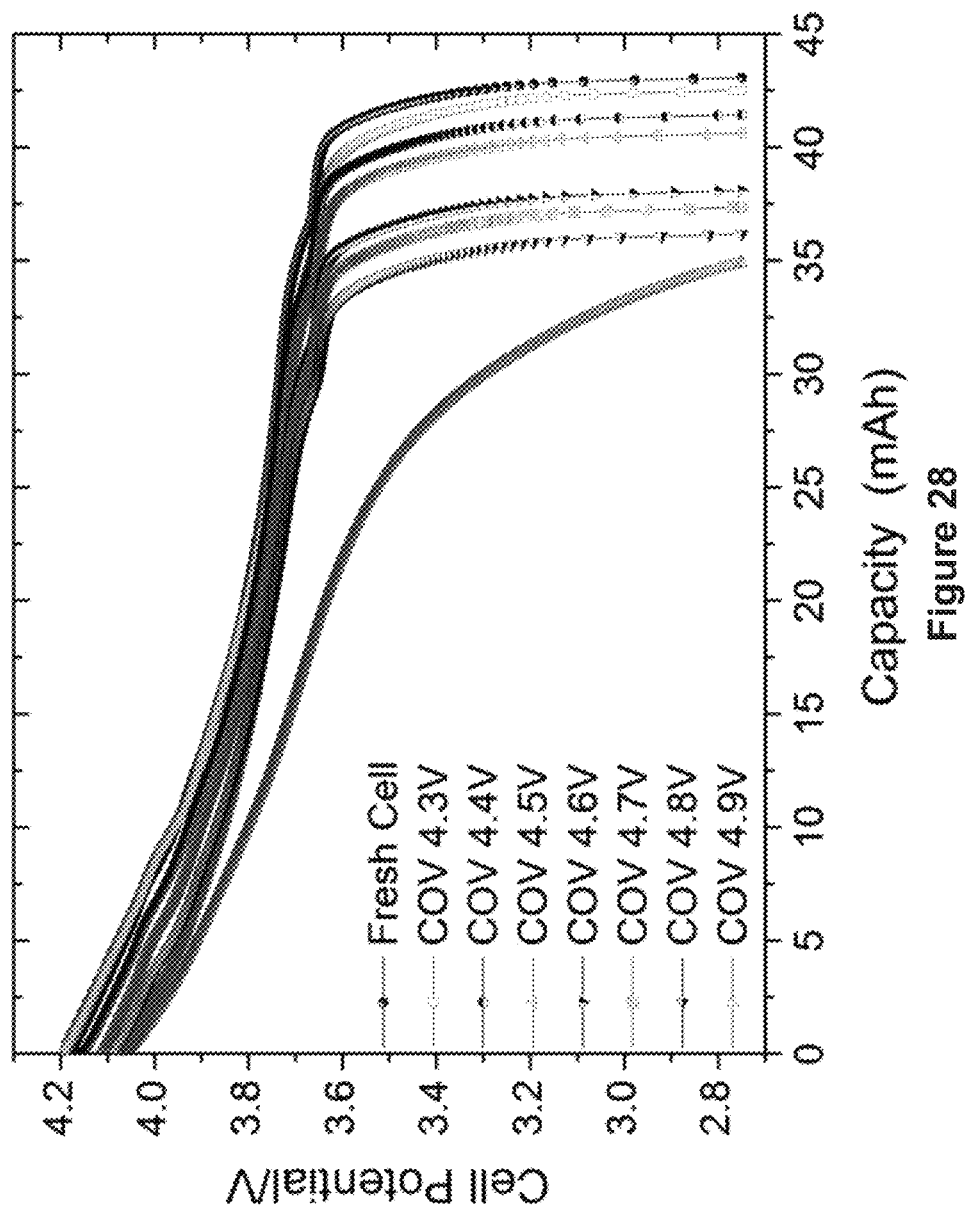
FIG. 28 provides data illustrating the discharge profile of cells overcharged at different cut-off voltages.
Figure 30:
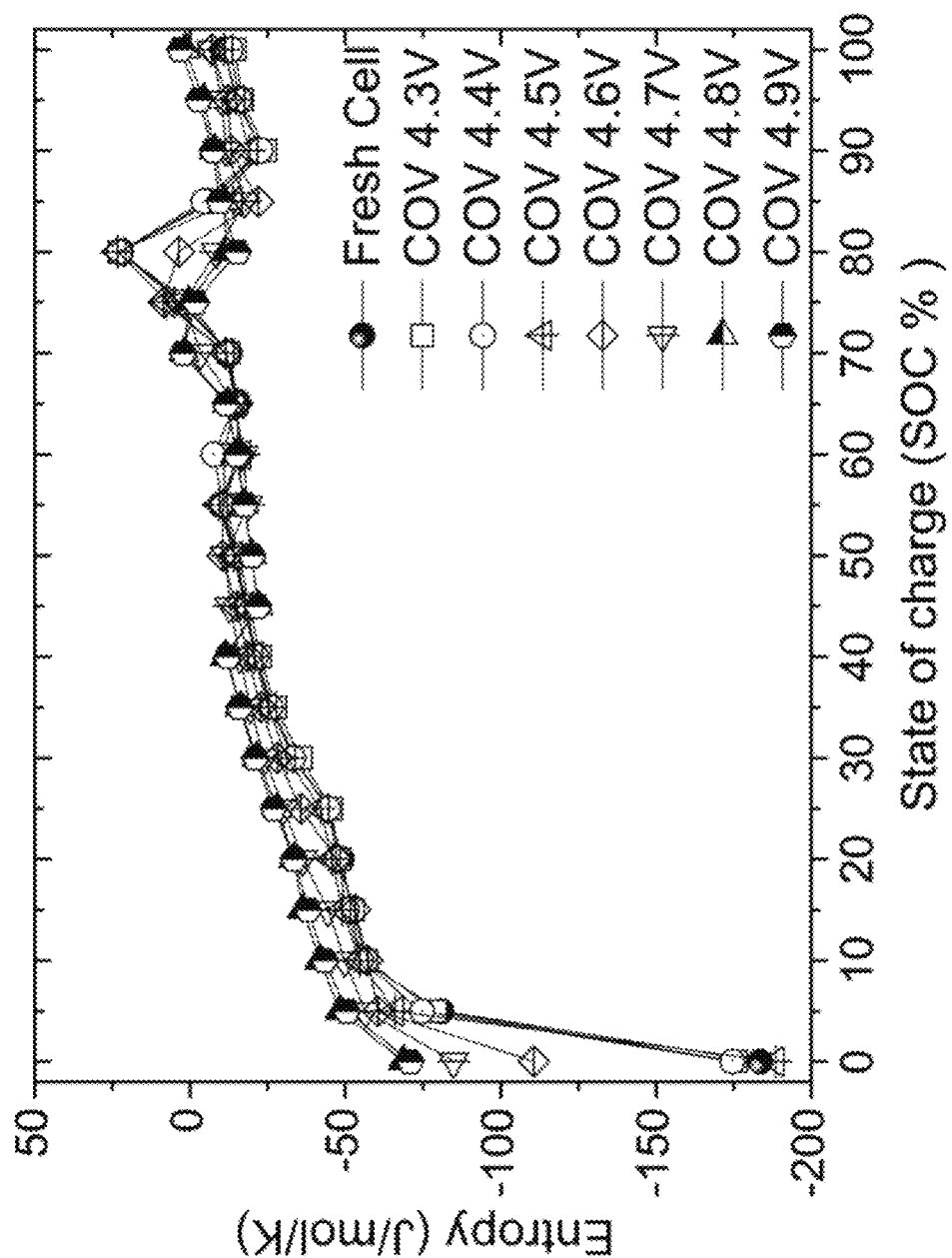
FIG. 30 provides data showing entropy profiles of electrochemical cells overcharged to different cut-off voltages.
Figure 31:
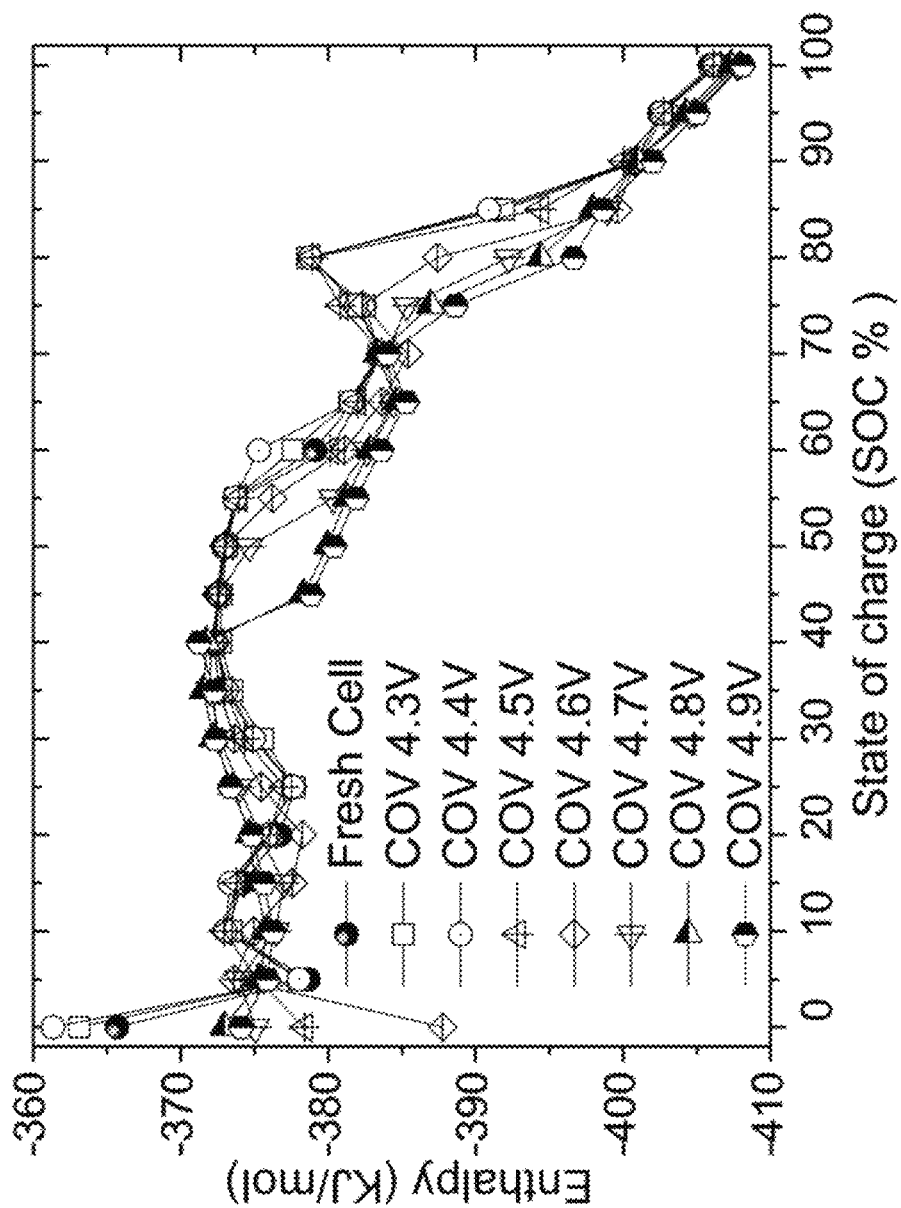
FIG. 31 provides data showing enthalpy profiles of electrochemical cells overcharged to different cut-off voltages.

FIG. 28 provides data illustrating the discharge profile of cells overcharged at different cut-off voltages (COV). Here, the cells generally exhibit a decrease in potential and capacity as the cells age by overcharging. FIG. 29 summarizes the discharge characteristics after overcharging at different COV. FIG. 30 provides data showing entropy profiles at different charge cut-off voltages. FIG. 31 provides data showing enthalpy profiles at different charge cut-off voltages.

Figure 32:
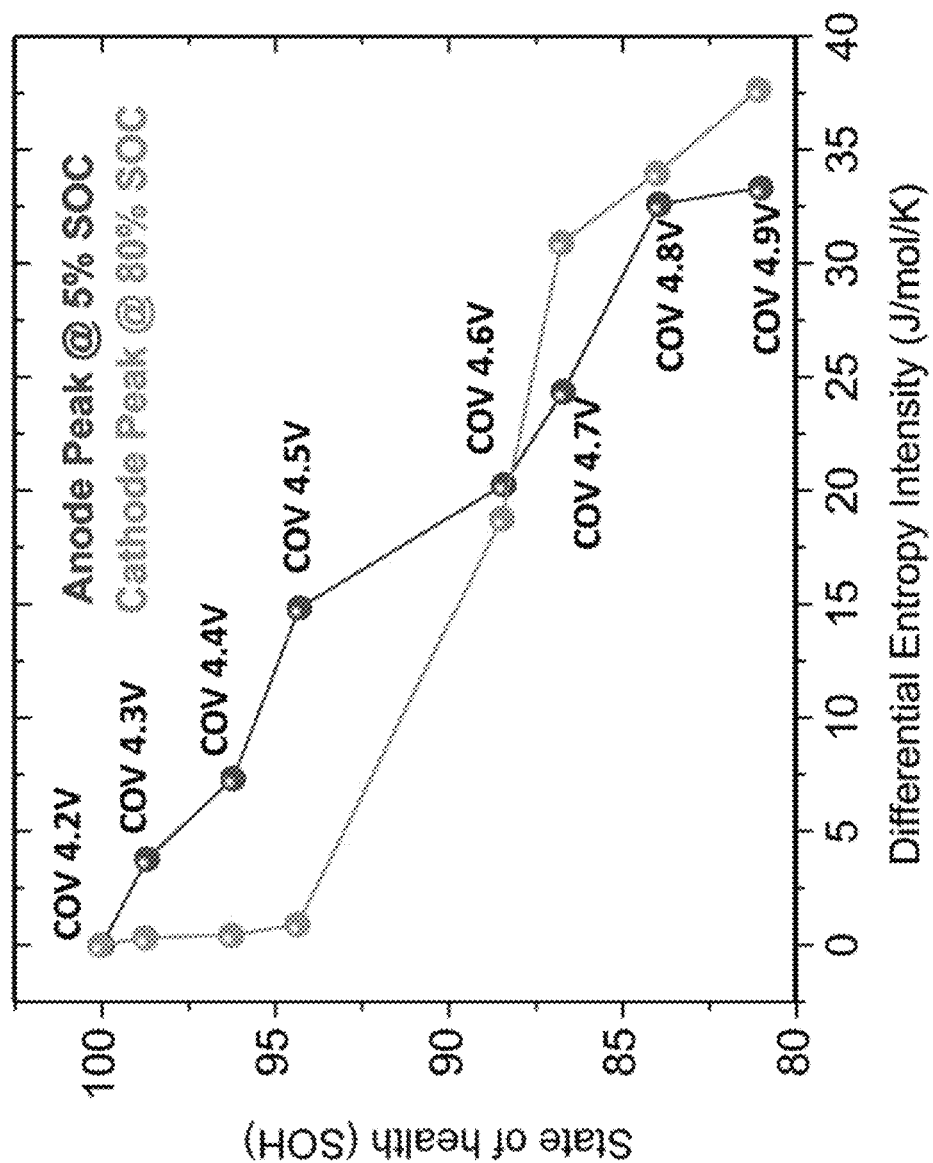
FIG. 32 illustrates data providing the state of health versus differential entropy of overcharged cells.

FIG. 32 illustrates data providing the state of health versus differential entropy of overcharged cells, and shows an initially more rapid decrease in the state of health of the cathode for amount of overcharge, but as the cells are more and more overcharged the state of health of the anode begins a more rapidly decrease than the cathode.

In the third experiment, aging of lithium ion was investigated due to long cycle aging. Here, four cells were cycled gavanostatically at 20 mA (~C/2 rate) between 2.75 V and 4.2 V at ambient temperature. After each completed 100 cycles; the cells were analyzed by galvanostatic cycling and thermodynamics measurements were performed. The same cells were then cycled again for an additional 100 cycles until reaching 1000 cycles.

Figure 34:
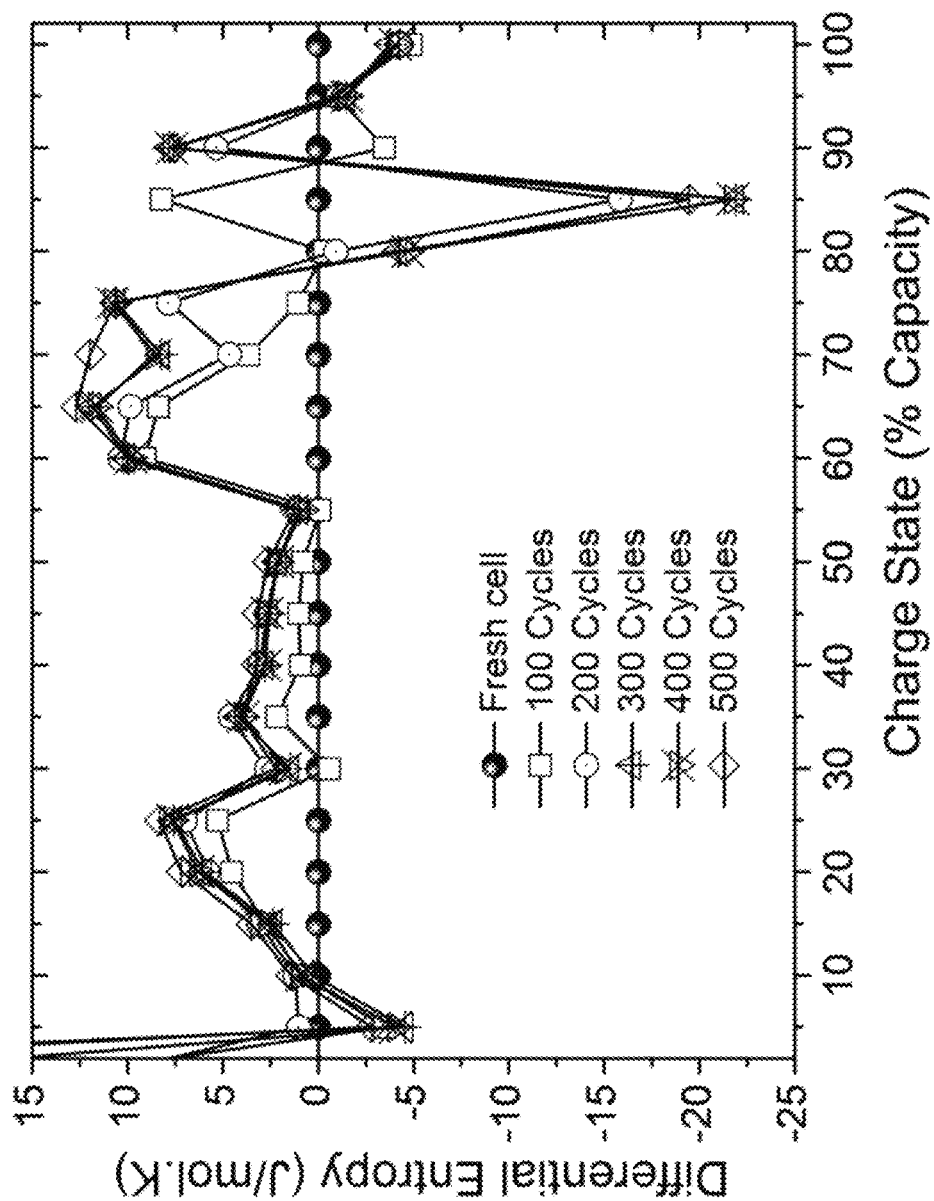
FIG. 34 provides data showing differential entropy profiles of cells after cycling.
Figure 35:
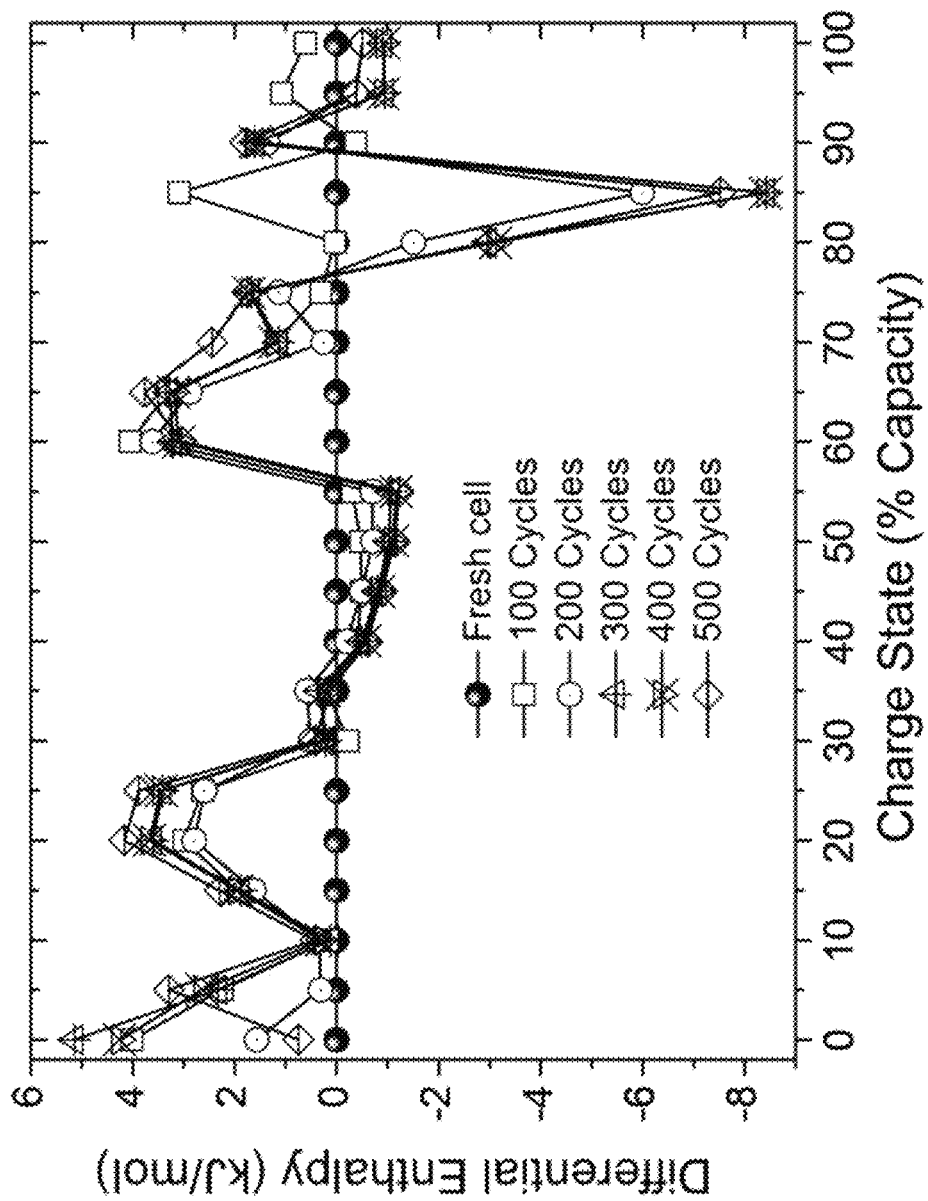
FIG. 35 provides data showing differential enthalpy profiles of cells after cycling.

FIG. 33 provides a summary of discharge characteristics of the cells after cycling. FIG. 34 provides data showing differential entropy profiles of cells after cycling. FIG. 35 provides data showing differential enthalpy profiles of cells after cycling.

Figure 36:
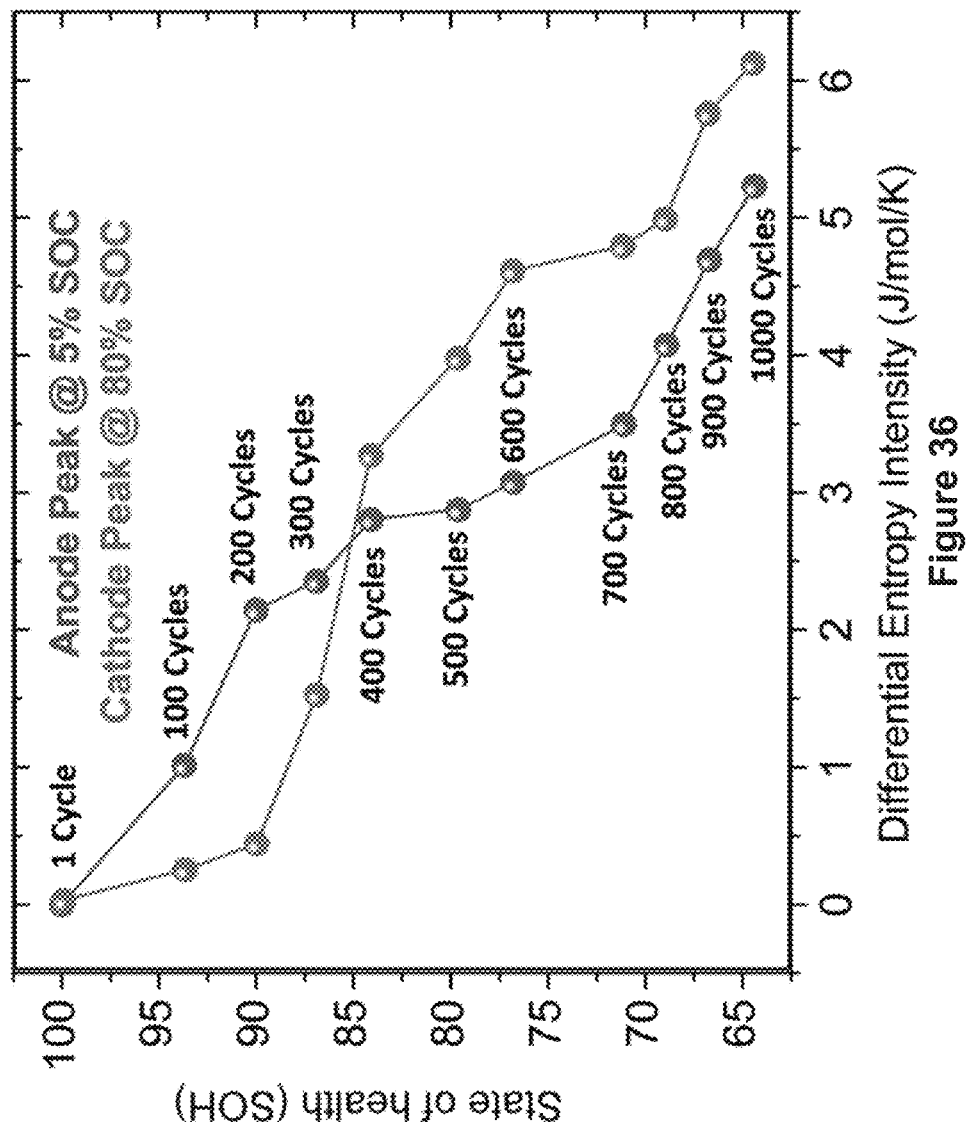
FIG. 36 illustrates data providing the state of health versus differential entropy of cycled cells.

FIG. 36 illustrates data providing the state of health versus differential entropy of cycled cells, and shows an initially more rapid decrease in the state of health of the cathode for as the number of cycles increases, but as the cells are further cycled, the state of health of the anode begins a more rapid decrease than the cathode.

As the above examples illustrate, regardless of the aging method (thermal, overcharge or cycling), dS and dH increase with aging rate. Capacity losses also increase with the aging rate. The cells' SOH, as determined from capacity loss using a simple relationship of SOH=100−CL, decrease with both dS and dH.

To investigate the effects of aging on the state of health of an electrochemical cell, experiments were performed on electrochemical cells. In particular, three cells were utilized to investigate the effects of aging on a self-heating rate (SHR) taking place within the cells, including a fresh cell, a cell thermally aged at 70° C. for 1 week and a cell thermally aged at 70° C. for 2 weeks. Accelerating Rate calorimetry (ARC) was used to measure the cells' self-heating rate at their initial 100% state of charge (4.2 V). The faster the self-heating rate, the lower the state of safety of the cell.

Figure 37:
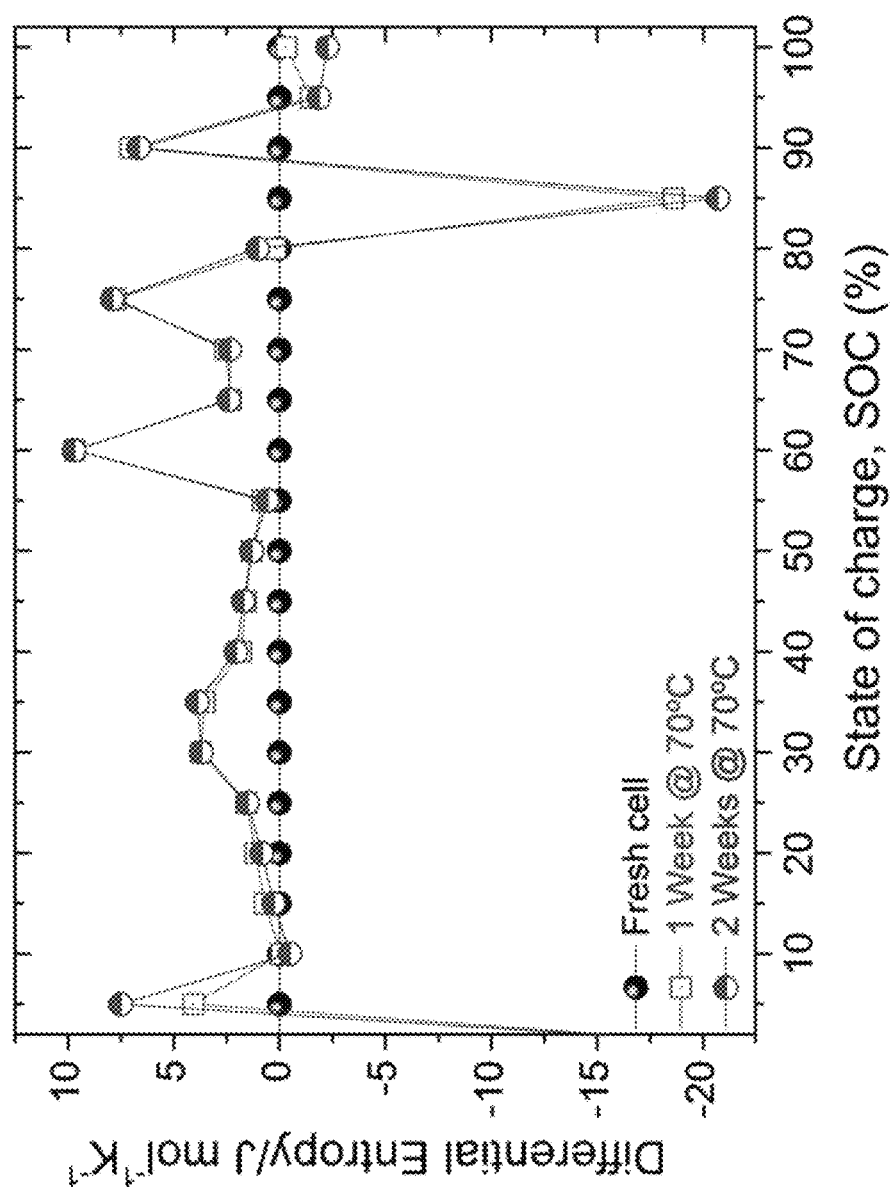
FIG. 37 provides data illustrating the differential entropy profile of the fresh and aged cells.
Figure 38:
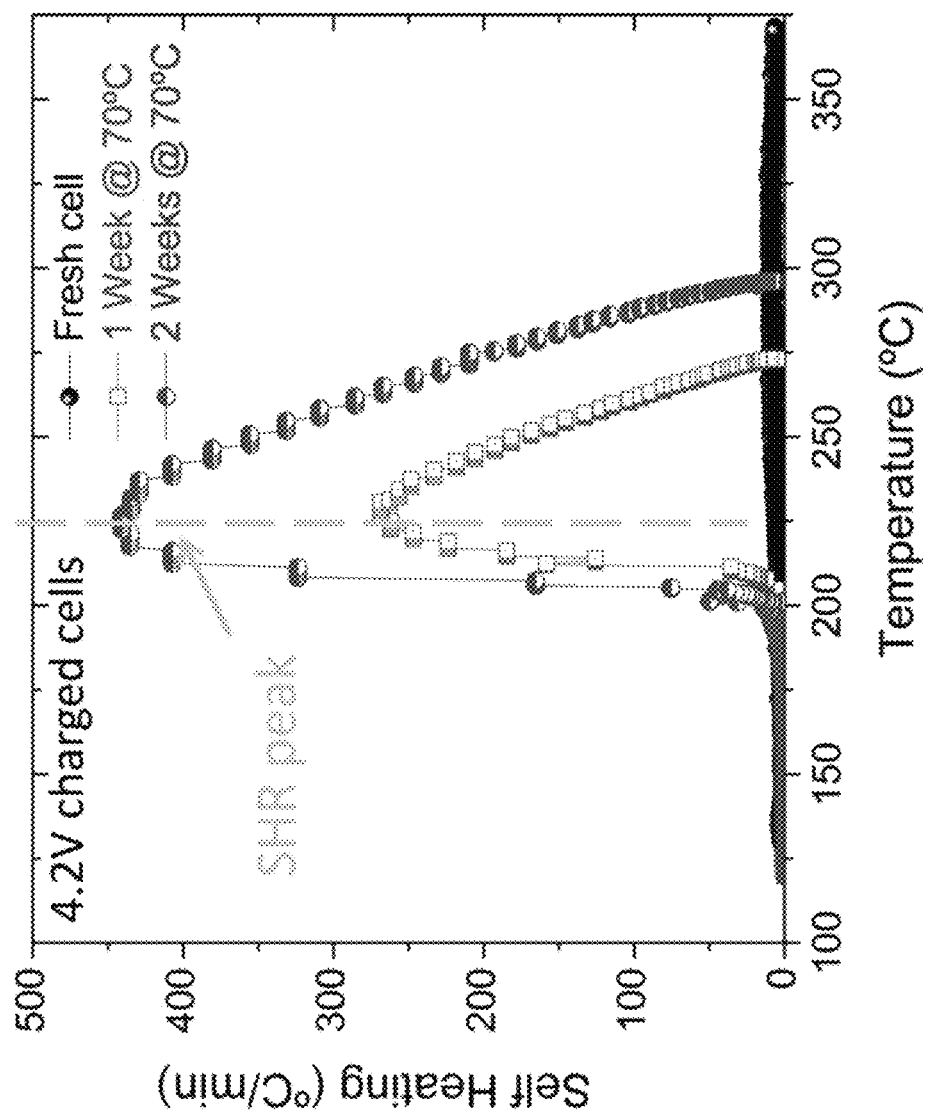
FIG. 38 provides data from accelerating rate calorimetry experiments showing the self-heating rate for fresh and aged cells.
Figure 39:
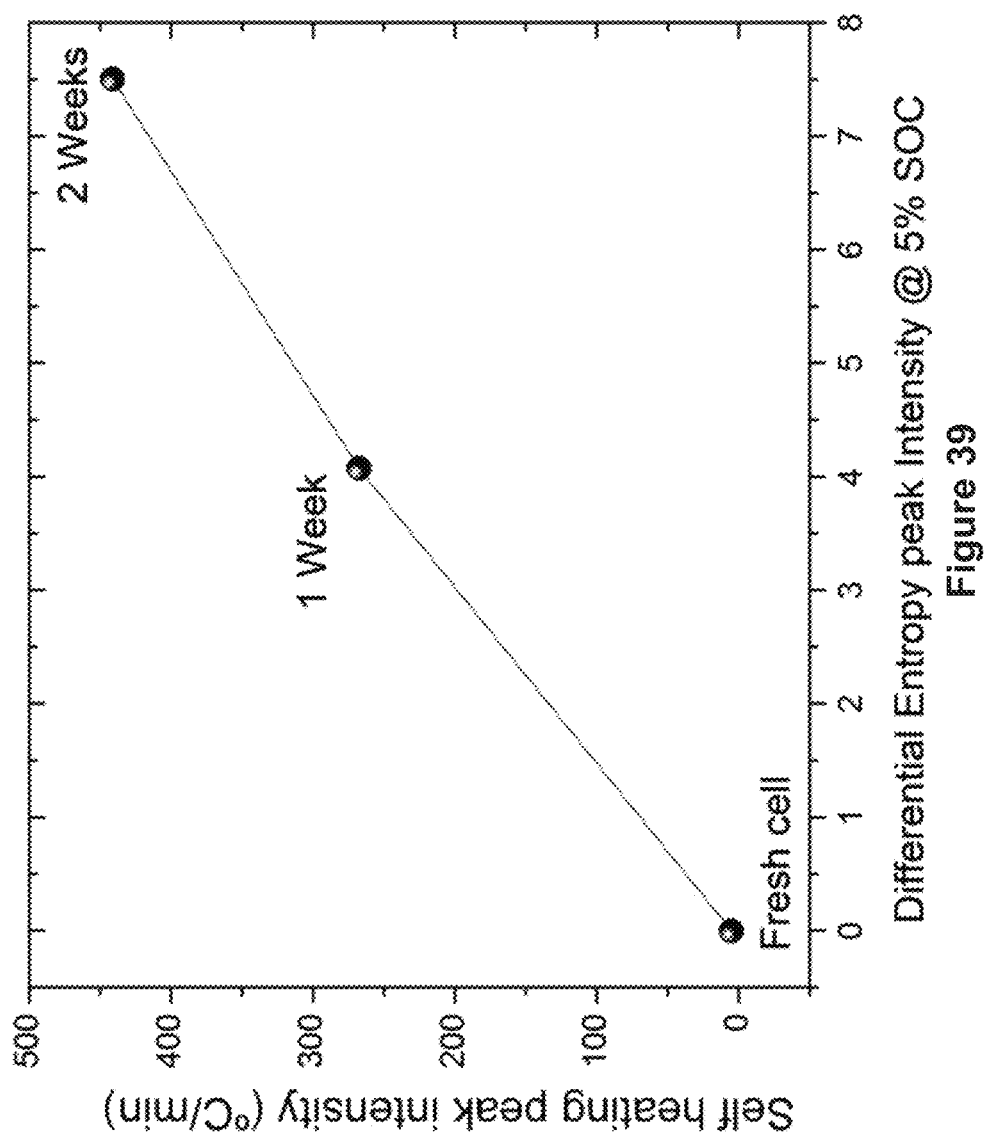
FIG. 39 illustrates data showing self-heating peak intensity plotted as a function of differential entropy peak intensity at 5% SOC.
Figure 40:
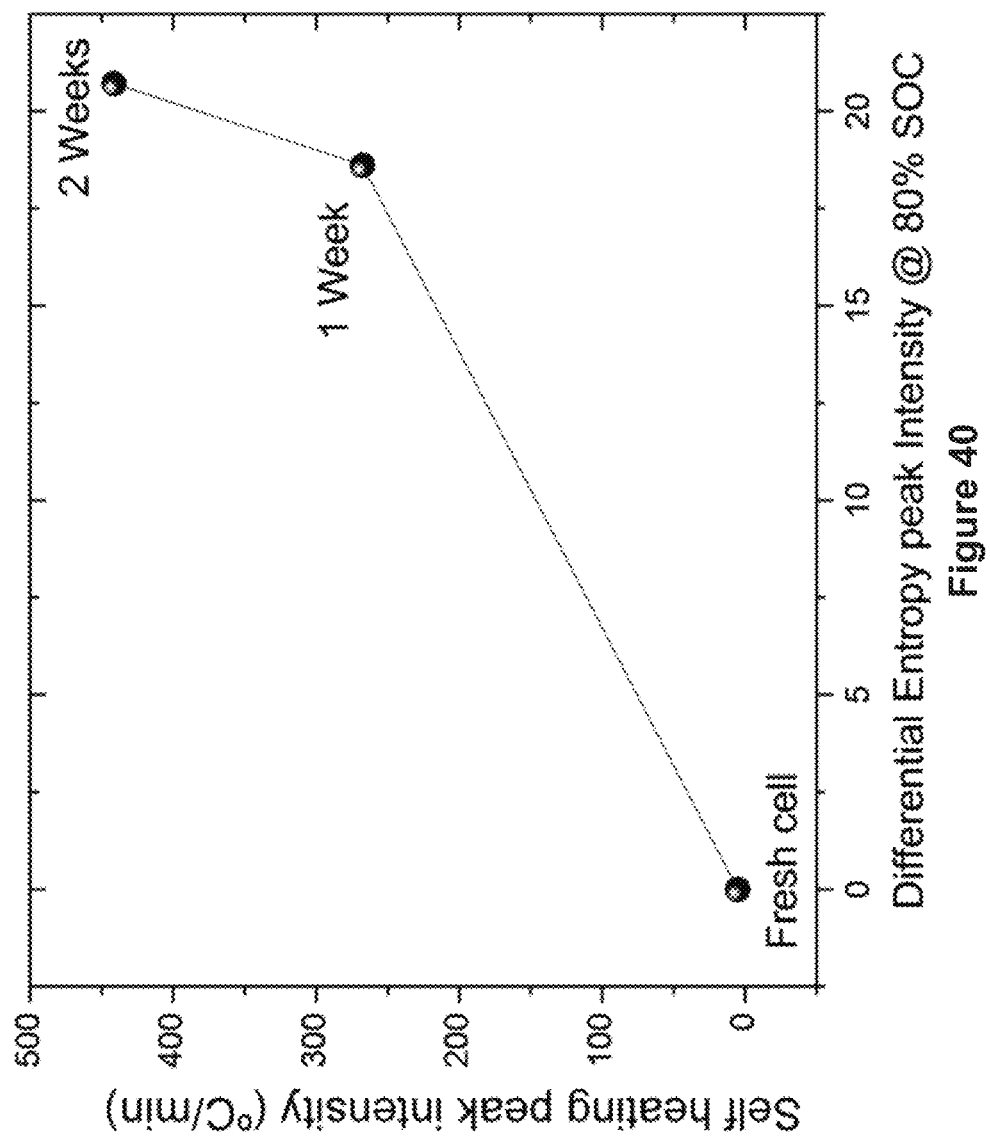
FIG. 40 illustrates data showing self-heating peak intensity as a function of differential entropy peak intensity at 80% SOC.

FIG. 37 provides data illustrating the differential entropy profile of the three cells. FIG. 38 provides data from the ARC experiments showing an increase in the self-heating rate for the 1 and 2 weeks aged cells. FIG. 39 illustrates data showing the self-heating peak intensity from the ARC experiments plotted as a function of differential entropy peak intensity at 5% SOC (corresponding to the anode). FIG. 40 illustrates data showing the self-heating peak intensity from the ARC experiments plotted as a function of differential entropy peak intensity at 80% SOC (corresponding to the cathode). The self-heating rate peak increases with the differential entropy at both 5 and 80% states of charge. Because the state of safety decreases with increasing self-heating rate, these data illustrate that the aging of the cells results in a lower state of safety, as determined using the ARC technique.

REFERENCES

Al Hallaj, S; Venkatachalapathy, R; Prakash, J; Selman, J R. Entropy changes due to structural transformation in the graphite anode and phase change of the LiCoO2 cathode. JOURNAL OF THE ELECTROCHEMICAL SOCIETY 147 (7): 2432-2436, 2000.

Al Hallaj, S; Prakash, J; Selman, J R, Characterization of commercial Li-ion batteries using electrochemical-calorimetric measurements. JOURNAL OF POWER SOURCES 87 (1-2), 186-194, 2000

Amatucci G G, Tarascon J M, Klein L C, CoO2, the end member of the LixCoO2 solid solution, JOURNAL OF THE ELECTROCHEMICAL SOCIETY, 143(3): 1114-1123, 1996.

Amatucci G G, Blyr A, Sigala C, Alfonse P, Tarascon J M, Surface treatments of Li1+xMn2−xO4 spinels for improved elevated temperature performance SOLID STATE IONICS Volume: 104 Issue: 1-2 Pages: 13-25 Published: December 1997.

Amatucci G, Du Pasquier A, Blyr A, Zheng T, Tarascon J M, The elevated temperature performance of the LiMn2O4/C system: failure and solutions ELECTROCHIMICA ACTA 45 (1-2): 255-271, 1999.

Andre et al., Engineering Applications of Artificial Intelligence 26 (2013) 951-961.

Attidekou, P S; Garcia-Alvarado, F; Connor, P A; Irvine, J T S. Thermodynamic aspects of the reaction of lithium with SnP2O7 based positive electrodes. JOURNAL OF THE ELECTROCHEMICAL SOCIETY 154 (3): A217-A220, 2007.

Aurbach D, Levi M D, Gamulski K, Markovsky B, Salitra G, Levi E, Heider U, Heider L, Oesten R, Capacity fading of LixMn2O4 spinel electrodes studied by XRD and electroanalytical techniques, JOURNAL OF POWER SOURCES, 81: 472-479, 1999.

Aydinol, M K; Kohan, A F; Ceder, G; Cho, K; Joannopoulos, J. Ab initio study of lithium intercalation in metal oxides and metal dichalcogenides. PHYSICAL REVIEW B 56 (3): 1354-1365, 1997.

Baddour, R; Pereiraramos, J P; Messina, R; Perichon, J. A Thermodynamic, Structural and Kinetic-Study of the Electrochemical Lithium Intercalation Into the Xerogel V2O5.1.6 H2O In A Propylene Carbonate Solution. Journal of Electroanalytical Chemistry 314 (1-2): 81-101, 1991

Barbato, S; Gautier, J L. Hollandite cathodes for lithium ion batteries. 2. Thermodynamic and kinetics studies of lithium insertion into BaMmn7O16 (M=Mg, Mn, Fe, Ni). ELECTROCHIMICA ACTA 46 (18): 2767-2776, 2001.

Barker, J; West, K; Saidi, Y; Pynenburg, R; Zachauchristiansen, B; Koksbang, R. Kinetics and Thermodynamics of the Lithium Insertion Reaction in Spinel Phase LixMn2O4. Journal of Power Sources 54 (2): 475-478, 1995.

G. Bathia, R. K. Aggarwal, N. Punjabi and O. P. Bahl, J. Mater. Science 32, 135 (1997).

Benco, L; Barras, J L; Atanasov, M; Daul, C; Deiss, E. First principles calculation of electrode material for lithium intercalation batteries: TiS2 and LiTi2S4 cubic spinel structures. JOURNAL OF SOLID STATE CHEMISTRY 145 (2): 503-510, 1999.

D. M. Bernardi et al., J. Power Sources 196 (2011) 412-427.

Billaud D, Henry F X, Lelaurain M, Willmann P Revisited structures of dense and dilute stage II lithium-graphite intercalation compounds. JOURNAL OF PHYSICS AND CHEMISTRY OF SOLIDS 57 (6-8): 775-781, 1996.

Botte, G G; Subramanian, V R; White, R E. Mathematical modeling of secondary lithium batteries. ELECTROCHIMICA ACTA 45 (15-16): 2595-2609, 2000.

Carlier, D; Van der Ven, A; Delmas, C; Ceder, G. 2003. First-principles investigation of phase stability in the O-2-LiCoO2 system. CHEMISTRY OF MATERIALS 15 (13): 2651-2660.

Ceder, G; Kohan, A F; Aydinol, M K; Tepesch, P D; Van der Ven, A. Thermodynamics of oxides with substitutional disorder: A microscopic model and evaluation of important energy contributions. JOURNAL OF THE AMERICAN CERAMIC SOCIETY 81 (3): 517-525, 1998.

Ceder, G; Van der Ven, A. Phase diagrams of lithium transition metal oxides: investigations from first principles. ELECTROCHIMICA ACTA 45 (1-2): 131-150, 1999.

Chen Z H, Lu Z H, Dahn J R, Staging phase transitions in LixCoO2, JOURNAL OF THE ELECTROCHEMICAL SOCIETY, 149 (12): A1604-A1609, 2002.

Chen, Z W; Xuan, C; Ying, Z; Yong, Y. First principle investigation of positive electrode material for lithium ion batteries. RARE METAL MATERIALS AND ENGINEERING 32 (9): 693-698, 2003.

M. Coleman, C. K. Lee, C. Zhu and W. G. Hurley, "State-of-charge determination from EMF voltage estimation: using impedance, terminal voltage and current for lead-acid and lithium-ion batteries," IEEE Trans. Ind. Electron., Vol. 54, pp. 2250-2257, 2007.

Deiss, E; Wokaun, A; Barras, J L; Daul, C; Dufek, P. Average voltage, energy density, and specific energy of lithium-ion batteries—Calculation based on first principles. JOURNAL OF THE ELECTROCHEMICAL SOCIETY 144 (11): 3877-3881, 1997.

Doi, T; Fukudome, H; Okada, S; Yamaki, J I. Computer simulation of a porous positive electrode for lithium batteries. JOURNAL OF POWER SOURCES 174 (2): 779-783, 2007.

Eddahech et al., Electrical Power and Energy Systems 42 (2012) 487-494.

Filhol, J. -S., Combelles, C., Yazami, R., Doublet, M. -L., Phase diagrams for systems with low free energy variation: A coupled theory/experiments method applied to Li-graphite, JOURNAL OF PHYSICAL CHEMISTRY C, 112 (10): 3982-3988, 2008.

Rosalind E. Franklin, Crystallite Growth in Graphitizing and Non-Graphitizing Carbons, Proceedings of the Royal Society of London. Series A, Mathematical and Physical Sciences, Vol. 209, No. 1097 (Oct. 23, 1951), pp. 196-218.

Fujiwara, H; Ueda, Y; Awasthi, A; Krishnamurthy, N; Garg, S P. Determination of standard free energy of formation for niobium silicides by EMF measurements. JOURNAL OF THE ELECTROCHEMICAL SOCIETY 150 (8): J43-J48, 2003.

Funahashi, A; Kida, Y; Yanagida, K; Nohma, T; Yonezu, I. Thermal simulation of large-scale lithium secondary batteries using a graphite-coke hybrid carbon negative electrode and lini0.7Co0.3O2 positive electrode. JOURNAL OF POWER SOURCES 104 (2): 248-252, 2002.

Gabrisch H, Yazami R, Fultz B, Hexagonal to cubic spinel transformation in lithiated cobalt oxide—TEM investigation, JOURNAL OF THE ELECTROCHEMICAL SOCIETY, 151 (6): A891-A897, 2004.

Gabrisch, H.; Yi, T.; Yazami, R., Transmission electron microscope studies of LiNi1/3Mn1/3Co1/3/O2 before and after long-term aging at 70 degrees C., Electrochemical and Solid-State Letters Volume: 11(7): 119-24, 2008.

Garcia-Belmonte, G; Garcia-Canadas, J; Bisquert, J. Correlation between volume change and cell voltage variation with composition for lithium intercalated amorphous films. JOURNAL OF PHYSICAL CHEMISTRY B 110 (10): 4514-4518, 2006.

Gautier J L, Meza E, Silva E, Lamas C, Silva C, Effect of the ZnNiyMn2-yO4 ($0<=y<=1$) spinel composition on electrochemical lithium insertion, Journal of Solid State Electrochemistry, 1 (2): 126-133, 1997.

Gong, J B; Wu, H Q. Electrochemical intercalation of lithium species into disordered carbon prepared by the heat-treatment of poly (p-phenylene) at 650 degrees C. for anode in lithium-ion battery. ELECTROCHIMICA ACTA 45 (11): 1753-1762, 2000.

Graetz J, Hightower A, Ahn C C, Yazami R, Rez P, Fultz B, Electronic structure of chemically-delithiated LiCoO2 studied by electron energy-loss spectrometry JOURNAL OF PHYSICAL CHEMISTRY B Volume: 106 (6): 1286-1289, 2002.

Guzman, G; Yebka, B; Livage, J; Julien, C. Lithium intercalation studies in hydrated molybdenum oxides. SOLID STATE IONICS 86-8: 407-413, Part 1. 1996.

Hallstedt, B; Kim, O. Thermodynamic assessment of the Al—Li system. INTERNATIONAL JOURNAL OF MATERIALS RESEARCH 98 (10): 961-969, 2007.

Hill I R, Sibbald A M, Donepudi V S, Adams W A, Donaldson G J, Microcalorimetric studies on lithium thionyl chloride cells—temperature effects between 25-degrees-C and −40-degrees-C, Journal of Power Sources, 39 (1): 83-94, 1992.

Hong, J S; Maleki, H; Al Hallaj, S; Redey, L; Selman, J R. Electrochemical-calorimetric studies of lithium-ion cells. JOURNAL OF THE ELECTROCHEMICAL SOCIETY 145 (5): 1489-1501, 1998.

Hong, J S; Selman, J R. Relationship between calorimetric and structural characteristics of lithium-ion cells—I. Thermal analysis and phase diagram. JOURNAL OF THE ELECTROCHEMICAL SOCIETY 147 (9): 3183-3189, 2000.

Huang H, Vincent C A, Bruce P G, Correlating capacity loss of stoichiometric and nonstoichiometric lithium manganese oxide spinel electrodes with their structural integrity JOURNAL OF THE ELECTROCHEMICAL SOCIETY, 146 (10): 3649-3654, 1999.

Huang, Q; Yan, M M; Jiang, Z Y. Thermal study on single electrodes in lithium-ion battery. JOURNAL OF POWER SOURCES 156 (2): 541-546, 2006.

Huggins, R A. Lithium alloy negative electrodes. JOURNAL OF POWER SOURCES 82: 13-19, 1999.

Idemoto, Y; Ogawa, S; Uemura, Y; Koura, N. Thermodynamic stability and cathode performance of Li1+xmn2−xo4 as a cathode active material for lithium secondary battery. JOURNAL OF THE CERAMIC SOCIETY OF JAPAN 108 (9): 848-853, 2000.

Idemoto, Y; Ogawa, S; Koura, N; Udagawa, K. Thermodynamic stability and cathode performance of limn2−xmgxo4 as cathode active material for the lithium secondary battery. ELECTROCHEMISTRY 68 (6): 469-473, 2000.

Idemoto, Y; Sakaya, T; Koura, N., Dependence of properties, crystal structure and electrode characteristics on Li content for LixCo1/3Ni1/3Mn1/3O2+delta as a cathode active material for Li secondary battery. ELECTROCHEMISTRY 74 (9): 752-757, 2006.

Joo, J H; Bae, Y C; Sun, Y K. Phase behaviors of solid polymer electrolytes/salt system in lithium secondary battery by group-contribution method: The pressure effect. POLYMER 47 (1): 211-217, 2006.

Joo, J H; Bae, Y C. Molecular thermodynamics approach for phase behaviors of solid polymer electrolytes/salt system in lithium secondary battery on the nonrandom mixing effect: Applicability of the group-contribution method. POLYMER 47 (20): 7153-7159, 2006.

Kalikmanov, V I; de Leeuw, S W. Role of elasticity forces in thermodynamics of intercalation compounds: Self-consistent mean-field theory and Monte Carlo simulations. JOURNAL OF CHEMICAL PHYSICS 116 (7): 3083-3089, 2002.

H. Kataoka, Y. Saito, O. Omae, J. Suzuki, K. Sekine, T. Kawamura and T. Takamurae, *Electrochem. and Solid-State Lett.*, 5, A10 (2002).

Kim, S W; Pyun, S I. Thermodynamic and kinetic approaches to lithium intercalation into a Li1-delta Mn2O4 electrode using Monte Carlo simulation. ELECTROCHIMICA ACTA 46 (7): 987-997, 2001.

Kobayashi, H; Arachi, Y; Kageyama, H; Tatsumi, K. Structural determination of Li1−yNi0.5Mn0.5O2 (y=0.5) using a combination of Rietveld analysis and the maximum entropy method. JOURNAL OF MATERIALS CHEMISTRY 14 (1): 40-42, 2004.

Korovin, N V. Electrochemical intercalation into cathodic materials: Electrode potentials. RUSSIAN JOURNAL OF ELECTROCHEMISTRY 34 (7): 669-675, 1998.

Koudriachova, M V; Harrison, N M; de Leeum, S W. First principles predictions for intercalation behaviour. SOLID STATE IONICS 175 (1-4): 829-834, 2004.

Kuhn, A; Diaz-Carrasco, P; de Dompablo, M E A Y; Garcia-Alvarado, F. On the synthesis of ramsdellite LiTiMO4 (M=Ti, V, Cr, Mn, Fe): An experimental and computational study of the spinel-ramsdellite transformation. EUROPEAN JOURNAL OF INORGANIC CHEMISTRY (21): 3375-3384, 2007.

Kuko T and Hibino M., Theoretical dependence of the free energy and chemical potential upon composition in intercalation systems with repulsive interaction between guest ions, Electrochem. Acta 43(7):781-789, 1998

Kumagai, N; Fujiwara, T; Tanno, K; Horiba, T. Thermodynamic And Kinetic-Studies of Electrochemical Lithium Insertion Into Quaternary Li—Mn—V—O Spinel As Positive Materials For Rechargeable Lithium Batteries. Journal of The Electrochemical Society 140 (11): 3194-3199, 1993.

Kumagai, N; Yu, A S; Kumagai, N; Yashiro, H. Electrochemical intercalation of lithium into hexagonal tungsten trioxide. THERMOCHIMICA ACTA 299 (1-2): 19-25, 1997.

Kumagai, N; Yu, A S; Yashiro, H. Thermodynamics and kinetics of electrochemical intercalation of lithium into Li0.50WO3.25 with a hexagonal tungsten bronze structure. SOLID STATE IONICS 98 (3-4): 159-166, 1997.

Kumagai, N; Koishikawa, Y; Komaba, S; Koshiba, N., Thermodynamics and kinetics of lithium intercalation into Nb2O5 electrodes for a 2 V rechargeable lithium battery. JOURNAL OF THE ELECTROCHEMICAL SOCIETY 146 (9): 3203-3210, 1999

K. Kumaresan, G. Sikha; R. E. White, JOURNAL OF THE ELECTROCHEMICAL SOCIETY 155 (2008) A164-A171.

Lee, H H; Wan, C C; Wang, Y Y. Identity and thermodynamics of lithium intercalated in graphite. JOURNAL OF POWER SOURCES 114 (2): 285-291, 2003.

M. Letellier, F. Chevallier, F. Béguin, E. Frackowiak, J-N. Rouzau, *J. Phys. and Chem. of Solids* 65, 245 (2004).

Limthongkul, P; Jang, Y I; Dudney, N J; Chiang, Y M. Electrochemically-driven solid-state amorphization in lithium-metal anodes. JOURNAL OF POWER SOURCES 119: 604-609, 2003.

Lin et al., IEEE Transactions on Industrial Informatics, 9:2 (2013) 679-685.

Lu, W Q; Yang, H; Prakash, J. Determination of the reversible and irreversible heats of LiNi(0.8)Co(0.2)O(2)/mesocarbon microbead Li-ion cell reactions using isothermal microcalorimetery. ELECTROCHIMICA ACTA 51 (7): 1322-1329, 2006.

Lu, W; Belharouak, I; Vissers, D; Amine, K. In situ thermal study of Li1+x[Ni1/3Co1/3Mn1/3](1−x)O−2 using isothermal micro-calorimetric techniques. JOURNAL OF THE ELECTROCHEMICAL SOCIETY 153 (11): A2147-A2151, 2006.

W. Lu; I. Belharouak; J. Liu; K. Amine, JOURNAL OF POWER SOURCES 174 (2007): 673-677.

Lu, W; Belharouak, I; Park, S H; Sun, Y K; Amine, K. Isothermal calorimetry investigation of Li1+xMn2−yAlzO4 spinel. ELECTROCHIMICA ACTA 52 (19): 5837-5842, 2007.

A. Mabuchi, K. Tokumitsu, H. Fujimoto, T. Kasuh, *J. Electrochem. Soc.* 142, 1041 (1995).

Maier J., JOURNAL OF POWER SOURCES 174 (2007): 569-574.

J. Mering and J. Maire, *J. Chim. Phys. Fr.* 57, 803 (1960).

Y. Mori, T. Iriyama, T. Hashimoto, S. Yamazaki, F. Kawakami, H. Shiroki and T. Yamabe, *J. Power Sources* 56, 205 (1995).

Nikiel L, W, Raman-Spectroscopic Characterization of Graphites—A Reevaluation Of Spectra/Structure Correlation, Carbon, 31(8): 1313-1317, 1993.

Ng et al., Applied Energy 86 (2009) 1506-1511.

Ng, Kong-Soon Soon, Huang, Yao-Feng, Moo, Chin-Sien Sien, Hsieh, Yao-Ching C, "An enhanced coulomb counting method for estimating state-of-charge and state-of-health of lead-acid batteries," *INTELEC* 31*st*, Incheon, South KR R.O, 2009.

A. Oberlin and G. Terriere, *Carbon,* 13, 367 (1975).

Oberlin A, Carbonization and Graphitization, Carbon 22 (6): 521-541, 1984.

Ohshima, T; Nakayama, M; Fukuda, K; Araki, T; Onda, K. Thermal behavior of small lithium-ion secondary battery during rapid charge and discharge cycles. ELECTRICAL ENGINEERING IN JAPAN 157 (3): 17-25, 2006.

Ohzuku T, Ueda A, Solid-state redox reactions of LiCoO2 (R(3)over-bar-m) for 4 volt secondary lithium cells, JOURNAL OF THE ELECTROCHEMICAL SOCIETY, 141 (11): 2972-2977, 1994.

Okamoto, E; Nakamura, M; Akasaka, Y; Inoue, Y; Abe, Y; Chinzei, T; Saito, I; Isoyama, T; Mochizuki, S; Imachi, K; Mitamura, Y. Analysis of heat generation of lithium ion rechargeable batteries used in implantable battery systems for driving undulation pump ventricular assist device. ARTIFICIAL ORGANS 31 (7): 538-541, 2007.

Ol'shanskaya, L N; Astaf'eva, E N. Thermodynamics of lithium intercalates in carbonized fabric. RUSSIAN JOURNAL OF APPLIED CHEMISTRY 75 (5): 740-744, 2002.

Paddon, C A; Jones, S E W; Bhatti, F L; Donohoe, T J; Compton, R G. Kinetics and thermodynamics of the Li/Li+ couple in tetrahydrofuran at low temperatures (195-295 K). JOURNAL OF PHYSICAL ORGANIC CHEMISTRY 20 (9): 677-684, 2007.

P. Papanek, M. Radosavljevic and J. E. Fischer, *Chem. Mater.* 8, 1519 (1996).

P. Papanek, W. A. Kamitakahara, P. Zhou and J. E. Fischer, *J. Phys. Condens. Matter* 13, 8287 (2001).

S. Piller, M. Perrin, A. Jossen, "Methods for state-of-charge determination and their applications" J. Power Sources, vol. 96, pp. 113-120, 2001.

Quintin, M; Devos, O; Delville, M H; Campet, G. Study of the lithium insertion-deinsertion mechanism in nanocrystalline gamma-Fe2O3 electrodes by means of electrochemical impedance spectroscopy. ELECTROCHIMICA ACTA 51 (28): 6426-6434, 2006.

Rao, L; Newman, J. Heat-generation rate and general energy balance for insertion battery systems. JOURNAL OF THE ELECTROCHEMICAL SOCIETY 144 (8): 2697-2704, 1997.

Remmlinger et al., J. Power Sources 196 (2011) 5357-5363.

Reynier, Y; Yazami, R; Fultz, B. The entropy and enthalpy of lithium intercalation into graphite. JOURNAL OF POWER SOURCES 119: 850-855, 2003.

Reynier, Y F; Yazami, R; Fultz, B. Thermodynamics of lithium intercalation into graphites and disordered carbons. J. Electrochem. Soc. 151 (3): A422-A426, 2004.

Saito, Y; Kanari, K; Takano, K. Thermal studies of a lithium-ion battery. JOURNAL OF POWER SOURCES 68 (2): 451-454, 1997.

Sandhu, S S; Fellner, J P. Thermodynamic equations for a model lithium-ion cell. ELECTROCHIMICA ACTA 45 (6): 969-976, 1999.

Schoonman, J. Nanoionics. SOLID STATE IONICS 157 (1-4): 319-326, 2003.

Selman, J R; Al Hallaj, S; Uchida, I; Hirano, Y. Cooperative research on safety fundamentals of lithium batteries. JOURNAL OF POWER SOURCES 97-8: 726-732, 2001.

Shi, S Q; Wang, D S; Meng, S; Chen, L Q; Huang, X J. First-principles studies of cation-doped spine LiMn2O4 for lithium ion batteries. PHYSICAL REVIEW B 67 (11) 2003.

Shi, S; Ouyang, C; Lei, M; Tang, W. Effect of Mg-doping on the structural and electronic properties of LiCoO2: A first-principles investigation. JOURNAL OF POWER SOURCES 171 (2): 908-912, 2007.

Shiraishi Y, Nakai I, Kimoto K, Matsui Y, EELS analysis of electrochemically deintercalated Li1−xMn2O4 and substituted spinels LiMn1.6M0.4O4 (M=Co, Cr, Ni), JOURNAL OF POWER SOURCES 97-8: 461-464, 2001.

Shin Y J, Manthiram A, Factors influencing the capacity fade of spinel lithium manganese oxides, JOURNAL OF THE ELECTROCHEMICAL SOCIETY 151 (2): A204-A208, 2004.

I. Snihir, W. Rey, E. Verbitsky, A. B. Ayeb and P. H. L. Notten, "Battery open-circuit voltage estimation by a method of statistical analysis," J. Power Sources, Vol. 159, No. 2, pp. 1484-1487, 2006.

D. A. Stevens and J. R. Dahn, J. Electrochem. Soc. 148, A803 (2001).

Takahashi, Y; Kijima, N; Dokko, K; Nishizawa, M; Uchida, I; Akimoto, J. Structure and electron density analysis of electrochemically and chemically delithiated LiCoO2 single crystals. JOURNAL OF SOLID STATE CHEMISTRY 180 (1): 313-321, 2007.

Takano, K; Saito, Y; Kanari, K; Nozaki, K; Kato, K; Negishi, A; Kato, T. Entropy change in lithium ion cells on charge and discharge. JOURNAL OF APPLIED ELECTROCHEMISTRY 32 (3): 251-258, 2002.

TARASCON J M, GUYOMARD D, Li metal-free rechargeable batteries based on Li1+xMn2O4 cathodes (0 less-than-or-equal-to x less-than-or-equal-to 1) and carbon anodes, JOURNAL OF THE ELECTROCHEMICAL SOCIETY, 138 (10): 2864-2868, 1991.

Thomas, K E; Bogatu, C; Newman, J. Measurement of the entropy of reaction as a function of state of charge in doped and undoped lithium manganese oxide. JOURNAL OF THE ELECTROCHEMICAL SOCIETY 148 (6): A570-A575, 2001.

Thomas, K E; Newman, J. Thermal modeling of porous insertion electrodes. JOURNAL OF THE ELECTROCHEMICAL SOCIETY 150 (2): A176-A192, 2003.

Thomas, K E; Newman, J. Heats of mixing and of entropy in porous insertion electrodes. JOURNAL OF POWER SOURCES 119: 844-849, 2003.

Tuinstra F, Koenig J L, Raman Spectrum Of Graphite, J. Chem. Phys. 53, 1126 (1970). Van der Ven A, Aydinol M K, Ceder G, First-principles evidence for stage ordering in LixCoO2, JOURNAL OF THE ELECTROCHEMICAL SOCIETY, 145 (6): 2149-2155, 1998.

Vicente, C P; Lloris, J M; Tirado, J L. Understanding the voltage profile of Li insertion into LiNi0.5−yFeyMn1.5O4 in Li cells. ELECTROCHIMICA ACTA 49 (12): 1963-1967, 2004.

Vitins, G; West, K. Lithium intercalation into layered LiMnO2. JOURNAL OF THE ELECTROCHEMICAL SOCIETY 144 (8): 2587-2592, 1997.

N. Wada, P. J. Gaczi and S. A. Solin, J. Non-Cryst. Solids 35, 543 (1980).

Wagemaker, M; Van Der Ven, A; Morgan, D; Ceder, G; Mulder, F M; Kearley, G J. Thermodynamics of spinel LixTiO2 from first principles. CHEMICAL PHYSICS 317 (2-3): 130-136, 2005.

Wakihara M, Lithium manganese oxides with spinel structure and their cathode properties for lithium ion battery, ELECTROCHEMISTRY, 73 (5): 328-335, 2005.

Wang, M J; Navrotsky, A. Enthalpy of formation of LiNiO2, LiCoO2 and their solid solutions LiNi1−xCoxO2. SOLID STATE IONICS 166 (1-2): 167-173, 2004.

Wang, M J; Navrotsky, A. LiMO2 (M=Mn, Fe, and Co): Energetics, polymorphism and phase transformation. JOURNAL OF SOLID STATE CHEMISTRY 178 (4): 1230-1240, 2005.

Wang, L; Maxisch, T; Ceder, G. A first-principles approach to studying the thermal stability of oxide cathode materials. CHEMISTRY OF MATERIALS 19 (3): 543-552, 2007.

Xu, J J; Jain, G. Nanocrystalline ferric oxide cathode for rechargeable lithium batteries. ELECTROCHEMICAL AND SOLID STATE LETTERS 6 (9): A190-A193, 2003.

Yamaki, J; Egashira, M; Okada, S. Potential and thermodynamics of graphite anodes in Li-ion cells. JOURNAL OF THE ELECTROCHEMICAL SOCIETY 147 (2): 460-465, 2000.

Yamaki, J; Egashira, M; Okada, S. Voltage prediction from Coulomb potential created by atoms of spinel LiMn2O4 cathode active material for Li ion cells. JOURNAL OF POWER SOURCES 97-8: 349-353, 2001.

Yamaki, J; Egashira, M; Okada, S. Thermodynamics and phase separation of lithium intercalation materials used in lithium ion cells. ELECTROCHEMISTRY 69 (9): 664-669, 2001.

R. Yazami and Y. Reynier, J. Power Sources 153 (2006) 312-318.

Zhou, F; Maxisch, T; Ceder, G. Configurational electronic entropy and the phase diagram of mixed-valence oxides: The case of lixfepo4. PHYSICAL REVIEW LETTERS 97 (15) 2006.

US Patent Application Publications US 2007/0182418, US 2010/0090650, US 2006/0100833, US 2001/0001533, US 2006/0208704, US 2004/0220758, US 2004/0128089, US 2004/0046564, US 2011/0121786.

U.S. Pat. Nos. 7,595,611; 7,132,832; 7,109,685; 4,295,097; 6,667,131; 4,725,784; 7,227,336; 6,392,385; 6,016,047.

PCT International Application Publications WO 2007/117263, WO 2010/105062.

STATEMENTS REGARDING INCORPORATION BY REFERENCE AND VARIATIONS

The following references relate generally to the composition and function of electrochemical cells and the thermodynamic analysis of electrochemical data and are incorporated by reference in their entireties herein: Handbook of Batteries, Edited by David Linden and Thomas B. Reddy, Third Edition, McGraw-Hill, 2002; and Battery Technology Handbook, Edited by H. A. Kiehne, Marcel Dekker, Inc., 2003.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The following patents, patent applications and publications are hereby incorporated by reference in their entireties: U.S. applications Ser. Nos. 11/462,290, 12/537,712, 13/215,506; U.S. Provisional Applications 60/705,535, 61/159,727, 61/639,712, 61/260,751, 61/376,208, 61/556,037, 61/726,459, 61/536,239; U.S. Pat. No. 7,595,611; US Patent Application Publications US 2007/0182418, US 2010/0090650, US 2012/0043929.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups and classes that can be formed using the substituents are disclosed separately. When a Markush group or other grouping is used herein, all individual members of the group and all combinations and subcombinations possible of the group are intended to be individually included in the disclosure. As used herein, "and/or" means that one, all, or any combination of items in a list separated by "and/or" are included in the list; for example "1, 2 and/or 3" is equivalent to "'1' or '2' or '3' or '1 and 2' or '1 and 3' or '2 and 3' or '1, 2 and 3'"; for example "1, 2 and/or 3" is also equivalent to "one or more of 1, 2 and 3".

Every formulation or combination of components described or exemplified can be used to practice the invention, unless otherwise stated. Specific names of materials are intended to be exemplary, as it is known that one of ordinary skill in the art can name the same material differently. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A device for monitoring a condition of an electrochemical cell, the device comprising an integrated circuit comprising:
   a voltage monitoring circuit for measuring a plurality of open circuit voltages of said electrochemical cell, said plurality of open circuit voltages generated upon charging or discharging said electrochemical cell or stopping charging or discharging said electrochemical cell;
   a temperature monitoring circuit for measuring a plurality of temperatures of said electrochemical cell, said plurality of temperatures generated upon charging or discharging said electrochemical cell or stopping charging or discharging said electrochemical cell;
   a current monitoring circuit for measuring a charging current of said electrochemical cell or a discharging current of said electrochemical cell; and
   a circuit for determining a thermodynamic parameter of said electrochemical cell, wherein said thermodynamic parameter is one or more of a change in entropy of said electrochemical cell, a change in enthalpy of said electrochemical cell and a change in free energy of said electrochemical cell, said circuit for determining a thermodynamic parameter positioned in electrical or data communication with said temperature monitoring circuit to receive temperature measurements from said temperature monitoring circuit, positioned in electrical or data communication with said voltage monitoring circuit to receive open circuit voltage measurements from said voltage monitoring circuit and positioned in electrical or data communication with said current monitoring circuit to receive current measurements from said current monitoring circuit or to provide thermodynamics parameters to said current monitoring circuit;

wherein said device does not comprise a temperature controller or a means for controlling or establishing said plurality of temperatures generated upon charging or discharging said electrochemical cell or stopping charging or discharging said electrochemical cell.

2. The device of claim 1, wherein said device is embedded into said electrochemical cell or is attached to or contained within a housing of said electrochemical cell.

3. The device of claim 1, further comprising a temperature sensor positioned in thermal communication with said electrochemical cell, said temperature sensor further positioned in electrical or data communication with said temperature monitoring circuit.

4. The device of claim 1, wherein said temperature monitoring circuit determines or monitors a temperature of said electrochemical cell as said electrochemical cell is charging or discharging.

5. The device of claim 1, wherein said temperature monitoring circuit determines or monitors a temperature of said electrochemical cell when said electrochemical cell is not charging or when said electrochemical cell is not discharging.

6. The device of claim 1, wherein the integrated circuit comprises a circuit for determining an open circuit state of the electrochemical cell.

7. The device of claim 6, wherein the integrated circuit comprises a power switching circuit.

8. The device of claim 1, wherein said device is a component of an automobile; and wherein said voltage monitoring circuit measures said plurality of open circuit voltages of said electrochemical cell when said automobile is idle, stopped, parked, powered off, powering off, powered on, powering on, accelerating or decelerating, wherein said temperature monitoring circuit measures said plurality of temperatures of said electrochemical cell when said automobile is idle, stopped, parked, powered off, powering off, powered on, powering on, accelerating or decelerating or wherein both said voltage monitoring circuit measures said plurality of open circuit voltages of said electrochemical cell and said temperature monitoring circuit measures said plurality of temperatures of said electrochemical cell said automobile is idle, stopped, parked, powered off, powering off, powered on, powering on, accelerating or decelerating.

9. The device of claim 8, wherein a change in open circuit voltage of said electrochemical cell occurs when said automobile is idle, stopped, parked, powered off, powering off, powered on, powering on, accelerating or decelerating.

10. The device of claim 1, wherein said device is a component of a portable electronic device; and wherein said voltage monitoring circuit measures said plurality of open circuit voltages of said electrochemical cell when said portable electronic device is idle, powered off, powering off, powered on or powering on, wherein said temperature monitoring circuit measures said plurality of temperatures of said electrochemical cell when said portable electronic device is idle, powered off, powering off, powered on or powering on or wherein both said voltage monitoring circuit measures said plurality of open circuit voltages of said electrochemical cell and said temperature monitoring circuit measures said plurality of temperatures of said electrochemical cell when said portable electronic device is idle, powered off, powering off, powered on or powering on.

11. The device of claim 10, wherein a change in open circuit voltage of said electrochemical cell occurs when said portable electronic device is idle, powered off, powering off, powered on or powering on.

12. The device of claim 1, wherein said thermodynamic parameter of said electrochemical cell is determined using one or more of said plurality of open circuit voltages of said electrochemical cell and said plurality of temperatures of said electrochemical cell.

13. The device of claim 1, wherein said thermodynamic parameter of said electrochemical cell is determined using a first temperature of said electrochemical cell and a second temperature of said electrochemical cell different from said first temperature of said electrochemical cell.

14. The device of claim 1, wherein said change in free energy is determined by measuring an open circuit voltage of said electrochemical cell.

15. The device of claim 1, wherein said integrated circuit comprises a state of charge calculating circuit for determining a state of charge of said electrochemical cell, said state of charge calculating circuit receiving current measurements from said current monitoring circuit and thermodynamic parameters of said electrochemical cell from said circuit for determining a thermodynamic parameter.

16. The device of claim 15, wherein said state of charge calculating circuit comprises said current monitoring circuit.

17. The device of claim 15, wherein said integrated circuit monitors said electrochemical cell as said electrochemical cell is charged under controlled conditions and updates entries in a look-up table as said electrochemical cell is charged under controlled conditions, said look-up table including entries of states of charge of said electrochemical cell, open circuit voltages of said electrochemical cell and thermodynamic parameters of said electrochemical cell.

18. The device of claim 1, wherein said voltage monitoring circuit determines an open circuit voltage of said electrochemical cell when said electrochemical cell is not charging or when said electrochemical cell is not discharging.

19. The device of claim 1, wherein said circuit for determining a thermodynamic parameter of said electrochemical cell further determines one or more of a state of health of said electrochemical cell, a state of safety of said electrochemical cell and a cycle number of said electrochemical cell.

20. The device of claim 1, wherein said device determines an entropy, a change in entropy, a temperature or a differential entropy of said electrochemical cell and compares said entropy, change in entropy, temperature or differential entropy of said electrochemical cell with a reference entropy, a reference change in entropy, a reference temperature or a reference differential entropy and disables charging or discharging said electrochemical cell when said determined entropy, change in entropy, temperature or differential entropy is different from said reference entropy, reference change in entropy, reference temperature or reference differential entropy.

21. The device of claim 1, wherein said device is a component of a package comprising said device and one or more electrochemical cells.

22. The device of claim 1, wherein said device is positioned in selective data communication or selective electrical communication with one or more electrochemical cells.

23. The device of claim 1, wherein said integrated circuit further comprises a circuit for determining one or more of a state of health of said electrochemical cell, a state of safety of said electrochemical cell and a cycle number of said electrochemical cell.

24. A method of determining a condition of an electrochemical cell, the method comprising the steps of:
    providing a device comprising an integrated circuit comprising:
        a voltage monitoring circuit for measuring a plurality of open circuit voltages of said electrochemical cell, said plurality of open circuit voltages generated upon charging or discharging said electrochemical cell or stopping charging or discharging said electrochemical cell;
        a temperature monitoring circuit for measuring a plurality of temperatures of said electrochemical cell, said plurality of temperatures generated upon charging or discharging said electrochemical cell or stopping charging or discharging said electrochemical cell;
        a current monitoring circuit for measuring a charging current of said electrochemical cell or a discharging current of said electrochemical cell; and
        a circuit for determining a thermodynamic parameter of said electrochemical cell, wherein said thermodynamic parameter is one or more of a change in entropy of said electrochemical cell, a change in enthalpy of said electrochemical cell and a change in free energy of said electrochemical cell, said circuit for determining a thermodynamic parameter positioned in electrical or data communication with said temperature monitoring circuit to receive temperature measurements from said temperature monitoring circuit, positioned in electrical or data communication with said voltage monitoring circuit to receive open circuit voltage measurements from said voltage monitoring circuit and positioned in electrical or data communication with said current monitoring circuit to receive current measurements from said current monitoring circuit or to provide thermodynamics parameters to said current monitoring circuit;
        wherein said device does not comprise a temperature controller or a means for controlling or establishing said plurality of temperatures generated upon charging or discharging said electrochemical cell or stopping charging or discharging said electrochemical cell of said electrochemical cell;
    generating said plurality of open circuit voltages of said electrochemical cell, said plurality of temperatures of said electrochemical cell or both said plurality of open circuit voltages of said electrochemical cell and said plurality of temperatures of said electrochemical cell; and
    determining a first thermodynamic parameter of said electrochemical cell using said integrated circuit.

25. The method of claim 24 further comprising the steps of:
    providing a reference array of values comprising thermodynamic parameter values for a reference electrochemical and cell condition values for said reference electrochemical cell;
    determining a thermodynamic parameter for said electrochemical cell; and
    determining said condition of said electrochemical cell using said reference array of values, wherein said condition of said electrochemical cell corresponds to a cell condition of said reference electrochemical cell for a reference thermodynamic value equal to said determined thermodynamic parameter for said electrochemical cell.

26. The method of claim 24; wherein said determining said first thermodynamic parameter of said electrochemical cell using said integrated circuit comprises determining an entropy of said electrochemical cell.

27. The method of claim 26; further comprising comparing said entropy of said electrochemical cell to a reference entropy.

28. The method of claim 27; further comprising disabling said electrochemical cell from charging or discharging when said determined entropy of said electrochemical cell is different from said reference entropy.

29. The method of claim 27; wherein said disabling step comprises actuating a switch, relay or transistor in electrical communication with an electrode of said electrochemical cell, thereby disabling charging or discharging said electrochemical cell.

* * * * *